(12) United States Patent
Kopetzki et al.

(10) Patent No.: US 11,591,383 B2
(45) Date of Patent: Feb. 28, 2023

(54) METHOD FOR SELECTING POLYPEPTIDE PRODUCING CELLS

(71) Applicant: Hoffmann-La Roche Inc., Little Falls, NJ (US)

(72) Inventors: Erhard Kopetzki, Penzberg (DE); Oliver Ploettner, Gilching (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 622 days.

(21) Appl. No.: 16/367,766

(22) Filed: Mar. 28, 2019

(65) Prior Publication Data

US 2020/0157189 A1    May 21, 2020

Related U.S. Application Data

(63) Continuation of application No. PCT/EP2017/074481, filed on Sep. 27, 2017.

(30) Foreign Application Priority Data

Sep. 29, 2016  (EP) .................................... 16191586

(51) Int. Cl.
*C12N 15/85*      (2006.01)
*C07K 16/00*      (2006.01)

(52) U.S. Cl.
CPC ............ *C07K 16/00* (2013.01); *C12N 15/85* (2013.01); *C07K 2317/14* (2013.01); *C07K 2317/526* (2013.01); *C07K 2317/528* (2013.01); *C07K 2319/03* (2013.01); *C12N 2830/20* (2013.01); *C12N 2830/42* (2013.01)

(58) Field of Classification Search
None
See application file for complete search history.

(56) References Cited

U.S. PATENT DOCUMENTS

| | | | |
|---|---|---|---|
| 4,656,134 | A  | 4/1987  | Ringold |
| 5,888,809 | A  | 3/1999  | Allison |
| 2002/0168702 | A1 | 11/2002 | Fandl et al. |
| 2003/0033616 | A1 | 2/2003  | Star-Lack et al. |
| 2004/0148647 | A1 | 7/2004  | Enenkel et al. |
| 2005/0032127 | A1 | 2/2005  | Marx et al. |

FOREIGN PATENT DOCUMENTS

| | | |
|---|---|---|
| WO | 92/08796 | 5/1992 |
| WO | 94/28143 | 12/1994 |
| WO | 01/04306 | 1/2001 |
| WO | 01/38557 A1 | 5/2001 |
| WO | 2001/92291 | 12/2001 |
| WO | 2005/020924 A | 3/2005 |
| WO | 2005/040213 | 5/2005 |
| WO | 2005/089285 | 9/2005 |
| WO | 2007/131774 A1 | 11/2007 |
| WO | 2013/092720 A1 | 6/2013 |
| WO | 2013/177481 A1 | 11/2013 |

OTHER PUBLICATIONS

Alt, Frederick W., et al., "Synthesis of Secreted and Membrane-Bound Immunoglobulin Mu Heavy Chains Is Directed by mRNAs That Differ at Their 3' Ends" Cell 20:293-301 (Jun 1, 1980).
Ancian, Philippe, et al., "The Human 180-kDa Receptor for Secretory Phospholipases A2" J Biol Chem 270(15):8963-8970 (Apr. 14, 1995).
Ausubel et al. Current Protocols in Molecular Biology "Percentage of Codon Synonomous Usage and Frequency of Codon Occurrence in Various Organisms" (A1.8-A1.9 (tables)),John Wiley & Sons, Inc., vol. 5:A.1C.1-A.1C.12 ( 1997).
Banerji et al. et al., "A Lymphocyte-specific Cellular Enhancer Is Located Downstream of the Joining Region in Immunoglobulin Heavy Chain Genes" Cell 33:729-740 (Jul. 1983).
Bird et al., "Single-chain antigen-binding proteins" Science 242:423-426 (Oct. 21, 1988).
Black, Douglas L.,, "Mechanisms of Alternative Pre-Messenger RNA Splicing" Annu Rev Biochem 72:291-336 (Feb. 27, 2003).
Callaghan, Thomas et al., "A complete description of the EGF-receptor exon structure: implication in oncogenic activation and domain evolution" Oncogene 8:2939-2948 (Jul. 2, 1993).
Cartgeni, L., et al., "ESEfinder: a web resource to identify exonic splicing enhancers" Nucleic Acids Res 31(13):3568-3571 (Jul. 1, 2003).
Celis, et al. Cell Biology: a Laboratory Handbook Second Edition edition, New York, NY:Academic Press, vol. I-III:1-638 (Dec. 1, 1195).
Connor, R.J., et al., "Genomic organization and alternatively processed forms of Cek5, a receptor protein-tyrosine kinase of the Eph subfamily" Oncogene 11(11):2429-2438 (Dec. 1, 1995).
Cushley, W., et al., "A common mechanism for the synthesis of membrane and secreted immunoglobulin α, γand μ chains" Nature 298:77-79 (Jul. 1, 1982).

(Continued)

*Primary Examiner* — Michael D Burkhart
(74) *Attorney, Agent, or Firm* — Charles Wong

(57) ABSTRACT

Herein is reported a nucleic acid comprising in 5' to 3' direction i) a first nucleic acid fragment encoding a polypeptide of interest without an in frame translational stop codon, ii) a second nucleic acid fragment operably linked to said first nucleic acid fragment which is beginning with the 5' splice donor site of an immunoglobulin heavy chain CH3 or CH4 domain and which is terminated by the 3' splice acceptor site of the succeeding immunoglobulin heavy chain transmembrane domain exon M1 and which comprises in frame translational stop codon and a polyadenylation signal, and iii) a third nucleic acid fragment operably linked to said second nucleic acid encoding at least a fragment of a transmembrane domain, wherein the second nucleic acid fragment has at its 3' terminus the nucleotide sequence CTACCACCCCTTCCTGTCCAG (SEQ ID NO: 29) or TGACCACGCCAATCGTGTCCAG (SEQ ID NO: 14) or CTACCACGCCAATCGTGTCCAG (SEQ ID NO: 31).

13 Claims, 14 Drawing Sheets

Specification includes a Sequence Listing.

(56) References Cited

OTHER PUBLICATIONS

Danner, D et al., "Role of an RNA cleavage/poly(A) addition site in the production of.membrane-bound and secreted IgM mRNA," Proceedings of the Natl Acad of Sci 82(24):8658-8662 ( 1985).
Early et al. et al., "Two mRNAs can be produced from a single immunoglobulin µ Gene by alternative RNA processing pathways" Cell 20:313-319 (Jun. 1, 1980).
Emorine, Laurent, et al., "A conserved sequence in the immunoglobulin JK-CK intron: possible enhancer element" Nature 304:447-449 (Aug. 4, 1983).
Fallot, S., et al., "Alternative-splicing-based bicistronic vectors for ratio-controlled protein expression and application to recombinant antibody production" Nucleic Acids Res 37(20):e134 (Sep. 3, 2009).
Freshney, "Culture of Specific Cell Types" Culture of Animal Cells A Manual of Basic Technique pp. 267-268 (1987).
Freshney, R. I , Animal cell culture—a practical approach Freshney, R. I. (ed.), Oxfordz:IRL Press Limited,:(entire book) ( 1986).
Freshney, R. I , Animal cell culture: A Practical Approach Freshney (ed.), 2nd edition, NY:Oxford University Press,:(entire book) ( 1992).
Gillies, Stephen D., et al., "A tissue-specific transcription enhancer element is located in the imaj or intron of a rearranged immunoglobulin heavy chain gene" Cell 33:717-728 (Jul. 1, 1983).
Glover, D.M. , DNA Cloning—A Practical Approach, Glover, D.M. (ed.), Oxfordz:IRL Press Limited, vol. I and II:(entire book) ( 1985).
Goeddel Methods in Enzymology: Gene Expression Technology "Section 1—Systems for Heterologous Gene Expression" (with Table of Contents, total in 13 pages), Goeddel, San Diego, CA:Academic Press, Inc., vol. 185:3-7 ( 1990).
Gossen, M., et al. et al., "Inducible gene expression systems for higher eukaryotie cells" Curr Opin Biotechnol 5:516-520 ( 1994).
Gossen, M., et al, "Tight control of gene expression in mannnalian cells by tetracycline-responsive promoters" PNAS 89:5547-5551 (Jun. 1, 1992).
Hames, B.D., eds. et al. Nucleic Acid Hybiidisation: A Practical Approach Hames, B.D. and Higgins, S.J.,IRL Press/Oxford Univ Press,:1-264 (Dec. 1, 1985).
Harris, C. et al., "Efficient generation of monoclonal antibodies for specific protein domains using recombinant immunoglobulin fusion proteins: pitfalls and solutions" J Immunol Methods 268(2):245-258 (May 27, 2002).
Hood et al. Immunology 2nd edition Benjamin, NY,:2 pages ( 1984).
Hourcade, Dennis, et al., "Identification of an Alternative Polyadenylation Site in the Human C3b/C4b Receptor (Complement Receptor Type 1) Transcriptional unit and Prediction of a Secreted Form of Complement Receptor Type 1" J Exp Med 168:1255-1270 (Oct. 1, 1988).
Hunkapiller and Hood, "The growing immunoglobulin gene superfamily" nature 323:15-16 (Sep. 4, 1986).
Huston et al., "Protein engineering of antibody binding sites: Recovery of specific activity in an anti-digoxin single-chain FV analogue produced in *Escherichia coli*" P Natl Acad Sci USA 85:5879-5883 (Aug. 1988).
EInternational Preliminary Report on Patentability (IPRP) for PCT/EP2017/0744841 dated Apr. 2, 2019.
International Search Report for PCT/EP2017/074481 dated Dec. 8, 2017.
Johnson, Daniel E., et al., "The Human Fibroblast Growth Factor Receptor Genes: a Common Structural Arrangement Underlies the Mechanisms for Generating Receptor Forms That Differ in Their Third Immunoglobulin Domain" Mol Cell Biol 11(9):4627-4634 (Sep. 1, 1991).
Kaufman and Sharp et al., "Amplification and Expression of Sequences Co-transfected with a Modular Dihydrofolate Reductase Complementary DNA Gene" J Mol Biol 159(4):601-621 (Aug. 25, 1982).
Kobrin, Barry J., et al., "Sequences near the 3' Secretion-Specific Polyadenylation Site Influence Levels of Secretion-Specific and Membrane-Specific IgG2b mRNA in Myeloma Cells" Mol Cell Biol 6(5):1687-1697 (May 1, 1986).
Kozak, "An analysis of 5'-noneoding sequences from 699 vertebrate messenger RNAs" Nucleic Acids Res 15(20):8125-8148 (Oct. 26, 1987).
Lemaigre, F. P., et al., "Transcriptional control of genes that regulate glycolysis and gluconeogenesis in adult liver" Biochem J 303:1-14 (Jan. 1, 1994).
Loeken, Mary R., "Effects of mutation of the CREB binding site of the somatostatin promoter on cyclic AMP responsiveness in CV-1 cells" Gene Expression 3(3):253-264 (Sep. 27, 1993).
Major, J.G., et al., "Structural Features of the Extracellular Portion of Membrane-Anchoring Peptides on Membrane-Bound Irnrnunoglobulins" Mol Immunol 33(2):179-187 (Jun. 29, 1995).
Marine, M.H., "Expression Systems for Heterologous Protein Production" BioPharm 2:18-33 (Jul. 1, 1989).
McGehee, Jr. D. Ron et al., "Differentiation-specific element: a cis-aeting developmental switch required for the sustained transcriptional expression of the angiotensinogen gene during hormonal-induced differentiation of 3T3-L1 fibroblasts to adipoeytes" Mol Endocrinol 7(4):551-560 (Apr. 1, 1993).
Milcarek, C. et al., "Cell-Specific Expression of Secreted Versus Membrane Forms of Immunoglobulin Gamma 2b mRNA Involves Selective Use of Alternate Polyadenylation Sites" Mol Cell Biol 5(10):2514-2520 (Oct. 1, 1985).
Modrek, Barmak, et al., "Genome-wide detection of alternative splicing in expressed sequences of human genes" Nucleic Acids Research 29(13):2850-2859 (May 5, 2001).
Nussaume L. et al., "Analysis of splice donor and acceptor site function in a transposable gene trap derived from the maize element Activator" Molecular and General Genetics 249(1):91-101 (Jun. 12, 1995).
O'Reilly, M.A., et al., "Identification of an Activating Transcription Factor( ATF) Binding Site in the Human Transforming Growth Factor-β2 Promoter" J Biol Chem 267(28):19938-19943 (Oct. 5, 1992).
Petch et al. et al., "A truncated, secreted form of the epidermal growth factor receptor is encoded by an alternatively spliced transcript in normal rat tissue" Mol Cell Biol 10(6):2973-2982 (Jun. 1990).
Peterson, Martha L., "Balanced efficiencies of splicing and cleavage-polyadenylation are required for µs and µm rnRNA regulation" Gene Expression 2(4):319-327 (Jun. 19, 1992).
Picard, Didier et al., "A lymphocyte-specific enhancer in the mouse immuno globulin K gene" Nature 307:80-82 (Jan. 5, 1984).
Prochownik, E.V et al., "In Vivo Transcription of a Human Antithrombin III Minigene," J Biol Chem 259(24):15386-15392 (Dec. 25, 1984).
Puck, Theodore T. et al., "Genetics of Somatic Mammalian Cells" J Exp Med 108:945-956 (Jul. 24, 1958).
Reiter, Jill L., et al., "A 1.8 kb alternative transcript from the human epidermal growth factor receptor gene encodes a truncated form of the receptor" Nucleic Acids Res 24(20):4050-4056 (Aug. 16, 1996).
Rogers et al. et al., "Two mRNAs with different 3' ends encode membrane-bound and secreted forms of immunoglobulin µ chain" Cell 20(2):303-312 (Jun. 1980).
Sambrook et al. Molecular Cloning: A Laboratory Manual (Table of Contents only, in 32 pages), 2nd edition, Cold Spring Harbor, NY:Cold Spring Harbor Laboratory Press, ( 1989).
Treisman, Richard, "The SRE: a growth factor responsive transcriptional regulator" Semin Cancer Biol 1(1):47-58 (Feb. 1, 1990).
Wang, Z., et al., "Splicing regulation: From a parts list of regulatory elements to an integrated splicing code" RNA Cold Spring Harb Sym 14(5):802-813 (Mar. 27, 2008).
Watson, J. Molecular Biology of the Gene (cbook is not provided), Menlo Park, CA:W.A. Benjamin (1976).
Watson, James D., et al. Recombinant DNA Second Edition edition, New York, NY:CSHL Press,:1-619 (Jan. 1, 1992).
Winnacker, From Genes to Clones: Introduction to Gene Technology (Preface), VCH pp. v-vii (1987).
Xiang, Sue D., et al., "Tracking membrane and secretory immunoglobulin a heavy chain mRNA variation during B-cell differentia-

(56) References Cited

OTHER PUBLICATIONS tion by real-time quantitative polymerase chain reaction" Immunol Cell Bio 79(5):472-481 (May 28, 2001).

Ye, Jia et al., "Glyeosaminoglyean Contributions to Both Protein C Activation and Thrombin Inhibition Involve a Common Arginine-rich Site in Thrombin That Includes Residues Arginine 93,97 and 101" J Biol Chem 269(27):17965-17970 (Jul. 8, 1994).

Zhang, Ke, et al., "Two Unusual Forms of Human Immuno globulin Encoded by Alternative RNA Splicing of a Heavy Chain Membrane Exons" J Exp Med 176:233-243 (Jul. 1, 1992).

Zhang, M.Q.,, "Statistical features of human exons and their flanking regions" Hum Mol Genet 7(5):919-932 (May 1, 1998).

Zhu Y et al., "Multigene LentiViral Vectors Based on Differential Splicing and Translational Control" Molecular Therapy, 4(4):375-382 ( 2001).

Fu et al., Int J Lab Med (CN OA Dec. 1, 2021), 33(11):1333-1336 ( 2012).

Wei et al., "Knockdown of PU . 1 mRNA and AS lncRNA regulates expression of immune-related genes of zebrafish Danio rerio" Development and Comparative Immunology(44):315-319 ( 2014).

METHOD FOR SELECTING POLYPEPTIDE PRODUCING CELLS

CROSS REFERENCE TO RELATED APPLICATIONS

This application is a continuation of International Application No. PCT/EP2017/074481 having an International Filing Date of Sep. 27, 2017, which claims the benefit of priority to European Patent Application No. 16191586.3 filed on Sep. 29, 2016, the entire contents of which are incorporated herein by reference.

SEQUENCE LISTING

The instant application contains a Sequence Listing submitted electronically in ASCII format and is hereby incorporated herein by reference in its entirety. Said ASCII copy, created Mar. 28, 2019, is named P33876-US_Sequence_Listing3.txt and is 40,927 bytes in size.

The current invention is in the field of polypeptide production. Herein is reported a nucleic acid comprising an alternatively spliceable nucleic acid, cells comprising this nucleic acid, a method for the isolation of cells expressing a recombinant (heterologous) polypeptide from the nucleic acid as reported herein, and also a method for the production of a recombinant (heterologous) polypeptide.

BACKGROUND OF THE INVENTION

Expression systems for the production of recombinant polypeptides are well-known in the state of the art and are described by, e.g., Marino, M. H., Biopharm. 2 (1989) 18-33; Goeddel, D. V., et al., Methods Enzymol. 185 (1990) 3-7; Wurm, F., and Bernard, A., Curr. Opin. Biotechnol. 10 (1999) 156-160. For the production of polypeptides and proteins used in pharmaceutical applications preferably mammalian host cells such as CHO cells, BHK cells, NSO cells, Sp2/0 cells, COS cells, HEK cells, PER.C6® cells and the like are employed. The nucleic acid encoding the polypeptide is preferably introduced into the host cell comprised in a nucleic acid, such as, for example, an expression plasmid. The essential elements of an expression plasmid are a prokaryotic plasmid propagation unit, e.g. for *Escherichia coli* comprising an origin of replication and a selection marker, a eukaryotic selection marker, and one or more expression cassettes for the expression of the structural gene(s) of interest each of them comprising a promoter, a structural gene, and a transcription terminator including a polyadenylation signal. For transient expression in mammalian cells a mammalian origin of replication, such as the SV40 Ori or OriP from EBV, may be included. As a promoter a constitutive or inducible promoter can be selected. For optimized transcription a Kozak sequence may be included in the 5' untranslated region. For mRNA processing, in particular transcription termination and pre-mRNA splicing, mRNA splicing signals, depending on the organization of the structural gene (exon-intron-organization), may be included as well as a polyadenylation signal.

Expression of a gene is performed either as transient or permanent expression. The polypeptide(s) of interest may be a secreted polypeptide, containing an N-terminal extension (also known as the signal sequence), which is necessary for the transport/secretion of the polypeptide through the cell and into the extracellular medium, or may be a cytosolic polypeptide.

For the large scale production of a polypeptide a high producer cell line has to be established. After the transfection of a host cell line, such as CHO cells, NSO cells, Sp2/0 cells, BHK cells, COS cells, PER.C6® cells, or HEK cells, in general a plurality of clones with different characteristics are obtained due to, for example, the broad difference of polypeptide expressed from transiently transfected or stably integrated plasmids. For selection purposes the nucleic acid introduced into cells possesses additionally a selectable marker, e.g. a gene conferring resistance against an otherwise fatal substance.

After transfection and by growth in an appropriate selective medium a high producer clone has to be isolated. This is time consuming and consequently expensive. Several methods have been developed to handle this problem.

One of these methods is gene amplification. Therein cells deficient of the enzyme dihydrofolate reductase (DHFR) are transfected with a plasmid/plasmid which contains a first expression cassette for the expression of the DHFR protein and a second expression cassette for the expression of a heterologous polypeptide of interest. By using a culture medium depleted of glycine, hypoxanthine, and thymidine selective growth conditions are established. For amplification a DHFR inhibitor, methotrexate (MTX), is added (Kaufman, R. J., et al., J. Mol. Biol. 159 (1982) 601-621; U.S. Pat. No. 4,656,134).

Alternatively reporter molecules, such as chloramphenicol-acetyl-transferase, luciferase, green fluorescent protein, or beta-galactosidase, can be fused to the heterologous polypeptide for which a high producer cell line is desired and used as an indirect selection marker. The selection takes place in the presence of an added exogenous substrate or cofactor.

A further method for the identification of a high producer clone is a linked transcription of a selectable marker gene and a structural gene encoding a heterologous polypeptide via an internal ribosome entry site (IRES). With this design the expression of the heterologous polypeptide can be correlated with the expression of the selectable marker.

Human immunoglobulins are produced by specialized lymphocytes, the B-cells. These cells do not only secrete immunoglobulins (sIg) they also present immunoglobulins on their outer cell membrane as plasma-membrane-bound immunoglobulins (mIg). These mIg's play an important role in the beginning of an immunological response. The presented plasma-membrane-bound immunoglobulins have the function of cellular receptors of their corresponding antigen.

Beginning in 1980 articles dealing with the origin of secreted and plasma-membrane-bound forms of immunoglobulins were published. Early et al. (Early, P., 10 et al., Cell 20 (1980) 313-319) reported that in mice two species of mRNA which encode the heavy chain of immunoglobulins originate from the same primary transcript of a single immunoglobulin μ-gene. The formation of the secreted (sIg) and the plasma-membrane-bound (mIg) forms results from alternative splicing of the heavy chain pre-mRNA. For the sIg isoform all exons coding for the domains of the immunoglobulin and the intron following the exon encoding the C-terminal domain are retained in the mRNA and the polyadenylation signal locates downstream of the stop codon in the intron is used for cleavage and polyadenylation of the primary transcript. For the mIg isoform an alternative 5' splice donor site after the exon encoding the C-terminal domain of the secreted form (i.e. CH3 or CH4, respectively) links the constant region with the downstream exons M1 and M2 encoding a transmembrane domain. In this case the sequence encoding the terminal amino acids and the stop codon of the secreted form, as well as the adjacent intronic polyadenylation signal for the sIg form are removed by the splicing process along with the intron.

For example, the ratio between the mRNA encoding the secreted immunoglobulin heavy chain form and the mRNA encoding the plasma-membrane-bound immunoglobulin heavy chain form is of from 10:1 to 100:1. This ratio is established mainly during pre-mRNA splicing. Translational and post-translational control mechanisms contribute only to a minor part (see e.g. Xiang, S. D., et al., Immun. Cell Biol. 79 (2001) 472-481).

The immunoglobulin bound to the cell's plasma-membrane has the same amino acid sequence and secondary structure as its secreted analogue. The difference is a C-terminal extension of the sIg's heavy chain comprising a transmembrane domain. This transmembrane domain has in general a length of between approx. 40 and approx. 75 amino acid residues. For murine and human immunoglobulins the transmembrane domain can be subdivided into three distinct structural regions: an N-terminal extracellular region of 13-67 amino acid residues, a central conserved transmembrane stretch of 25 amino acid residues, and a C-terminal cytoplasmatic region of 3-28 amino acid residues (Major, J. G., et al., Mol. Immunol. 33 (1996) 5 179-187).

Expression plasmids comprising an amplifiable selectable gene, a fluorescent protein gene, and a gene encoding a desired product in a manner that optimizes transcriptional and translational linkage is reported in WO 01/04306. In WO 01/38557 a method for screening multiply transformed/transfected cells to identify cells expressing at least two peptides or proteins of interest is reported. These two peptides/proteins are linked via an IRES (internal ribosome entry site) to a fluorescent marker gene.

Transgenic animals and cells that comprise an imaging marker transgene are reported in US 2003/0033616. US 2005/0032127 reports a method for the non-invasive selection of single living cells under gentle conditions from mixtures of cells or cell cultures with respect to a specific production performance by fluorescence-microscopic detection methods. A method for identifying and isolating cells which produce secreted proteins is reported in US 2002/0168702.

An expression plasmid consisting of a gene coding for a protein of interest which is functionally linked to a hamster promoter, a gene which codes for a fluorescent protein, and preferably an amplifiable selection marker gene is reported in US 2004/0148647.

A consensus sequence for 3'-splice sites was reported be Zhang, M., Hum. Mol. Genet. 7 (1998) 919-932.

In WO 01/92291 antibody and T-cell receptor libraries are reported. Methods and constructs for expressing polypeptide multimers in eukaryotic cells using alternative splicing are reported in WO 2005/089285. In WO 2005/040213 a modified cDNA for high expression levels of factor VIII and its derivatives is reported. In vivo transcription of a human antithrombin III minigene is reported by Prochownik, E. V. and Orkin, S. H. (J. Biol. Chem. 259 (1984) 15386-15392). Nussaume, L., et al. report the analysis of splice donor and splice acceptor site function in a transposable gene trap derived from the maize element activator (Mol. Gen. Genet. 249 (1995) 91-101). The genome-wide detection of alternative splicing in expressed sequences of human genes is reported by Modrek, B., et al. (Nucleic Acids Res. 29 (2001) 2850-2859). Danner, D. and Leder, P., report the role of an RNA cleavage/poly(A) addition site in the production of membrane-bound and secreted IgM mRNA (Proc. Natl. Acad. Sci. USA 82 (1985) 8658-8662). The efficient generation of monoclonal antibodies from specific protein domains using recombinant immunoglobulin fusion proteins—pitfalls and solutions is reported by Harris, C. L., et al. (J. Immunol. Meth. 268 (2002) 245-258). Zhu, Y., et al. report multigene lentiviral plasmids based on differential splicing and translational control (Mol. Ther. 4 (2001) 375-382).

Fallot, S., et al. disclosed alternative-splicing-based bicistronic vectors for ratio-controlled protein expression and application to recombinant antibody production (Nucl. Acids Res. 37 (2009) e134-e134). Wang, Z., et al. disclosed with respect to splicing regulation from a parts list of regulatory elements to an integrated splicing code (RNA 14 (2008) 802-813). Cartegni, L., reported about ESEfinder, which is a web resource to identify exonic splicing enhancers (Nucl. Acids. Res. 31 (2003) 3568-3571). WO 2013/092720 discloses a method of selecting a cell expressing a bispecific antibody comprising the steps of (a) generating a population of eukaryotic cells by transduction with a population of lentiviral virus particles, whereby each cell of the population of cells displays a membrane-bound full length antibody which is encoded by the lentiviral nucleic acid, and which specifically binds to two or more antigens or two or more epitopes on the same antigen, and (b) selecting from the population of eukaryotic cells a cell depending on the properties of the displayed membrane-bound full length antibody, whereby each lentiviral virus particle of the population of lentiviral virus particles comprises a bicistronic expression cassette comprising the EV71-IRES for the expression of the membrane-bound antibody.

In WO 2007/131774 is reported a nucleic acid comprising in 5' to 3' direction a first nucleic acid encoding a heterologous polypeptide without an in frame translational stop codon, a second nucleic acid beginning with a 5' splice donor site and terminated by a 3' splice acceptor site comprising an in frame translational stop codon and a polyadenylation signal, and a third nucleic acid encoding at least a fragment of a transmembrane domain, or a signal peptide for a GPI-anchor.

SUMMARY OF THE INVENTION

The invention is based at least in part on the finding that specific modifications in the alternative splice acceptor site (3'-splice site region) can be used to regulate the splicing ratio in an alternatively spliced nucleic acid. These modifications can be made to adopt, e.g., the expression of a marker, i.e. the polypeptide of interest comprising the transmembrane domain at its C-terminus (i.e. the longer construct), to the used cell line.

One aspect as reported herein is a nucleic acid that has the nucleotide sequence TGACCACGCCAATCGTGTCCAG (SEQ ID NO: 14).

One aspect as reported herein is a nucleic acid that has the nucleotide sequence TGACCACGCCAATCGTGTCCAGAGCTG (SEQ ID NO: 15).

One aspect as reported herein is a nucleic acid comprising in 5' to 3' direction
i) a first nucleic acid fragment encoding a polypeptide of interest without an in frame translational stop codon,
ii) a second nucleic acid fragment operably linked to said first nucleic acid fragment, which is beginning with the 5' splice donor site of an immunoglobulin heavy chain CH3 or CH4 domain and which is terminated by the 3' splice acceptor site of the succeeding immunoglobulin heavy chain transmembrane domain exon M1 and which comprises in frame translational stop codon and a polyadenylation signal, iii) a third nucleic acid fragment operably linked to said second nucleic acid encoding at least a fragment of a transmembrane domain, wherein the second nucleic acid fragment has at its 3' terminus the nucleotide sequence TGACCACGC-CAATCGTGTCCAG (SEQ ID NO: 14).

One aspect as reported herein is a nucleic acid comprising in 5' to 3' direction i) a first nucleic acid fragment encoding a polypeptide of interest without an in frame translational stop codon, ii) a second nucleic acid fragment operably linked to said first nucleic acid fragment, which is beginning with the 5' splice donor site of an immunoglobulin heavy chain CH3 or CH4 domain and which is terminated by the 3' splice acceptor site of the succeeding immunoglobulin heavy chain transmembrane domain exon M1 and which comprises in frame translational stop codon and a polyadenylation signal, iii) a third nucleic acid fragment operably linked to said second nucleic acid encoding at least a fragment of a transmembrane domain, wherein the nucleotide sequence TGACCACGC-CAATCGTGTCCAGAGCTG (SEQ ID NO: 15) overlaps the second nucleic acid fragment and the third nucleic acid fragment.

In one embodiment the polypeptide of interest is an immunoglobulin heavy chain.

In one embodiment the nucleic acid is comprised in an expression cassette.

In one embodiment the second nucleic acid fragment comprises only one 5' splice donor site and only one 3' splice acceptor site.

In one embodiment the second nucleic acid fragment is a naturally occurring immunoglobulin heavy chain intron, which is following the exon encoding an immunoglobulin heavy chain CH3 or CH4 domain, wherein in said intron at least 50 consecutive nucleotides are deleted.

In one embodiment the first nucleic acid fragment encodes an immunoglobulin heavy chain and comprises all exons and all but one intron of the genomically organized immunoglobulin heavy chain gene.

In one embodiment the third nucleic acid fragment encodes a fragment of a transmembrane domain, whereby the fragment of the transmembrane domain is encoded by a single exon.

In one embodiment the transmembrane domain an immunoglobulin transmembrane domain that is encoded by an M1-M2-exon-fusion (a single exon without the genomically intervening intron).

In one embodiment the second nucleic acid fragment has the nucleotide sequence of SEQ ID NO: 11.

In one embodiment the third nucleic acid fragment has the nucleotide sequence of SEQ ID NO: 12.

One aspect as reported herein is the use of a nucleic acid as reported herein for selecting stably transfected cells.

One aspect as reported herein is a method for selecting a eukaryotic cell expressing an immunoglobulin, whereby the method comprises a) transfecting a eukaryotic cell with one or more nucleic acids comprising a first expression cassette for an immunoglobulin light chain and a second expression cassette for an immunoglobulin heavy chain, which is comprising a nucleic acid as reported herein, b) culturing said transfected cell under conditions suitable for the production of pre-mRNA from said nucleic acid, processing of said pre-mRNA, and translation of the processed mRNA into an immunoglobulin heavy chain, wherein said transfected cell produces soluble immunoglobulin and plasma-membrane-bound immunoglobulin by alternative splicing of said pre-mRNA, and c) selecting a cell with plasma-membrane-bound immunoglobulin to be said cell expressing an immunoglobulin.

One aspect as reported herein is a cell comprising a nucleic acid with the nucleotide sequence of SEQ ID NO: 14 or SEQ ID NO: 15.

In one embodiment the cell comprises a nucleic acid comprising in 5' to 3' direction i) a first nucleic acid fragment encoding an immunoglobulin heavy chain without an in frame translational stop codon, ii) a second nucleic acid fragment operably linked to said first nucleic acid fragment, which is beginning with the 5' splice donor site of an immunoglobulin heavy chain CH3 or CH4 domain and which is terminated by the 3' splice acceptor site of the succeeding immunoglobulin heavy chain transmembrane domain exon M1 and which comprises in frame translational stop codon and a polyadenylation signal, iii) a third nucleic acid fragment operably linked to said second nucleic acid encoding at least a fragment of a transmembrane domain, wherein the nucleotide sequence CTACCACGC-CAATCGTGTCCAGAGCTG (SEQ ID NO: 15) overlaps the second nucleic acid fragment and the third nucleic acid fragment.

One aspect as reported herein is a method for producing an immunoglobulin comprising the following steps:

cultivating a cell comprising a nucleic acid with the nucleotide sequence of SEQ ID NO: 14 or SEQ ID NO: 15, recovering from the cell or the cultivation medium the immunoglobulin, optionally purifying the immunoglobulin with one or more chromatography steps, and thereby producing an immunoglobulin.

In one embodiment the cell comprises a nucleic acid comprising in 5' to 3' direction i) a first nucleic acid fragment encoding an immunoglobulin heavy chain without an in frame translational stop codon, ii) a second nucleic acid fragment operably linked to said first nucleic acid fragment, which is beginning with the 5' splice donor site of an immunoglobulin heavy chain CH3 or CH4 domain and which is terminated by the 3' splice acceptor site of the succeeding immunoglobulin heavy chain transmembrane domain exon M1 and which comprises in frame translational stop codon and a polyadenylation signal, iii) a third nucleic acid fragment operably linked to said second nucleic acid encoding at least a fragment of a transmembrane domain, wherein the nucleotide sequence CTACCACGC-CAATCGTGTCCAGAGCTG (SEQ ID NO: 15) overlaps the second nucleic acid fragment and the third nucleic acid fragment.

In one embodiment of all aspects the cell is a CHO cell.

One aspect as reported herein is a splice acceptor site nucleic acid that has the nucleotide sequence CTAC-CACCCCCTTCCTGTCCAG (SEQ ID NO: 29).

One aspect as reported herein is a nucleic acid that has the nucleotide sequence CTACCACCCCTTCCTGTCCAGAGCTG (SEQ ID NO: 30).

One aspect as reported herein is a nucleic acid comprising in 5' to 3' direction
  i) a first nucleic acid fragment encoding a polypeptide of interest without an in frame translational stop codon,
  ii) a second nucleic acid fragment operably linked to said first nucleic acid fragment, which is beginning with the 5' splice donor site of an immunoglobulin heavy chain CH3 or CH4 domain and which is terminated by the 3' splice acceptor site of the succeeding immunoglobulin heavy chain transmembrane domain exon M1 and which comprises in frame translational stop codon and a polyadenylation signal,
  iii) a third nucleic acid fragment operably linked to said second nucleic acid encoding at least a fragment of a transmembrane domain,
  wherein the second nucleic acid fragment has at its 3' terminus the nucleotide sequence CTACCACCCCTTCCTGTCCAG (SEQ ID NO: 29).

One aspect as reported herein is a nucleic acid comprising in 5' to 3' direction
  i) a first nucleic acid fragment encoding a polypeptide of interest without an in frame translational stop codon,
  ii) a second nucleic acid fragment operably linked to said first nucleic acid fragment, which is beginning with the 5' splice donor site of an immunoglobulin heavy chain CH3 or CH4 domain and which is terminated by the 3' splice acceptor site of the succeeding immunoglobulin heavy chain transmembrane domain exon M1 and which comprises in frame translational stop codon and a polyadenylation signal,
  iii) a third nucleic acid fragment operably linked to said second nucleic acid encoding at least a fragment of a transmembrane domain,
  wherein the nucleotide sequence CTACCACCCCTTCCTGTCCAGAGCTG (SEQ ID NO: 30) overlaps the second nucleic acid fragment and the third nucleic acid fragment.

In one embodiment the polypeptide of interest is an immunoglobulin heavy chain.

In one embodiment the nucleic acid is comprised in an expression cassette.

In one embodiment the second nucleic acid fragment comprises only one 5' splice donor site and only one 3' splice acceptor site.

In one embodiment the second nucleic acid fragment is a naturally occurring immunoglobulin heavy chain intron, which is following the exon encoding an immunoglobulin heavy chain CH3 or CH4 domain, wherein in said intron at least 50 consecutive nucleotides are deleted.

In one embodiment the first nucleic acid fragment encodes an immunoglobulin heavy chain and comprises all exons and all but one intron of the genomically organized immunoglobulin heavy chain gene.

In one embodiment the third nucleic acid fragment encodes a fragment of a transmembrane domain, whereby the fragment of the transmembrane domain is encoded by a single exon.

In one embodiment the transmembrane domain an immunoglobulin transmembrane domain that is encoded by an M1-M2-exon-fusion (a single exon without the genomically intervening intron).

One aspect as reported herein is the use of a nucleic acid as reported herein for selecting stably transfected cells.

One aspect as reported herein is a method for selecting a eukaryotic cell expressing an immunoglobulin, whereby the method comprises
  a) transfecting a eukaryotic cell with one or more nucleic acids comprising a first expression cassette for an immunoglobulin light chain and a second expression cassette for an immunoglobulin heavy chain comprising a nucleic acid as reported herein,
  b) culturing of said transfected cell under conditions suitable for the production of pre-mRNA from said nucleic acid, processing of said pre-mRNA, and translation of said processed mRNA into an immunoglobulin heavy chain, wherein said transfected cell produces soluble immunoglobulin and plasma-membrane-bound immunoglobulin by alternative splicing of said pre-mRNA, and
  c) selecting a cell with plasma-membrane-bound immunoglobulin to be said cell expressing an immunoglobulin.

One aspect as reported herein is a cell comprising a nucleic acid with the nucleotide sequence of SEQ ID NO: 29 or SEQ ID NO: 30.

In one embodiment the cell comprises a nucleic acid comprising in 5' to 3' direction
  i) a first nucleic acid fragment encoding an immunoglobulin heavy chain without an in frame translational stop codon,
  ii) a second nucleic acid fragment operably linked to said first nucleic acid fragment, which is beginning with the 5' splice donor site of an immunoglobulin heavy chain CH3 or CH4 domain and which is terminated by the 3' splice acceptor site of the succeeding immunoglobulin heavy chain transmembrane domain exon M1 and which comprises in frame translational stop codon and a polyadenylation signal,
  iii) a third nucleic acid fragment operably linked to said second nucleic acid encoding at least a fragment of a transmembrane domain,
  wherein the nucleotide sequence CTACCACGCAATCGTGTCCAGAGCTG (SEQ ID NO: 30) overlaps the second nucleic acid fragment and the third nucleic acid fragment.

One aspect as reported herein is a method for producing an immunoglobulin comprising the following steps:
  cultivating a cell comprising a nucleic acid with the nucleotide sequence of SEQ ID NO: 29 or SEQ ID NO: 30,
  recovering from the cell or the cultivation medium the immunoglobulin,
  optionally purifying the immunoglobulin with one or more chromatography steps,
  and thereby producing an immunoglobulin.

In one embodiment the cell comprises a nucleic acid comprising in 5' to 3' direction
  i) a first nucleic acid fragment encoding an immunoglobulin heavy chain without an in frame translational stop codon,
  ii) a second nucleic acid fragment operably linked to said first nucleic acid fragment, which is beginning with the 5' splice donor site of an immunoglobulin heavy chain CH3 or CH4 domain and which is terminated by the 3' splice acceptor site of the succeeding immunoglobulin heavy chain transmembrane domain exon M1 and which comprises in frame translational stop codon and a polyadenylation signal, iii) a third nucleic acid fragment operably linked to said second nucleic acid encoding at least a fragment of a transmembrane domain, wherein the nucleotide sequence CTACCACGCCAATCGTGTCCAGAGCTG (SEQ ID NO: 30) overlaps the second nucleic acid fragment and the third nucleic acid fragment.

In one embodiment of all aspects the cell is a CHO cell.

One aspect as reported herein is a nucleic acid that has the nucleotide sequence CTACCACGCCAATCGTGTCCAG (SEQ ID NO: 31).

One aspect as reported herein is a nucleic acid that has the nucleotide sequence CTACCACGCCAATCGTGTCCAGAGCTG (SEQ ID NO: 32).

One aspect as reported herein is a nucleic acid comprising in 5' to 3' direction
i) a first nucleic acid fragment encoding a polypeptide of interest without an in frame translational stop codon,
ii) a second nucleic acid fragment operably linked to said first nucleic acid fragment, which is beginning with the 5' splice donor site of an immunoglobulin heavy chain CH3 or CH4 domain and which is terminated by the 3' splice acceptor site of the succeeding immunoglobulin heavy chain transmembrane domain exon M1 and which comprises in frame translational stop codon and a polyadenylation signal,
iii) a third nucleic acid fragment operably linked to said second nucleic acid encoding at least a fragment of a transmembrane domain,
wherein the second nucleic acid fragment has at its 3' terminus the nucleotide sequence CTACCACGCCAATCGTGTCCAG (SEQ ID NO: 31).

One aspect as reported herein is a nucleic acid comprising in 5' to 3' direction
i) a first nucleic acid fragment encoding a polypeptide of interest without an in frame translational stop codon,
ii) a second nucleic acid fragment operably linked to said first nucleic acid fragment, which is beginning with the 5' splice donor site of an immunoglobulin heavy chain CH3 or CH4 domain and which is terminated by the 3' splice acceptor site of the succeeding immunoglobulin heavy chain transmembrane domain exon M1 and which comprises in frame translational stop codon and a polyadenylation signal,
iii) a third nucleic acid fragment operably linked to said second nucleic acid encoding at least a fragment of a transmembrane domain,
wherein the nucleotide sequence CTACCACGCCAATCGTGTCCAGAGCTG (SEQ ID NO: 32) overlaps the second nucleic acid fragment and the third nucleic acid fragment.

In one embodiment the polypeptide of interest is an immunoglobulin heavy chain.

In one embodiment the nucleic acid is comprised in an expression cassette.

In one embodiment the second nucleic acid fragment comprises only one 5' splice donor site and only one 3' splice acceptor site.

In one embodiment the second nucleic acid fragment is a naturally occurring immunoglobulin heavy chain intron, which is following the exon encoding an immunoglobulin heavy chain CH3 or CH4 domain, wherein in said intron at least 50 consecutive nucleotides are deleted.

In one embodiment the first nucleic acid fragment encodes an immunoglobulin heavy chain and comprises all exons and all but one intron of the genomically organized immunoglobulin heavy chain gene.

In one embodiment the third nucleic acid fragment encodes a fragment of a transmembrane domain, whereby the fragment of the transmembrane domain is encoded by a single exon.

In one embodiment the transmembrane domain an immunoglobulin transmembrane domain that is encoded by an M1-M2-exon-fusion (a single exon without the genomically intervening intron).

One aspect as reported herein is the use of a nucleic acid as reported herein for selecting stably transfected cells.

One aspect as reported herein is a method for selecting a eukaryotic cell expressing an immunoglobulin, whereby the method comprises
a) transfecting a eukaryotic cell with one or more nucleic acids comprising a first expression cassette for an immunoglobulin light chain and a second expression cassette for an immunoglobulin heavy chain comprising a nucleic acid as reported herein,
b) culturing of said transfected cell under conditions suitable for the production of pre-mRNA from said nucleic acid, processing of said pre-mRNA, and translation of said processed mRNA into an immunoglobulin heavy chain, wherein said transfected cell produces soluble immunoglobulin and plasma-membrane-bound immunoglobulin by alternative splicing of said pre-mRNA, and
c) selecting a cell with plasma-membrane-bound immunoglobulin to be said cell expressing an immunoglobulin.

One aspect as reported herein is a cell comprising a nucleic acid with the nucleotide sequence of SEQ ID NO: 31 or SEQ ID NO: 32.

In one embodiment the cell comprises a nucleic acid comprising in 5' to 3' direction
i) a first nucleic acid fragment encoding an immunoglobulin heavy chain without an in frame translational stop codon,
ii) a second nucleic acid fragment operably linked to said first nucleic acid fragment, which is beginning with the 5' splice donor site of an immunoglobulin heavy chain CH3 or CH4 domain and which is terminated by the 3' splice acceptor site of the succeeding immunoglobulin heavy chain transmembrane domain exon M1 and which comprises in frame translational stop codon and a polyadenylation signal,
iii) a third nucleic acid fragment operably linked to said second nucleic acid encoding at least a fragment of a transmembrane domain,
wherein the nucleotide sequence CTACCACGCCAATCGTGTCCAGAGCTG (SEQ ID NO: 32) overlaps the second nucleic acid fragment and the third nucleic acid fragment.

One aspect as reported herein is a method for producing an immunoglobulin comprising the following steps:
cultivating a cell comprising a nucleic acid with the nucleotide sequence of SEQ ID NO: 31 or SEQ ID NO: 32,
recovering from the cell or the cultivation medium the immunoglobulin,
optionally purifying the immunoglobulin with one or more chromatography steps,
and thereby producing an immunoglobulin.

In one embodiment the cell comprises a nucleic acid comprising in 5' to 3' direction
i) a first nucleic acid fragment encoding an immunoglobulin heavy chain without an in frame translational stop codon, ii) a second nucleic acid fragment operably linked to said first nucleic acid fragment, which is beginning with the 5' splice donor site of an immunoglobulin heavy chain CH3 or CH4 domain and which is terminated by the 3' splice acceptor site of the succeeding immunoglobulin heavy chain transmembrane domain exon M1 and which comprises in frame translational stop codon and a polyadenylation signal, iii) a third nucleic acid fragment operably linked to said second nucleic acid encoding at least a fragment of a transmembrane domain, wherein the nucleotide sequence CTACCACGCCAATCGTGTCCAGAGCTG (SEQ ID NO: 32) overlaps the second nucleic acid fragment and the third nucleic acid fragment.

In one embodiment of all aspects the cell is a CHO cell.

DESCRIPTION OF THE FIGURES

FIG. 2A: Autoradiography of a Northern blot hybridized with [a-32P] labeled probe 1 (lanes 1-8) or probe 2 (lanes 9-16). In each lane 10 μg total RNA isolated from a stably transfected pool (lanes 1-7 and 9-15) or from non-transfected CHO-K 1 cells (lanes 8 and 16) was separated by denaturing agarose gel electrophoresis and transferred to a nylon membrane.
FIG. 2B: Schematic depiction of the two mRNA isoforms encoding the heavy chain of mIgG or sIgG. The exons are represented by boxes. The regions complementary to the probes 1 and 2 are marked with black bars.
FIG. 9A: The viable cell density was measured with a CASY cell counter.
FIG. 9B: The IgG concentration in the cell culture supernatants was determined by ELISA.
FIG. 10A: Scheme of the workflow of the transfection of clone 1D5 with plasmid pmIgG-Puro-mut-p(Y) and performing the mIgG-puromycin selection process as described in Example 6.
FIG. 10B: The workflow of the standard approach is shown as described in detail in Example 6.
FIG. 11A: First fed batch assay with 39 clones generated with the mIgG-puromycin selection system. The clones marked with asterisks were selected for further assessment.
FIG. 11B: Fed batch assay with seven selected mIgG-puromycin generated clones (I, left part), and 7 top clones from the standard selection approach (II, center). The results of the parental cell line 1D5 in assay I, II and two retests are depicted in grey. The dashed column on the right represents the average titer of the four 1D5 runs; the standard deviation is depicted as error bar.

DETAILED DESCRIPTION OF THE INVENTION

Figure 1:
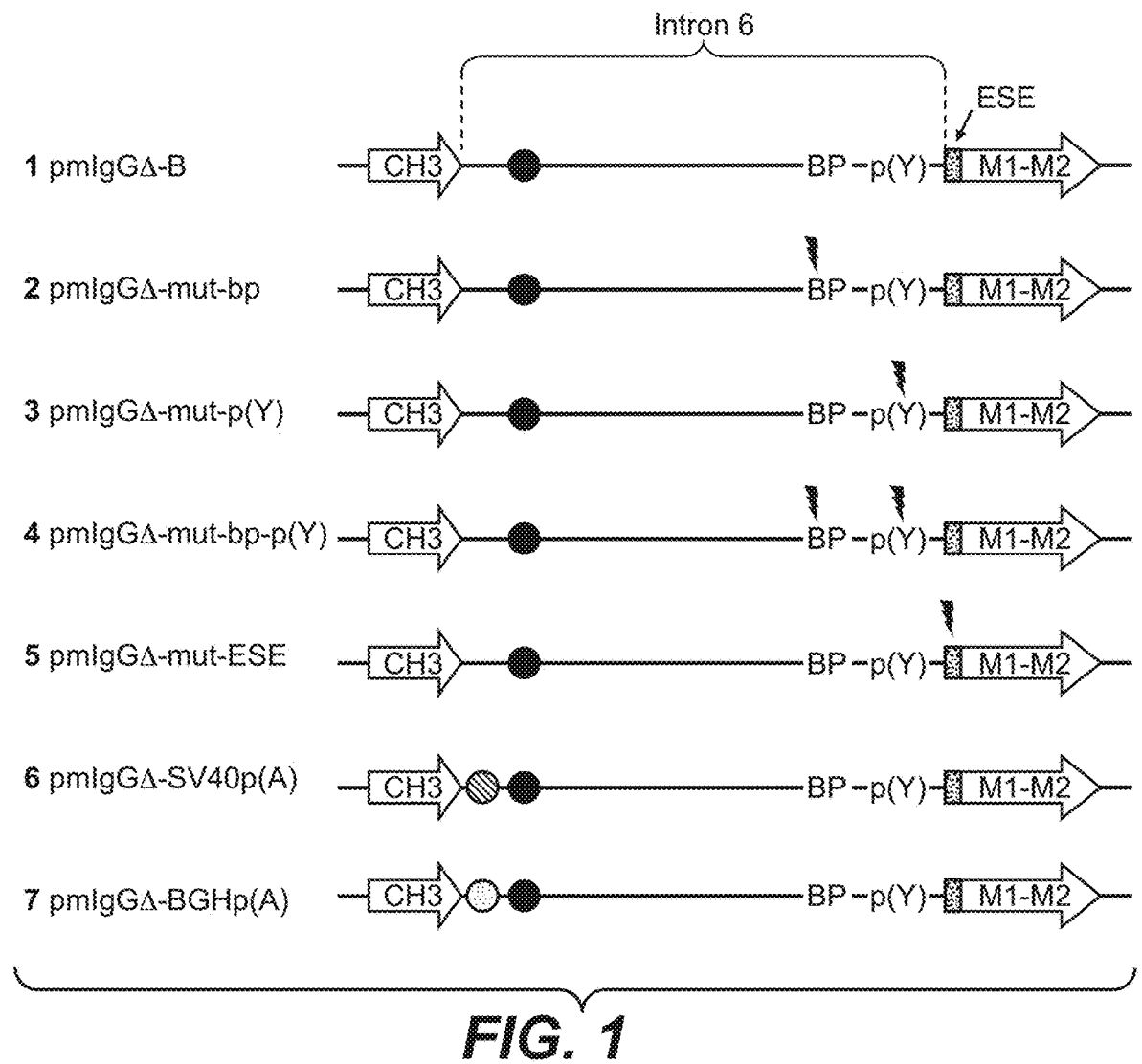
FIG. 1: Overview of modified intron 6 region constructs. The Figure schematically shows the genomic organization of the heavy chain between the exons CH3 and M1-M2 from plasmid pmIgGA-B (1) and the modified constructs (2-7). The positions of point mutations are shown by black lightning symbols. The polyadenylation (p(A)) site after CH3 is depicted as a black filled circle, the added p(A) site from SV40 or BGH as striped or grey filled circle, respectively. The size and position of the depicted elements is not to scale. BP: branch point; p(Y): polypyrimidine tract; ESE: exonic splice enhancer.

Useful methods and techniques for carrying out the current invention are described in e.g. Ausubel, F. M. (ed.), Current Protocols in Molecular Biology, Volumes I to III (1997); Glover, N. D., and Hames, B. D., ed., DNA Cloning: A Practical Approach, Volumes I and II (1985), Oxford University Press; Freshney, R. I. (ed.), Animal Cell Culture—a practical approach, IRL Press Limited (1986); Watson, J. D., et al., Recombinant DNA, Second Edition, CHSL Press (1992); Winnacker, E. L., From Genes to Clones; N.Y., VCH Publishers (1987); Celis, J., ed., Cell Biology, Second Edition, Academic Press (1998); Freshney, R. I., Culture of Animal Cells: A Manual of Basic Technique, second edition, Alan R. Liss, Inc., N.Y. (1987).

The use of recombinant DNA technology enables the generation derivatives of a nucleic acid. Such derivatives can, for example, be modified in individual or several nucleotide positions by substitution, alteration, exchange, deletion or insertion. The modification or derivatization can, for example, be carried out by means of site directed mutagenesis. Such modifications can easily be carried out by a person skilled in the art (see e.g. Sambrook, J., et al., Molecular Cloning: A laboratory manual (1999) Cold Spring Harbor Laboratory Press, New York, USA; Hames, B. D., and Higgins, S. G., Nucleic acid hybridization—a practical approach (1985) IRL Press, Oxford, England).

Definitions

A "nucleic acid" as used herein, denotes a polynucleotide molecule, for example DNA. This polynucleotide molecule can be a naturally occurring polynucleotide molecule or a synthetic polynucleotide molecule or a combination of one or more naturally occurring polynucleotide molecules or fragments thereof with one or more synthetic polynucleotide molecules. Also encompassed by this definition are naturally occurring polynucleotide molecules in which one or more nucleotides have been changed, e.g. by mutagenesis, deleted or added. The nucleic acid can either be isolated, or integrated in another nucleic acid, e.g. in an expression plasmid or the chromosome of a eukaryotic host cell. A nucleic acid is likewise characterized by its nucleotide sequence. It is known in the art to deduce an amino acid sequence from the corresponding encoding nucleic acid and likewise to derive a corresponding nucleic acid from the encoded amino acid sequence. Thus, an amino acid sequence is likewise characterized by its nucleic acid. Likewise is a nucleic acid given by a corresponding amino acid sequence.

The term "plasmid" as used within this application includes shuttle and expression plasmids as well as transfection plasmids. Typically, the plasmid will also comprise an origin of replication (e.g. the ColE1 and oriP origin of replication) and a selectable marker (e.g. an ampicillin, puromycin, neomycin or tetracycline resistance gene) for replication and selection, respectively, of the plasmid in prokaryotic cells.

An "expression cassette" denotes a construct that contains the necessary regulatory elements for expression of at least the contained structural gene in a cell. Optionally additional elements can be contained which enable the secretion of the expressed polypeptide or protein. Generally an expression cassette comprises a promoter, the structural gene and a polyadenylation site.

A "gene" denotes a segment e.g. on a chromosome or on a plasmid, which is necessary for the expression of a polypeptide or protein. Beside the coding region the gene comprises other functional elements including a promoter, one or more introns and/or exons, and one or more terminators.

The term "structural gene" denotes the coding region of a gene, i.e. the exons, without a signal sequence, but with intervening introns.

A "selectable marker" denotes a gene that allows cells carrying the gene to be specifically selected for or against, in the presence or absence of a corresponding selection agent. A useful positive selectable marker is an antibiotic resistance gene. This selectable marker allows cells transformed with the gene to be positively selected for in the presence of the corresponding antibiotic; a non-transformed cell would not be capable to grow or survive under the selective culture conditions, i.e. in the presence of the selection agent, in a selective medium. Selectable markers can be positive, negative or bifunctional. Positive selectable markers allow selection for cells carrying the marker, whereas negative selectable markers allow cells carrying the marker to be selectively eliminated. Typically, a selectable marker will confer resistance to a drug or compensate for a metabolic or catabolic defect in the host cell. Selectable markers useful with eukaryotic cells include, e.g., the genes for aminoglycoside phosphotransferase (APH), such as the hygromycin phosphotransferase (hyg), neomycin and G418 APH, dihydrofolate reductase (DHFR), thymidine kinase (tk), glutamine synthetase (GS), asparagine synthetase, tryptophan synthetase (selective agent indole), histidinol dehydrogenase (selective agent histidinol D), and genes encoding resistance to puromycin, neomycin, bleomycin, phleomycin, chloramphenicol, Zeocin, and mycophenolic acid. Further selectable marker genes are described in WO 92/08796 and WO 94/28143.

The term "regulatory elements" denotes nucleotide sequences present in cis or/and trans, necessary for transcription and/or translation of the structural gene of interest. The transcriptional regulatory elements normally comprise a promoter, transcriptional initiation and termination sites, and a polyadenylation signal sequence. The term "transcriptional initiation site" refers to the nucleotide corresponding to the first nucleic acid to be incorporated into the primary transcript, i.e. the pre-mRNA; the transcriptional initiation site may overlap with the promoter sequence. The term "transcriptional termination site" refers to a nucleotide sequence normally present at the 3' end of a structural gene of interest to be transcribed, that causes RNA polymerase to terminate transcription. The polyadenylation signal sequence, or poly-A addition signal (p(A)) provides the signal for the cleavage at a specific site at the 3' end of a eukaryotic mRNA and the post-transcriptional addition of a sequence of about 100-200 adenine nucleotides (polyA tail) to the cleaved 3' end in the nucleus. The polyadenylation signal sequence may include the consensus sequence AATAAA located at about 10-30 nucleotides upstream from the site of cleavage. Translational regulatory elements include a translational initiation (AUG) and stop codon (TAA, TAG or TGA).

A "promoter" refers to a polynucleotide sequence that controls transcription of a gene or nucleic acid sequence to which it is operably linked. A promoter includes signals for RNA polymerase binding and transcription initiation. The promoter used will be functional in the cell type of the cell in which expression of the selected/operably linked sequence is contemplated. A large number of promoters including constitutive, inducible and repressible promoters from a variety of different sources, are well known in the art (and identified in databases such as GenBank) and are available as or within cloned polynucleotides (from, e.g., depositories such as ATCC as well as other commercial or individual sources). A "promoter" comprises a nucleotide sequence that directs the transcription of a structural gene. Typically, a promoter is located in the 5' non-coding or untranslated region of a gene, proximal to the transcriptional start site of a structural gene. Sequence elements within promoters that function in the initiation of transcription are often characterized by consensus nucleotide sequences. These promoter elements include RNA polymerase binding sites, TATA sequences, CAAT sequences, differentiation-specific elements (DSEs; McGehee, R. E. Jr., et al., Mol. Endocrinol. 7 (1993) 551-60), cyclic AMP response elements (CREs), serum response elements (SREs; Treisman, R., Seminars in Cancer Biol. 1 (1990) 47-58), glucocorticoid response elements (GREs), and binding sites for other transcription factors, such as CRE/ATF (O'Reilly, M. A., et al., J. Biol. Chem. 267 (1992) 19938-43), AP2 (Ye, J., et al., J. Biol. Chem. 269 (1994) 25728-34), SP1, cAMP response element binding protein (CREB; Loeken, M. R., Gene Expr. 3 (1993) 253-64) and octamer factors (see, in general, Watson et al., eds., Molecular Biology of the Gene, 4th ed., The Benjamin/Cummings Publishing Company, Inc. (1987), and Lemaigre, F. P. and Rousseau, G. G., Biochem. J. 303 (1994) 1-14). If a promoter is an inducible promoter, then the rate of transcription increases in response to an inducing agent. In contrast, the rate of transcription is not regulated by an inducing agent if the promoter is a constitutive promoter. Repressible promoters are also known. For example, the c-fos promoter is specifically activated upon binding of growth hormone to its receptor on the cell surface. Tetracycline (Tet) regulated expression can be achieved by artificial hybrid promoters that consist e.g. of a CMV promoter followed by two Tet-operator sites. The Tet-repressor binds to the two Tet-operator sites and blocks transcription. Upon addition of the inducer tetracycline, the Tet-repressor is released from the Tet-operator sites and transcription proceeds (Gossen, M. and Bujard, H. Proc. Natl. Acad. Sci. USA 89 (1992) 5547-5551). For other inducible promoters including metallothionein and heat shock promoters, see, e.g., Sambrook et al. (supra) and Gossen et al., Curr. Opin. Biotech. 5 (1994) 516-520. Among the eukaryotic promoters that have been identified as strong promoters for high-level expression are the SV40 early promoter, adenovirus major late promoter, mouse metallothionein-I promoter, Rous sarcoma virus long terminal repeat, Chinese hamster elongation factor 1 alpha (CHEF-1, see e.g. U.S. Pat. No. 5,888,809), human EF-1 alpha, ubiquitin, and human cytomegalovirus immediate early promoter (CMV IE).

The promoter can be constitutive or inducible as outlined above. An enhancer (i.e. a cis-acting DNA element that acts on a promoter to increase transcription) may be necessary to function in conjunction with the promoter to increase the level of expression obtained with the promoter alone, and may be included as a transcriptional regulatory element. Often, the polynucleotide segment containing the promoter will include enhancer sequences as well (e.g. CMV or SV40).

"Operably linked" refers to a juxtaposition of two or more components, wherein the components so described are in a relationship permitting them to function in their intended manner. For example, a promoter and/or enhancer are operably linked to a coding sequence, if they act in cis to control or modulate the transcription of the linked coding sequence. Generally, but not necessarily, the DNA sequences that are "operably linked" are contiguous and, where necessary to join two protein encoding regions such as a secretory leader and a polypeptide, or a polypeptide and a transmembrane domain, or a polypeptide and a signal peptide for a GPI-anchor, or a polypeptide and a translational stop codon, contiguous and in reading frame. However, although an operably linked promoter is generally located upstream of the coding sequence, it is not necessarily contiguous with it. Enhancers do not have to be contiguous. An enhancer is operably linked to a coding sequence if the enhancer increases transcription of the coding sequence. Operably linked enhancers can be located upstream, within or downstream of coding sequences and at considerable distance from the promoter. A polyadenylation site is operably linked to a coding sequence if it is located at the downstream end of the coding sequence such that transcription proceeds through the coding sequence into the polyadenylation sequence. Linking is accomplished by recombinant methods known in the art, e.g., using PCR methodology and/or by ligation at convenient restriction sites. If convenient restriction sites do not exist, then synthetic oligonucleotide adaptors or linkers are used in accord with conventional practice.

The term "production of pre-mRNA" as used herein denotes a process of transcription of DNA into its complementary pre-mRNA. Eukaryotic DNA is composed of coding and non-coding regions, which are referred to as exons (coding) and introns (non-coding). In the transcription process of DNA into its complementary pre-mRNA the genomic organization of exons and introns is maintained.

The term "processing of pre-mRNA" as used herein denotes a post-transcriptional modification process. In this step, the introns of the pre-mRNA are spliced out, i.e. removed from the pre-mRNA, the 5' end of the processed mRNA is capped and 3' polyadenylation is performed. The final nuclear, i.e. mature, mRNA is obtained in this step.

The term "transmembrane domain" as used within this application denotes a polypeptide or protein which is encoded on the DNA level by at least one exon and which comprises an extracellular, a transmembrane, and an intracellular region. A transmembrane domain generally comprises three distinct structural regions: an extracellular region, a central conserved transmembrane stretch, and a cytoplasmatic region. The extracellular domain can be at the N-terminus or at the C-terminus of the transmembrane domain and likewise the cytoplasmic region is at the respective other terminus. In one embodiment the transmembrane domain comprises in N- to C-terminal direction an extracellular region and a transmembrane region. The transmembrane domain may additionally comprise an intracellular or cytoplasmatic region.

The term "a fragment of a transmembrane domain" as used within this application denotes the part of a transmembrane domain that spans the cell membrane, i.e. which is located within the cell membrane, i.e. the transmembrane stretch. This fragment of a transmembrane domain is functional with respect to the incorporation into a cell membrane. Thus, "a fragment of a transmembrane domain" as used herein denotes transmembrane domains of any origin, such as e.g. full length wild-type domains, including variants or truncated or extended forms thereof, as long as these can excert the function of incorporation into a cell membrane. Therefore, in one embodiment a fragment of a transmembrane domain is an amino acid sequence that integrates into a cell membrane. In one embodiment a fragment of a transmembrane domain is a truncated and/or mutated variant of a wild-type transmembrane domain. In one embodiment the variant is capable of integrating into a cell membrane. In one embodiment the wild-type transmembrane domain is a wild-type immunoglobulin transmembrane domain.

The term "alternatively spliceable nucleic acid" denotes a nucleic acid beginning with a 5' splice donor site and terminated by a 3' splice acceptor site. This nucleic acid contains a translational stop codon and a polyadenylation signal. This alternatively spliceable nucleic acid comprises a non-coding region which is not constitutively spliced out of the corresponding pre-mRNA, such as, for example, the intron after the exon encoding an immunoglobulin heavy chain $C_H3$ or $C_H4$ domain. The "alternative splicing event" taking place at the 5' splice donor site of the alternatively spliceable nucleic acid is a decision event whether the alternatively spliceable nucleic acid is spliced out of the pre-mRNA or if it is at least partially maintained and comprised in the mature (processed) mRNA.

The term "alternative splicing" and grammatical equivalents thereof as used herein refers to a process in eukaryotic cells in which from a single pre-mRNA due to different processing/splicing of one or more introns different mature mRNAs can be obtained and accordingly different isoforms of a polypeptide can be expressed. In one embodiment of the invention a single, i.e. only one, intron of the produced pre-mRNA can be spliced alternatively. In another embodiment the second nucleic acid can be spliced alternatively. In a further embodiment comprises the second nucleic acid an alternatively spliceable intron. The different processing is a "yes/no" decision, i.e. in the alternative splicing process the intron to be processed, i.e. the "alternatively spliceable nucleic acid", is either at least partially retained or spliced out. This has not to be understood as a branching point mechanism resulting in different exons to follow. It is in fact a mechanism in which an alternatively spliceable nucleic acid is either spliced out or at least partially maintained in the mature mRNA. With this mechanism the alternatively spliceable nucleic acid and, thus, the therein comprised in frame translational stop codon are either retained or removed.

Alternative splicing is an important regulatory mechanism in eukaryotic cells. With alternative splicing different combinations of exons in a mature mRNA can be obtained from the same pre-mRNA giving rise to a plurality of different proteins encoded by the same DNA.

The term "expression" as used herein refers to transcription and/or translation processes occurring within a cell. The level of transcription of a desired product in a cell can be determined on the basis of the amount of corresponding mRNA that is present in the cell. For example, mRNA transcribed from a selected sequence can be quantitated by PCR or by Northern hybridization (see Sambrook et al., Molecular Cloning: A Laboratory Manual, Cold Spring Harbor Laboratory Press (1989)). Polypeptides can be quantitated by various methods, e.g. by ELISA, by assaying for the biological activity of the polypeptide, or by employing assays that are independent of such activity, such as Western blotting, SDS polyacrylamide gel electrophoresis, NMR or radioimmunoassay, e.g. by using antibodies that recognize and bind to the polypeptide (see Sambrook et al., 1989, supra).

The term "cell" includes both prokaryotic cells, which are used for propagation of plasmids, as well as eukaryotic cells, which are used for the expression of the heterologous nucleic acid. In one embodiment the cell is a eukaryotic cell. In one embodiment the cell is a mammalian cell. In one preferred embodiment the mammalian cell is selected from the group consisting of a CHO cell, BHK cell, an NSO cell, a Sp2/0 cell, a COS cell, a HEK cell, and a PER.C6® cell.

A "polypeptide" is a polymer consisting of amino acids joined by peptide bonds, whether produced naturally or synthetically. Polypeptides of less than about 20 amino acid residues may be referred to as "peptides", whereas polypeptides consisting of more than 100 amino acid residues or consisting of two or more polypeptide chains may be referred to as "proteins".

Polypeptides may also comprise non-peptidic components, such as carbohydrate groups, metal ions, lipids, carboxylic acid esters, or combinations thereof. The non-peptidic substituents may be added by the cell, in which the polypeptide or protein is produced, and may vary with the type of cell. Polypeptides are defined herein in terms of their amino acid sequence; additions such as carbohydrate groups are generally not specified, but may be present nonetheless.

"Heterologous DNA" or "heterologous nucleic acid" refers to a DNA molecule or a nucleic acid, or a population of DNA molecules or a population of nucleic acids, which are introduced into a cell by man, i.e. are introduced artificially into a cell. DNA molecules heterologous to a particular cell may contain DNA derived from the cell species (i.e. endogenous DNA) so long as that DNA is combined with non-cell DNA (i.e. exogenous DNA). For example, a DNA molecule containing a non-cell DNA segment encoding a polypeptide operably linked to a cell DNA segment comprising a promoter is considered to be a heterologous DNA molecule. Conversely, heterologous DNA can comprise an endogenous structural gene operably linked with an exogenous promoter.

A polypeptide encoded by a nucleic acid which cannot be found in a naturally occurring cell, i.e. which is heterologous, is a "heterologous" polypeptide.

The term "biologically active polypeptide" as used herein refers to an organic molecule, e.g. a biological macromolecule such as a peptide, polypeptide, protein, glycoprotein, nucleoprotein, mucoprotein, lipoprotein, synthetic polypeptide or protein, that causes a biological effect when administered in or to artificial biological systems, such as bioassays using cell lines and viruses, or in vivo to an animal, including but not limited to birds and mammals, including humans. This biological effect can be but is not limited to enzyme inhibition or activation, binding to a receptor or a ligand, either at the binding site or circumferential, signal triggering or signal modulation. In one embodiment said biologically active polypeptide is selected from the group consisting of immunoglobulins, immunoglobulin fragments, and immunoglobulin conjugates.

The term "amino acid" denotes a group of carboxy α-amino acids, which either directly or as precursor can be encoded by nucleic acids, comprising alanine (three letter code: Ala, one letter code: A), arginine (Arg, R), asparagine (Asn, N), aspartic acid (Asp, D), cysteine (Cys, C), glutamine (Gln, Q), glutamic acid (Glu, E), glycine (Gly, G), histidine (His, H), isoleucine (Ile, I), leucine (Leu, L), lysine (Lys, K), methionine (Met, M), phenylalanine (Phe, F), proline (Pro, P), serine (Ser, S), threonine (Thr, T), tryptophan (Trp, W), tyrosine (Tyr, Y), and valine (Val, V).

A "cloning plasmid" is a nucleic acid, such as a plasmid, cosmid, phagemid or bacterial artificial chromosome (BAC), which has the capability of replicating autonomously in a cell. Cloning plasmids typically contain one or a small number of restriction endonuclease recognition sites that allow insertion of a nucleic acid in a determinable fashion without loss of an essential biological function of the plasmid, as well as nucleotide sequences encoding a selectable marker, that is suitable for use in the identification and selection of cells transformed with the cloning plasmid. Selectable markers typically include genes that provide tetracycline, neomycin, puromycin, G418, or ampicillin resistance.

An "expression plasmid" is a nucleic acid encoding a (heterologous) polypeptide to be expressed in a cell. Typically, an expression plasmid comprises a prokaryotic plasmid propagation unit, e.g. for $E.$ $coli$, comprising a prokaryotic origin of replication and a prokaryotic selection marker, a eukaryotic selection marker, and one or more expression cassettes for the expression of a nucleic acid of interest (structural gene), each comprising a promoter, a nucleic acid (structural gene), and a transcription terminator including a polyadenylation signal. Gene expression is usually placed under the control of a promoter, and such a structural gene is said to be "operably linked" to the promoter. Similarly, a regulatory element and a core promoter are operably linked if the regulatory element modulates the activity of the core promoter.

A "polycistronic transcription unit" is a transcription unit in which more than one structural gene is under the control of the same promoter.

An "isolated polypeptide" is a polypeptide that is essentially free from contaminating cellular components, such as not covalently bound carbohydrate, lipid, or other proteinaceous impurities as well as non-proteinaceous impurities associated with the polypeptide in nature. Typically, a preparation of isolated polypeptide contains the polypeptide in a highly purified form, i.e. at least about 80% pure, at least about 90% pure, at least about 95% pure, greater than 95% pure, or greater than 99% pure. One way to show that a particular preparation contains an isolated polypeptide is by the appearance of a single band following sodium dodecyl sulfate (SDS)-polyacrylamide gel electrophoresis of the preparation and Coomassie Brilliant Blue staining of the gel. However, the term "isolated" does not exclude the presence of the same polypeptide in alternative physical forms, such as dimers or alternatively glycosylated or derivatized forms.

As used herein, the term "immunoglobulin" denotes a protein consisting of one or more polypeptides substantially encoded by immunoglobulin genes. This definition includes variants such as mutated forms, i.e. forms with substitutions, deletions, and insertions of one or more amino acids, truncated forms, as well as fused forms. The recognized immunoglobulin genes include the different constant region genes as well as the myriad immunoglobulin variable region genes. Immunoglobulins may exist in a variety of formats, including, for example, Fv, Fab, and F(ab)$_2$ as well as single chains (scFv) (e.g. Huston, J. S., et al., Proc. Natl. Acad. Sci. USA 85 (1988) 5879-5883; Bird, R. E., et al., Science 242 (1988) 423-426; and, in general, Hood et al., Immunology, Benjamin N.Y., 2nd edition (1984) and Hunkapiller, T., and Hood, L., Nature 323 (1986) 15-16).

Each of the immunoglobulin heavy and light chains, if present at all, may comprise a constant region (generally the carboxyl terminal portion). The constant region of the heavy chain mediates the binding of the antibody i) to cells bearing a Fc receptor, such as phagocytic cells, or ii) to cells bearing the neonatal Fc receptor (FcRn) also known as Brambell receptor. It also mediates the binding to some factors including factors of the classical complement system such as component C1q. Furthermore a transmembrane domain may follow the C-terminal constant domain of an immunoglobulin heavy chain, i.e. the $C_H^3$ or $C_H^4$ domain. This transmembrane domain allows for the formation of plasma-membrane-bound immunoglobulins or immunoglobulin fragments or immunoglobulin-fusion polypeptides.

Each of the immunoglobulin heavy and light chains, if present at all, may comprise a variable domain (generally the amino terminal portion). The variable domain of an immunoglobulin's light or heavy chain comprises different segments, i.e. four framework regions (FR) and three hypervariable regions (CDR).

The term "at least a fragment of" denotes a fraction of a complete nucleic acid or a complete polypeptide, i.e. at least 20%, at least 40%, at least 60%, or at least 80% of the complete nucleic acid, polypeptide, or domain. For example, "a nucleic acid encoding at least a fragment of an immunoglobulin $C_H^3$ or $C_H^4$ domain" denotes a fraction of the nucleic acid encoding the complete immunoglobulin $C_H3$ or $C_H4$ domain, i.e. at least 20%, at least 40%, at least 60%, or at least 80% of the nucleic acid encoding the complete immunoglobulin $C_H3$ or $C_H4$ domain. In one embodiment a fragment of an immunoglobulin heavy chain is a C-terminal fragment of an immunoglobulin heavy chain.

The term "an in frame translational stop codon" denotes a translational stop codon (TAA, TAG, or TGA) which is succeeding a coding region of a nucleic acid without a frameshift of the reading frame with respect to the preceding coding region of the nucleic acid, i.e. which terminates the translation of said coding region during the translation process. An in frame translational stop codon is operably linked to the preceding coding region of a nucleic acid.

The term "without an in frame translational stop codon" denotes the absence of a translational stop codon (TAA, TAG, or TGA) in the designated nucleic acid and/or alternatively the presence of a translational stop codon, which can be found within or at the end of a coding region of a nucleic acid, but that is due to one or two basepair shifts not recognized during the translation of the processed mRNA (i.e. it is out-of-frame and, thus, not operably linked to the preceding nucleic acid) and, thus, does not terminate the translation process.

The term "transcription terminator" denotes a DNA sequence of 50-750 base pairs in length, which gives the RNA polymerase the signal for termination of the mRNA synthesis. Very efficient (strong) terminators at the 3' end of an expression cassette are advisable to prevent the RNA polymerase from reading through, particularly when using strong promoters. Inefficient transcription terminators can lead to the formation of an operon-like mRNA which can be the reason for an undesired, e.g. plasmid-coded, gene expression.

The terms "not constitutively removed during pre-mRNA processing" and "not constitutively spliced out of the (corresponding) pre-mRNA" as used within this application denote a splicing process that does not unexceptionally take place during pre-mRNA processing, i.e. the nucleic acid of a specific intron is only sometimes removed during pre-mRNA processing. As a result two different mature mRNAs are obtained from the same pre-mRNA, whereof one comprises at least a part of the intron and the other is without the intron.

The term "GPI-anchor" as used within this application denotes a posttranslational modification attached to a C-terminus of a polypeptide or protein. A "GPI-anchor" has a core structure comprising at least one ethanolamine phosphate residue, a trimannoside, a glucosamine residue, and an inositol phospholipid. Notwithstanding this core structure a GPI-anchor normally possesses a certain microheterogeniety and therefore a protein having a GPI-anchor normally is a mixture of proteins with homologous GPI-anchors of the same core structure having different side chain modifications.

The term "signal peptide for a GPI-anchor" denotes a C-terminal amino acid sequence of a polypeptide or protein which consists of one amino acid to which the GPI-anchor will be attached, an optional spacer peptide, and a hydrophobic peptide. Almost all of this signal peptide, i.e. the optional spacer peptide and the hydrophobic peptide, is removed posttranslationally by the enzyme GPI-transaminase and a bond between the amino group of the core ethanolamine phosphate of the GPI-anchor and the amino acid to which the GPI-anchor is attached is formed.

Cell Selection

After transfection with a heterologous nucleic acid cells expressing the polypeptide encoded by the heterologous nucleic acid have to be selected. For selection a marker has to be used. The marker indicates cells in a population of cells that have been successfully transformed with the heterologous nucleic acid by the phenotype it is conferring to the successfully transfected cells. The marker facilitates the selection and isolation of the successfully transfected cells. Different markers can be used, such as, e.g., selectable markers, or detectable labels like Green Fluorescent Protein (GFP).

Selection of cells can be performed in a single step or in multiple steps. In a single/multiple step procedure the first selection can be performed based e.g. on a threshold level of a selectable marker, such as a detectable label. For example, for selection by flow cytometry (e.g. by FACS—Fluorescence Activated Cell Sorting) a fluorescence threshold level is set and cells with a fluorescence above this threshold level are selected. Alternatively cells within the top 1-15% (i.e. the 15% of the cells with the most intense detectable label), or top 1-10%, or top 1-5%, or top 5-10%, or top 5-6% of fluorescence intensity of the sample population can be collected. An alternative method for the selection of a cells is immunological binding, e.g. to magnetic beads coated with Protein A or specific immunoglobulins. The selected panel of cells may be taken as basic population for a further selection step, e.g. by single cell seeding, cultivation and ELISA analysis (Enzyme-linked Immunosorbent Assay), or by limited dilution cloning, or by expanding by cultivation under selective culture conditions in selection medium for several days and a further FACS selection, or by a further FACS selection with a higher threshold level, which can for example be based on the fluorescence intensities detected in a preceding FACS selection, or by an immunoprecipitation method (see e.g. also WO 2005/020924). In one embodiment selecting a cell is performed by a method selected from the group of flow cytometry, ELISA, immunoprecipitation, immunoaffinity column chromatography, magnetic bead immunoaffinity sorting, microscopy-based isolation methods, or immunological binding. In one embodiment selecting a cell is performed by a method selected from the group of flow cytometry, ELISA, immunoprecipitation, immunoaffinity column chromatography, magnetic bead immunoaffinity sorting, microscopy-based isolation methods, or immunological binding, followed by a method selected from the group of single cell seeding and cultivation, limited dilution, or expanding by cultivation, followed by a method selected from the group of FACS, immunoprecipitation, immunoaffinity column chromatography, magnetic bead immunoaffinity sorting, microscopy-based isolation methods, or ELISA As the efficacy of transfection methods known in the art is very high and, thus, a plurality of transfected cells is obtained, marker are preferred that also allow for the correlation of the expression yield of a transfected cell with the detected "intensity" of the marker. Therefore it is functional to link the expression of the (heterologous) polypeptide of interest with the expression of the marker.

The Current Invention

The nucleic acid as reported herein uses splicing methodology, i.e. alternative splicing, to express a polypeptide of interest and a marker from the same nucleic acid, i.e. from the same expression cassette wherein no IRES is employed. The marker in the method as reported herein is a plasma-membrane-bound form of the polypeptide of interest. In the methods as reported herein a selectable marker comprises as N-terminal part the polypeptide of interest and as C-terminal part at least a fragment of a transmembrane domain is used. Thus, the produced polypeptide of interest and the extracellular part of the selectable marker, i.e. the part of the selectable marker which is detected, are identical.

The invention is based at least in part on the finding that specific modifications in the alternative splice acceptor site (3'-splice site region) can be used to regulate the splicing ratio in an alternatively spliced nucleic acid. These modifications can be made to adopt the expression of the marker, i.e. the polypeptide of interest comprising the transmembrane domain at its C-terminus (i.e. the longer construct), to the used cell line. This is especially useful when the alternatively spliceable nucleic acid is used in CHO cell (this results in a good ratio of soluble and membrane-bound immunoglobulin).

Alternative Splicing

During transcription of DNA a copy of the DNA is generated, the so called pre-messenger RNA (pre-mRNA). This pre-mRNA is a 1:1 copy of the template DNA, i.e. it comprises the same elements as the template DNA. For example, if the template DNA has a genomic intron-exon organization the pre-mRNA will have the identical genomic intron-exon-organization.

Only the exons contain the information of the amino acid sequence of the encoded polypeptide. Thus, the introns have to be removed from the pre-mRNA prior to translation. This process is called RNA-splicing.

A "spliceable nucleic acid" is characterized by at least a 5' splice donor site, a 3' splice acceptor site, and a so called branch site, which is normally located 20-50 bases upstream of the acceptor site. This architecture affects the recognition and the excision of the nucleic acid from the 5' splice donor site to the 3' splice acceptor site from the pre-mRNA during RNA splicing. During the splicing step the mature mRNA from which a polypeptide is translated is generated.

But the splicing process is not exclusive. If the intron is an alternatively spliceable intron (=alternatively spliceable nucleic acid) this intron is not mandatorily removed during the splicing process but can be maintained. Thus, such an intron is not removed during pre-mRNA processing from the pre-mRNA and is (at least partially) maintained in the mature mRNA. If an in frame stop codon is present in this alternatively spliceable intron the later translation process stops at this stop codon and a shorter construct is produced.

The recognition and excision of an intron is often regulated by additional cis-acting elements in the pre-mRNA. Due to their function and position these elements are referred to as exonic splice enhancer (ESE), exonic splice silencer (ESS), intronic splice enhancer (ISE), or intronic splice silencer (ISS), respectively (Black, D. L., Annu. Rev. Biochem. 72 (2003) 291-336).

The genomic DNA of most eukaryotic genes has an intron-exon-organization. For example, within the exon encoding the C-terminal domain of the secreted form of an immunoglobulin heavy chain (i.e. $C_H3$ or $C_H4$, respectively) is a 5' splice donor site.

If this splice donor site is not effective in the processing of the heavy chain pre-mRNA, the intron following this exon, which contains a stop codon and a polyadenylation signal, is at least partially retained in the mature mRNA. The mRNA is then translated into an immunoglobulin heavy chain that ends with a $C_H3$ or $C_H4$ domain and represents a soluble immunoglobulin (=shorter construct). This is the major processing pathway for immunoglobulin heavy chain genes in immunoglobulin secreting cells.

If this splice donor site is effective in the processing of the immunoglobulin heavy chain pre-mRNA, the consecutive intron, and therewith the stop codon is removed. Hence the translation does not stop after the C-terminal domain of the immunoglobulin heavy chain. Furthermore, translation is continued with the succeeding spliced thereto exons encoding a transmembrane domain. This minor processing pathway for immunoglobulin heavy chain genes results in a plasma-membrane-bound immunoglobulin form presented on the cell surface of an immunoglobulin producing cell (=longer construct).

This process is referred to as "alternative splicing" and the nucleic acid (i.e. the intron) optionally removed in this process is referred to as "alternatively spliceable nucleic acid".

If a nucleic acid encoding a polypeptide of interest is linked to a nucleic acid encoding at least a fragment of a transmembrane domain by/via an alternatively spliceable nucleic acid, i.e. an alternatively spliceable nucleic acid is located in between these two nucleic acids, and whereby these three nucleic acids are operably linked, two variants of the polypeptide of interest are expressed: a soluble variant, i.e. a variant only comprising the polypeptide of interest (=shorter construct), and a plasma-membrane-bound variant, i.e. a variant comprising both, the polypeptide or protein and the transmembrane domain (=longer construct).

For example, for the recombinant expression of immunoglobulin heavy chains in eukaryotic cells a nucleic acid either with genomic intron-exon-organization or only containing the coding regions, i.e. cDNA, can be employed. In both cases the nucleic acid ends with the stop codon after the exon encoding the C-terminal domain of the immunoglobulin heavy chain. The thereafter in the genomic organization succeeding introns and exons, comprising an alternatively spliceable nucleic acid and a transmembrane domain, are omitted. Therefore with such a nucleic acid only a soluble immunoglobulin heavy chain can be and is obtained.

If for recombinant expression of immunoglobulins or fragments thereof the genomic organization of the immunoglobulin heavy chain gene is retained at least partially, i.e. if the intron after the exon encoding the C-terminal domain (i.e. the alternatively spliceable nucleic acid) and the succeeding exon(s) encoding the immunoglobulin transmembrane domain are retained, alternative splicing is possible. In the alternative splicing event the 3' terminal codons and the stop codon of the CH3- or CH4-domain encoding exon, respectively, are removed as/with the intronic sequence and a different, mature mRNA is generated instead, in which the coding region, i.e. the reading frame, is elongated at its 3' end by the additionally maintained exon(s). This mRNA is translated into a C-terminally extended immunoglobulin heavy chain which contains an additional transmembrane domain, or a fragment thereof, encoded by the additional 3' exon(s). This elongated immunoglobulin heavy chain is incorporated during the assembly of immunoglobulins resulting in plasma-membrane-bound immunoglobulins.

With such a nucleic acid transfected cells producing an immunoglobulin can be selected based on the plasma-membrane-bound immunoglobulin variant.

According to WO 2007/131774 cell lines that simultaneously express two variants of an antibody, i.e. the secreted form (named sIgG in the following) and the membrane bound form (named mIgG in the following), can be generated. Both variants consist of the same light chain but different heavy chain isoforms that arise by different processing, i.e. alternative splicing, of the heavy chain pre-mRNA. The pre-mRNA is either cut and polyadenylated at the polyadenylation site that is located within intron 6 downstream of the exon encoding the CH3 domain, resulting in the shorter heavy chain isoform of sIgG. Competitively, intron 6 (including the polyadenylation site) is removed from the pre-mRNA by splicing and, thus, resulting in the longer heavy chain isoform mIgG. Such cell lines are generated by stable transfection with a plasmid that allows the expression of both isoforms. The purpose thereof is to create and identify cell lines that express the secreted form of a desired antibody on a high level.

Ideally, the primary transcript of the heavy chain transgene is predominantly processed to the small mRNA isoform, giving rise to the secreted sIgG form of the antibody, and only a minor amount is completely spliced to the long mRNA isoform, thus, leading to membrane bound mIgG.

But the expression ratio of these two mRNA variants can be unfavorable depending on the cell line resulting in a too high expression level of the mIgG resulting in turn in a reduced expression level of the sIgG and thereby in a reduced production yield of the respective cell.

In transfected CHO cells, for example, a nearly equal amount of both mRNA isoforms can be determined. The portion of the heavy chain pre-mRNA that is spliced into the mIgG isoform is thereby lacking for the expression of the secreted sIgG.

The invention is outlined in the following with an exemplary polypeptide of interest, which is an immunoglobulin. This has not to be understood as a limitation of the invention—it can be practiced with any polypeptide.

It has been found that the ratio of the two isoforms can be modified by using a modified nucleic acid based on the plasmid pmIgGΔ-B as reported in WO 2007/131774.

Based on plasmid pmIgGΔ-B different new constructs have been made. These differ by point mutations within the 3'-splice site region of heavy chain intron 6:

pmIgGΔ-mut-bp differs from pmIgGΔ-B by two base pairs near the branch point pmIgGΔ-mut-p(Y) differs from pmIgGΔ-B by four base pairs within the polypyrimidine tract pmIgGΔ-mut-bp-p(Y) differs from pmIgGΔ-B by both, the branch point and the polypyrimidine tract mutations All mutations were inserted into pmIgGΔ-B by standard site-directed mutagenesis and cloning procedures. The DNA sequence of that region in plasmid pmIgGΔ-B and the inserted mutations in the plasmids pmIgGΔ-mut-bp, pmIgGΔ-mut-p(Y) and pmIgGΔ-mut-bp-p(Y) are listed in the following Table (mutated base pairs are highlighted in bold; the upper row shows the position of the 3'-fragment of intron 6, the 3'-splice site (depicted by vertical line) and the 5'-fragment of exon M1-M2; the bottom row shows the consensus sequence of that region including the branch point, the polypyrimidine tract and the 3'-splice site as reported by Zhang, M., Hum. Mol. Genet. 7 (1998) 919).

| | ..........intron 6..........\|exon M1-M2 |
|---|---|
| pmIgGΔ-B (SEQ ID NO: 01) | 5'...CAGCACTGACCACCCCCTTCCTGTCCAG\|AGCTG...3' |
| pmIgGΔ-mut-bp (SEQ ID NO: 02) | 5'...CAGCACCTACCACCCCCTTCCTGTCCAG\|AGCTG...3' |
| pmIgGΔ-mut-p(Y) (SEQ ID NO: 03) | 5'...CAGCACTGACCACGCCAATCGTGTCCAG\|AGCTG...3' |
| pmIgGΔ-mut-bp-p(Y) (SEQ ID NO: 04) | 5'...CAGCACCTACCACGCCAATCGTGTCCAG\|AGCTG...3' |
| 3'-splice site consensus sequence (SEQ ID NO: 05) | nnYTVAy    yyyyyyyyyyynYAG \| gt<br>branch point   poly(Y) tract  3'-splice site |

Reference constructs have been obtained based on the analysis of 50 base pairs from plasmid pmIgGΔ-B in order to identify putative exonic splice enhancer (ESE) sites. The region spans the last eight base pairs of intron 6 and the 42 adjacent base pairs of exon M1-M2 in 5'-3'-direction.

Putative ESE sites for the human SR proteins SF2/ASF, SC35, SRp40 and SRp55 were sought using the computer program 'ESEfinder' (see Cartegni, L., et al., Nuc. Acids Res. 31 (2003) 3568). The program identified 11 putative ESE sites with a score between 2.04536 and 5.53775 as shown in the following Table (the upper part shows the 50 base pair DNA sequence around the 5' end of exon M1-M2 in plasmid pmIgGΔ-B; the lower part shows the identified putative ESE sites in that region for four human SR proteins, the position and DNA sequence and a valuation by score).

| pmIgGΔ-B sequence analyzed by ESEfinder |
|---|
| 10 20 30 40 50<br>CTGTCCAG\|AGCTGCAACTGGAGGAGAGCTGTGCGGAGGCGCAGGACGGGG<br>Intron 6\| Exon M1-M2                                  (SEQ ID NO: 09) |

| putative ESE sites for human SR proteins | | | |
|---|---|---|---|
| SR protein | position | site | score |
| SF2/ASF | 6 | CAGAGCT | 2.80777 |
| SF2/ASF | 18 | TGGAGGA | 2.34103 |
| SF2/ASF | 30 | GTGCGGA | 2.04536 |
| SF2/ASF | 33 | CGGAGGC | 3.08488 |
| SF2/ASF | 39 | CGCAGGA | 5.53775 |
| SF2/ASF | 42 | AGGACGG | 2.66367 |
| SC35 | 3 | GTCCAGAG | 3.39314 |
| SRp40 | 5 | CCAGAGC | 3.40075 |
| SRp40 | 14 | CAACTGG | 3.45527 |
| SRp55 | 12 | TGCAAC | 2.92201 |
| SRp55 | 31 | TGCGGA | 4.95677 |

Nine base pair exchanges were identified with this in silico method that are intended to remove putative ESE sites. It was taken into account to choose silent mutations that do not alter the amino acid sequence encoded by exon M1-M2.

The modified sequence was analyzed with the ESEfinder program. Compared to the unmodified sequences only 2 putative ESE sites were identified with a score lower than 3. Based on these in silico results the 9 base pairs were exchanged in plasmid pmIgGΔ-B using standard methods for site directed mutagenesis and DNA cloning. The modified plasmid was called pmIgGΔ-mut-ESE. The following Table shows the modified sequence and the ESEfinder program results (the upper part shows the 50 base pair DNA sequence around the 5' end of exon M1-M2 in plasmid pmIgGΔ-mut-ESE; the nine mutated base pairs compared to pmIgGΔ-B are highlighted in bold; the lower part shows the identified putative ESE sites in that region for four human SR proteins, the position and DNA sequence and a valuation by score).

| pmIgGΔ-mut-ESE sequence analyzed by ESEfinder |
|---|
| 10 20 30 40 50<br>CTGTCCAG\|AATTGCAATTGGAAGAGAGCTGTGCTGAAGCTCAAGATGGGG<br>Intron 6\| Exon M1-M2                                  (SEQ ID NO: 10) |

| putative ESE sites for human SR proteins | | | |
|---|---|---|---|
| SR protein | position | site | score |
| SF2/ASF | 39 | CTCAAGA | 2.94284 |
| SC35 | 3 | GTCCAGAA | 2.94325 |

For the biosynthesis of sIgG the pre-mRNA of the heavy chain is polyadenylated at the polyadenylation site within intron 6. This step competes against the removal of intron 6 by splicing for generating the mIgG isoform. To foster the early polyadenylation an additional polyadenylation site was added into intron 6. This resulted in a further reference construct.

For cloning of plasmid pmIgGΔ-SV40p(A) a fragment of 153 bp containing the early polyadenylation site of simian virus 40 (SV40) was inserted into intron 6 of plasmid pmIgGΔ-B, 71 bp downstream of the stop codon of exon CH3. Comparably, plasmid pmIgGΔ-BGH-p(A) was cloned by inserting a 237 bp fragment containing the polyadenylation site of the bovine growth hormone (BGH) in plasmid pmIgGΔ-B at the same position. The plasmids were constructed with standard molecular biological methods.

The method as reported herein is exemplified in the following using CHO-K1 cells (ATCC No. CCL-61; Puck, T. T., et al., J. Exp. Med. 108 (1958), 945-956), which have been pre-adapted to serum-free growth in suspension culture. Every 3-4 days the cells are split into fresh medium. For transfection, the cells are electroporated with the respective plasmid DNA in PBS at room temperature. The cells were transfected with the respective linearized plasmids pmIgGΔ-mut-bp, pmIgGΔ-mut-p(Y), pmIgGΔ-mut-bp-p (Y), pmIgGΔ-mut-ESE, pmIgGΔ-SV40-p(A), pmIgGΔ-BGH-p(A) or pmIgGΔ-B, respectively. Afterwards the cells of each transfection were cultivated as pool for about three weeks under selective pressure starting one day after the transfection for selection of stably transfected cells.

Expression Plasmid for the Antibody Heavy Chain

Three different expression plasmids were constructed that code for the mIgG form of the heavy chain that is linked to a selectable marker at its intracellular C-terminus.

Figure 3:
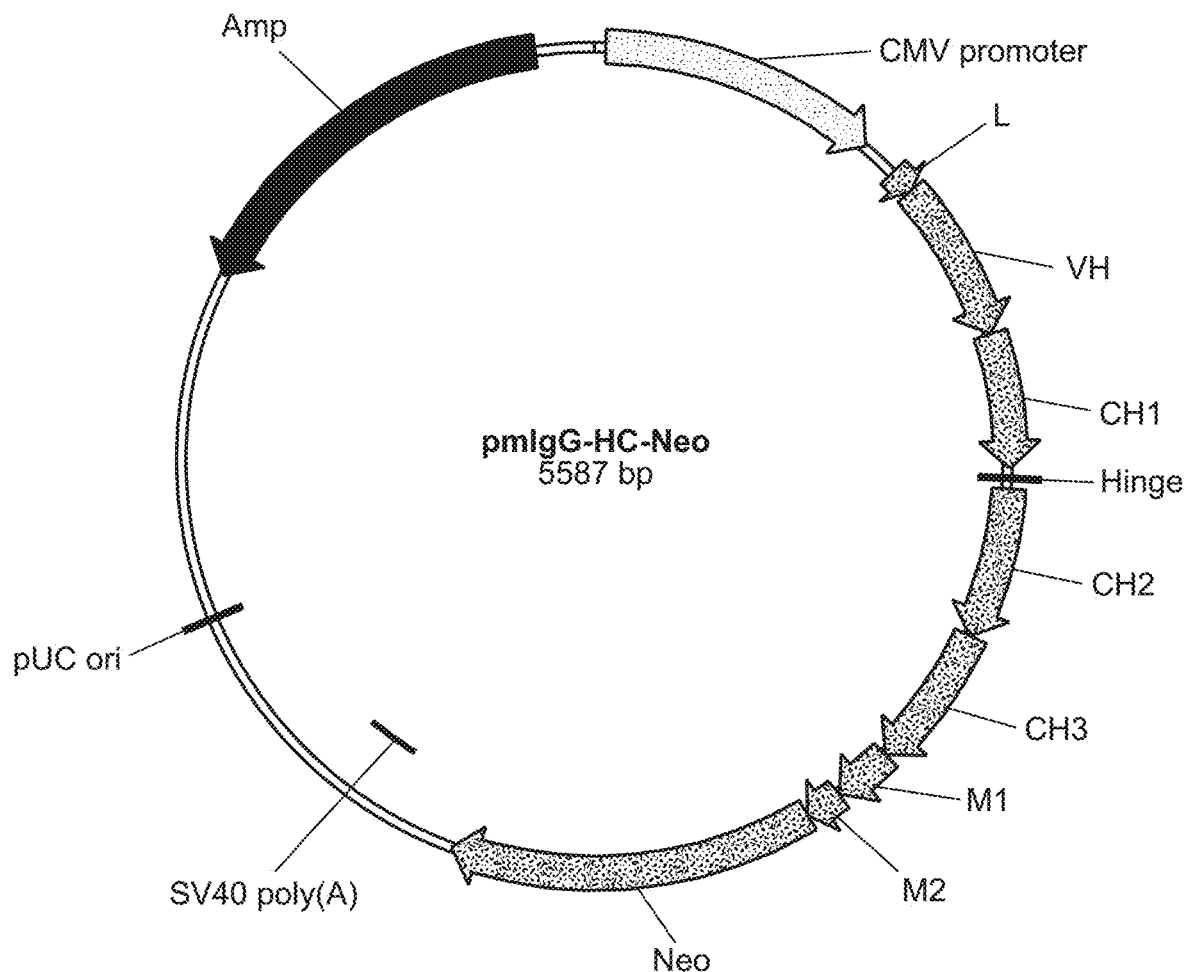
FIG. 3: Plasmid map of pmIgG-HC-Neo.

The first plasmid, pmIgG-HC-Neo, comprises the following elements (see FIG. 3):
1. A transcription unit for the fusion protein of the mIgG form of the heavy chain linked to neomycin phosphotransferase, composed of:
   1.1 the immediate early enhancer and promoter from the human cytomegalovirus (hCMV)
   1.2 the 5' untranslated region of the human immunoglobulin heavy variable 3-33 gene (IGHV3-33).
   1.3 the coding sequence of a fusion protein comprising:
      1.3.1 the cDNA of the leader peptide (L) of IGHV3-33
      1.3.2 a variable heavy chain cDNA (VH) of an antibody specifically binding to a proteinaceous antigen
      1.3.3 the cDNA of the human immunoglobulin heavy constant gamma 1 gene (IGHG1) from exon CH1 to CH3
      1.3.4 the cDNA of exon M1 of the human immunoglobulin heavy constant gamma 3 gene (IGHG3)
      1.3.5 the cDNA of exon M2 of the human immunoglobulin heavy constant gamma 4 gene (IGHG4)
      1.3.6 the cDNA coding for the neomycin phosphotransferase (Neo)
   1.4 the polyadenylation site of simian virus 40 (SV40 poly(A)).
2. An origin of replication from plasmid pUC18 (pUC ori) for the replication of the plasmid in E. coli.
3. A beta-lactamase gene (Amp) conferring ampicillin resistance in E. coli.

Figure 4:
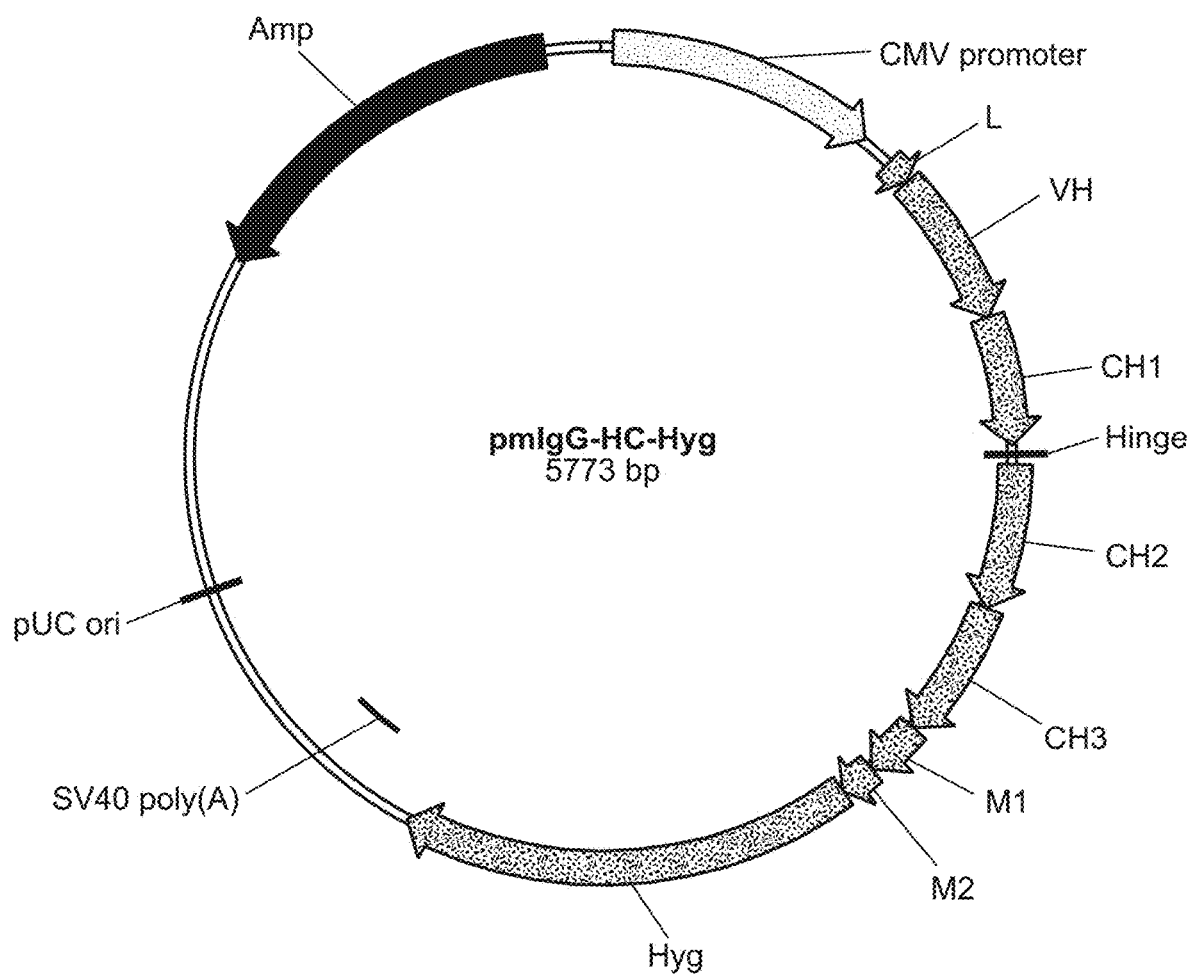
FIG. 4: Plasmid map of pmIgG-HC-Hyg.

The second plasmid, pmIgG-HC-Hyg, comprises the same elements as pmIgG-HC-Neo except the above mentioned element 1.3.6: Instead of the neomycin phosphotransferase cDNA, the cDNA for Hygromycin-phosphotransferase (Hyg) is fused to the M2 cDNA in this plasmid (see FIG. 4).

Figure 5:
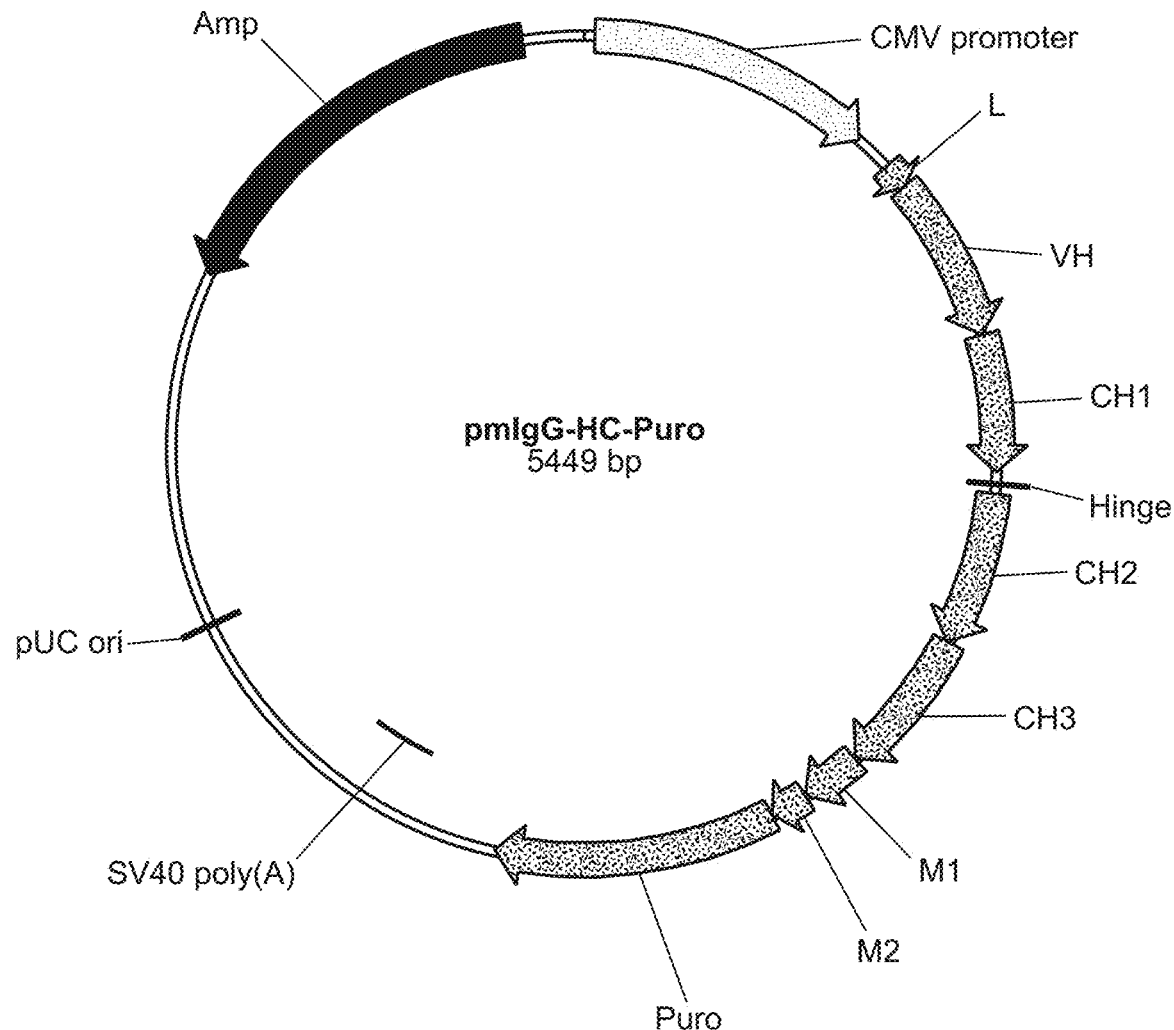
FIG. 5: Plasmid map of pmIgG-HC-Puro.

The third plasmid, pmIgG-HC-Puro, comprises the same elements as pmIgG-HC-Neo except the above mentioned element 1.3.6: Instead of the neomycin phosphotransferase cDNA, the cDNA for Puromycin-N-acetyltransferase (Puro) is fused to the M2 cDNA in this plasmid (see FIG. 5).

Expression Plasmid for Antibody Light Chain

The plasmid pIgG-LC was constructed to express an antibody light chain. It comprises the following elements:
1. A transcription unit for the light chain of an antibody specifically binding to a proteinaceous antigen composed of:
    1.1 the immediate early enhancer and promoter from the human cytomegalovirus (hCMV)
    1.2 the 5' untranslated region of the human immunoglobulin kappa variable 3-11 (IGKV3-11) gene
    1.3 the coding sequence of an immunoglobulin kappa light chain comprising:
        1.3.1 the cDNA of the leader peptide of IGKV3-11
        1.3.2 a variable light chain cDNA of an antibody specifically binding to a proteinaceous antigen,
        1.3.3 the cDNA of the human immunoglobulin kappa constant (IGKC) gene
    1.4 the 3' untranslated region containing the polyadenylation site of IGKC.
2. An origin of replication from plasmid pUC18 for the replication of the plasmid in *E. coli*.
3. A beta-lactamase gene conferring ampicillin resistance in *E. coli*.

Expression Plasmid for sIgG and mIgG-Puro Fusion Protein

The plasmid pmIgG-Puro-mut-p(Y) was designed to express the sIgG form of the antibody specifically binding to a proteinaceous antigen and a transmembrane fusion variant thereof. This variant comprises the same light chain as the sIgG form and a fusion protein of the mIgG heavy chain and the Puromycin-N-acetyltransferase. These two antibody forms should arise by alternative processing of the pre-mRNA of the heavy chain fusion protein as described for mIgG. Additionally, the polypyrimidine tract of intron 6 of the heavy chain was mutated by exchange of four base pair as described for expression plasmid pmIgGΔ-mut-p(Y) see below.

The plasmid pmIgG-Puro-mut-p(Y) consists of the following elements:
1. The transcription unit for the aforementioned sIgG heavy chain or the fusion protein of the mIgG heavy chain and the Puromycin-N-acetyltransferase, composed of:
    1.1 the immediate early enhancer and promoter from the human cytomegalovirus (hCMV),
    1.2 a synthetic 5' untranslated region including a Kozak consensus sequence,
    1.3 a murine immunoglobulin heavy chain signal sequence including the signal sequence intron,
    1.4 a variable heavy chain cDNA of an antibody specifically binding to a proteinaceous antigen,
    1.5 a mouse/human heavy chain hybrid intron 2 including the mouse Ig μ enhancer (JH3-JH4 switch region) joined with the human IGHG1 gene including the exons from CH1 to CH3 with all intervening introns, and the adjacent 5' part of intron 6 including the polyadenylation site for the secreted form of the immunoglobulin,
    1.6 the 3' part of intron 6 from the human IGHG3 gene, including four base pair exchanges within the polypyrimidine tract as listed in the Table below for plasmid pmIgGΔ-mut-p(Y),
    1.7 exon M1 from the human IGHG3 gene, linked to
    1.8 exon M2 from the human IGHG4 gene, linked to
    1.9 Puromycin-N-acetyltransferase cDNA,
    1.10 the polyadenylation site of simian virus 40.
2. A transcription unit for a human kappa light chain, composed of
    2.1 the immediate early enhancer and promoter from the human cytomegalovirus (hCMV),
    2.2 a synthetic 5' untranslated region including a Kozak consensus sequence,
    2.3 a murine immunoglobulin heavy chain signal sequence including the signal sequence intron,
    2.4 a variable κ chain cDNA of an antibody specifically binding to a proteinaceous antigen,
    2.5 the mouse intron 2 Ig κ enhancer joined with the human immunoglobulin κ constant (IGKC) gene, and
    2.6 the human IGKC gene 3' untranslated region containing the polyadenylation site.
3. An origin of replication from the plasmid pUC18 for the replication of the plasmid in *E. coli*.
4. A beta-lactamase gene conferring ampicillin resistance in *E. coli*.

Figure 6:
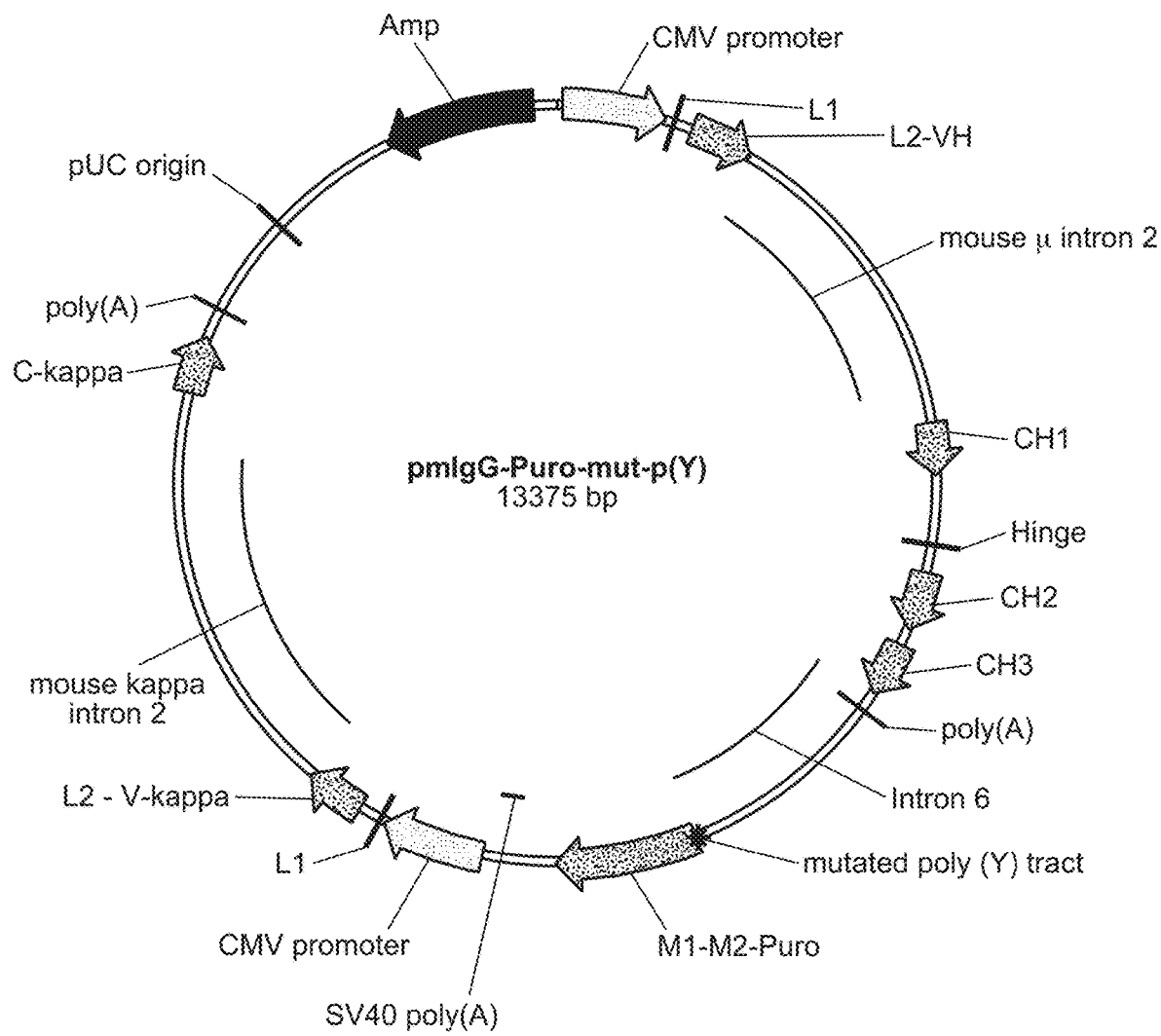
FIG. 6: Plasmid map of pmIgG-Puro-mut-p(Y).

The construction of the plasmid pmIgG-Puro-mut-p(Y) is depicted in FIG. 6.

Expression Plasmid for sIgG and Puromycin-N-Acetyltransferase

The plasmid pIgG-Puro was designed as control plasmid to express the sIgG form of the antibody specifically binding to a proteinaceous antigen, and the puromycin-N-acetyltransferase encoded by an independent expression cassette. It comprises the following elements:
1. The transcription unit for the sIgG heavy chain, composed of:
    1.1 the immediate early enhancer and promoter from the human cytomegalovirus (hCMV),
    1.2 a synthetic 5' untranslated region including a Kozak consensus sequence,
    1.3 a murine immunoglobulin heavy chain signal sequence including the signal sequence intron,
    1.4 a variable heavy chain cDNA of an antibody specifically binding to a proteinaceous antigen,
    1.5 a mouse/human heavy chain hybrid intron 2 including the mouse Ig g enhancer (JH3-JH4 switch region) joined with the human IGHG1 gene including the exons from CH1 to CH3 with all intervening introns, and the adjacent 3' untranslated region containing the polyadenylation site for the heavy chain of the secreted form of IgG1.
2 A transcription unit for a human kappa light chain, composed of
    2.1 the immediate early enhancer and promoter from the human cytomegalovirus (hCMV),
    2.2 a synthetic 5' untranslated region including a Kozak consensus sequence,
    2.3 a murine immunoglobulin heavy chain signal sequence including the signal sequence intron,
    2.4 a variable κ chain cDNA of an antibody specifically binding to a proteinaceous antigen,
    2.5 the mouse intron 2 Ig κ enhancer joined with the human immunoglobulin κ constant (IGKC) gene, and
    2.6 the human IGKC gene 3' untranslated region containing the polyadenylation site.
3. A puromycin-N-acetyltransferase transcription unit as a selectable marker for mammalian cells, containing an SV40 promoter, the puromycin-N-acetyltransferase cDNA and the SV40 polyadenylation site.
4. An origin of replication from the plasmid pUC18 for the replication of the plasmid in *E. coli*.
5. A beta-lactamase gene conferring ampicillin resistance in *E. coli*.

Figure 7:
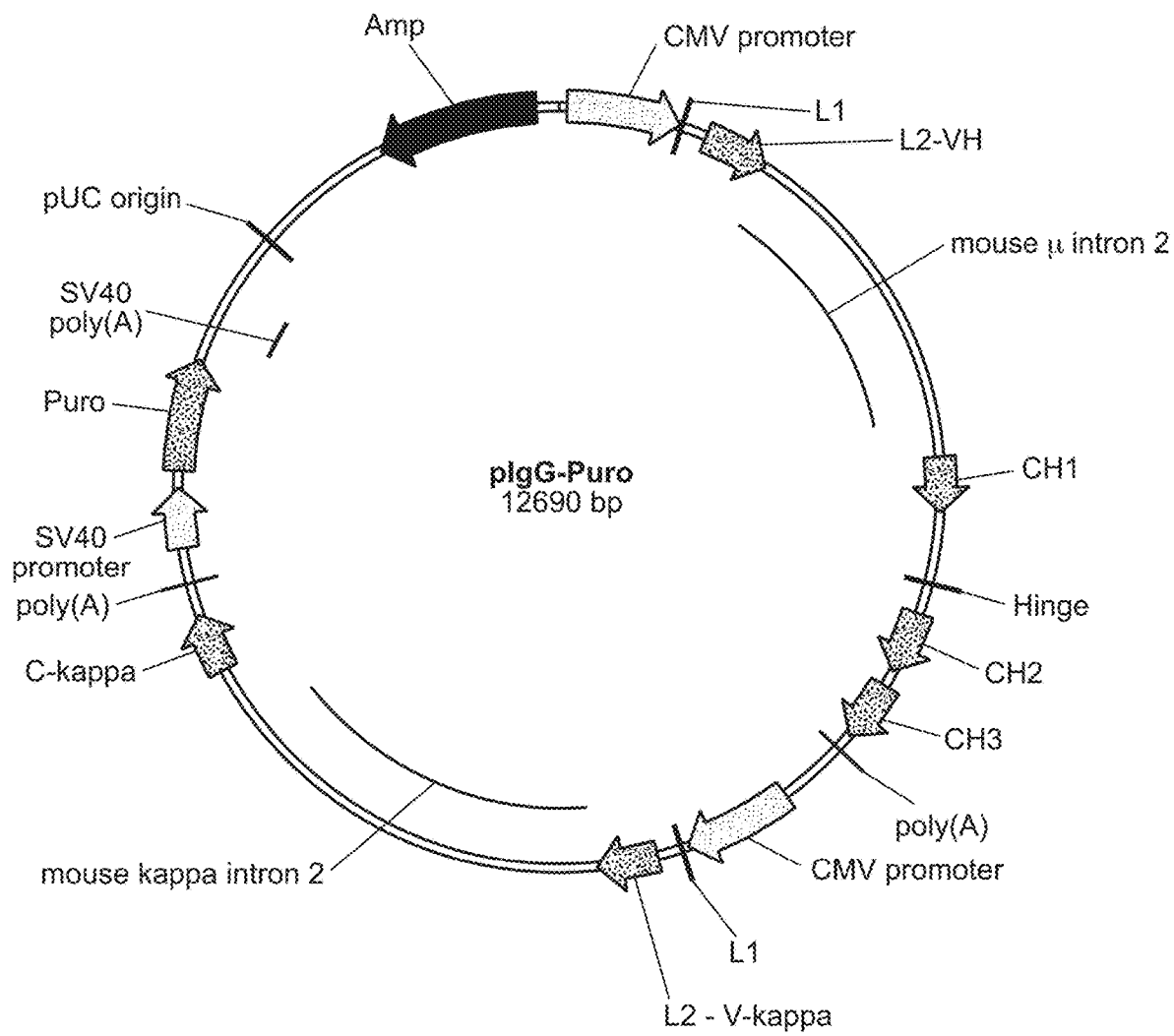
FIG. 7: Plasmid map of pIgG-Puro.

The construction of the plasmid pIgG-Puro is depicted in FIG. 7.

Expression Plasmid for sIgG and Neomycin Phosphotransferase

The plasmid pIgG-Neo was designed to generate an improved expression cell line on a conventional way as described in example 6. The plasmid codes for the heavy and the light chain of the sIgG isoform of the antibody specifically binding to a proteinaceous antigen, and the neomycin phosphotransferase encoded by an independent expression cassette. It comprises the following elements:
1. The transcription unit for the sIgG heavy chain, composed of:
   1.1 the immediate early enhancer and promoter from the human cytomegalovirus (hCMV),
   1.2 a synthetic 5' untranslated region including a Kozak consensus sequence,
   1.3 a murine immunoglobulin heavy chain signal sequence including the signal sequence intron,
   1.4 a variable heavy chain cDNA of an antibody specifically binding to a proteinaceous antigen,
   1.5 a mouse/human heavy chain hybrid intron 2 including the mouse Ig g enhancer (JH3-JH4 switch region) joined with the human IGHG1 gene including the exons from CH1 to CH3 with all intervening introns, and the adjacent 3' untranslated region containing the polyadenylation site for the heavy chain of the secreted form of IgG1.
2. A transcription unit for a human kappa light chain, composed of
   2.1 the immediate early enhancer and promoter from the human cytomegalovirus (hCMV),
   2.2 a synthetic 5' untranslated region including a Kozak consensus sequence,
   2.3 a murine immunoglobulin heavy chain signal sequence including the signal sequence intron,
   2.4 a variable κ chain cDNA of an antibody with specifically binding to a proteinaceous antigen,
   2.5 the mouse intron 2 Ig κ enhancer joined with the human immunoglobulin κ constant (IGKC) gene, and
   2.6 the human IGKC gene 3' untranslated region containing the polyadenylation site.
3. A neomycin phosphotransferase transcription unit as a selectable marker for mammalian cells, containing an SV40 promoter, the neomycin phosphotransferase cDNA and the SV40 polyadenylation site.
4. An origin of replication from the plasmid pUC18 for the replication of the plasmid in *E. coli*.
5. A beta-lactamase gene conferring ampicillin resistance in *E. coli*.

Figure 8:
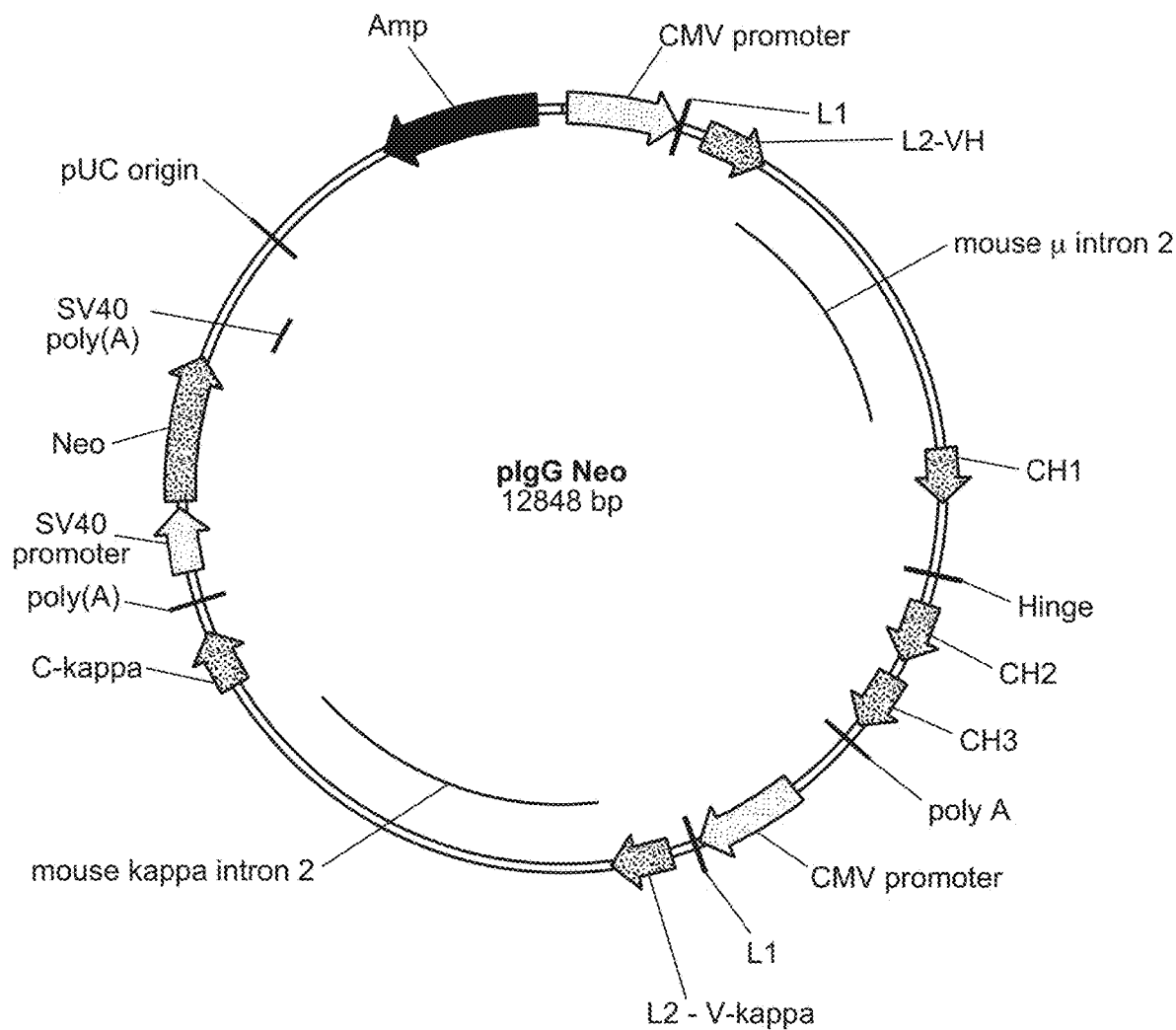
FIG. 8: Plasmid map of pIgG-Neo.

The construction of the plasmid pIgG-Neo is depicted in FIG. 8.

The alternatively spliceable nucleic acid (=second nucleic acid fragment) from the human immunoglobulin γ1 heavy chain has the nucleic acid sequence of SEQ ID NO: 11.

| 5' splice donor site | second nucleic acid (spliceable nucleic acid) | 3' splice acceptor site |
|---|---|---|
| CGG \| GTAAAT | GTAAATGAGTGCCACGGCCGGCAAGCCCCC GCTCCCCAGGCTCTCGGGGTCGCGCGAGGA TGCTTGGCACGTACCCCGTGTACATACTTC CCAGGCACCC . . . (1.3 kb total) . . . CCCGGCCGGGCCCTACATCCTGGGTCCTGC CACAGAGGGAATCACCCCCAGAGGCCCAAG | GTCCAG \| A |
| | CCCAGGGGGACACAGCACTGACCACGCCAA TCGTGTCCAG (SEQ ID NO: 11) | |

As the sequence of the second nucleic acid fragment generally exceeds 1 kb the listed sequences in the Table are shortened and show approximately the first and last 100 nucleotides of the second nucleic acid fragment separated by a number referring to the total size of the complete second nucleic acid. The stop codon is underlined.

The splice donor site is given in a format comprising the preceding consensus sequence of the splice donor site and the first six nucleotides of the second nucleic acid fragment separated by a vertical line (see also e.g. Zhang, M. Q., Human Mol. Gen. 7 (1998) 919-932). Likewise is the splice acceptor site is given by listing the last 6 nucleotides of the second nucleic acid fragment and the succeeding splice acceptor site consensus sequence which are separated by a vertical line. The nucleotides directly after (5' splice donor site) and directly before (3' splice acceptor site) the vertical line are the first and last nucleotides of the second (spliceable) nucleic acid fragment.

The transmembrane stretch (=third nucleic acid fragment) from the human immunoglobulin γ1 heavy chain has the nucleic acid sequence of SEQ ID NO: 12.

| source | nucleotide or amino acid sequence | SEQ ID NO: |
|---|---|---|
| human immunoglobulin γ1 heavy chain/ transmembrane stretch | GGGCTGTGGACGACCATCACCATCTTCAT CACACTCTTCCTGTTAAGCGTGTGCTACA GTGCCACCGTCACCTTCTTC | 12 |

This sequence can follow either directly or with an optional intervening sequence, i.e. a fourth nucleic acid, the 3' splice acceptor site. In the Table below a fourth nucleic acid sequence fragment from the human immunoglobulin γ1 heavy chain is shown.

| source | nucleotide or amino acid sequence | SEQ ID NO: |
|---|---|---|
| human immunoglobulin γ1 heavy chain | AGCTGCAACTGGAGGAGAGCTGTGCGGAG | 13 |

Results

To determine the ratio between the two heavy chain isoforms that emerge by alternative RNA processing of the primary transcript, RNA of stably transfected clones was analyzed by Northern blot. Therefore total RNA was isolated from the seven stably transfected cell pools. Additionally, the RNA of non-transfected CHO-K1 cells was prepared under the same conditions. For each case the same amount of total RNA was then fractionated by denaturing agarose gel electrophoresis and transferred to a nylon membrane. For hybridization of the blot membrane two different DNA probes were marked with [alpha-32P]. As depicted in FIG.

Figure 2A:
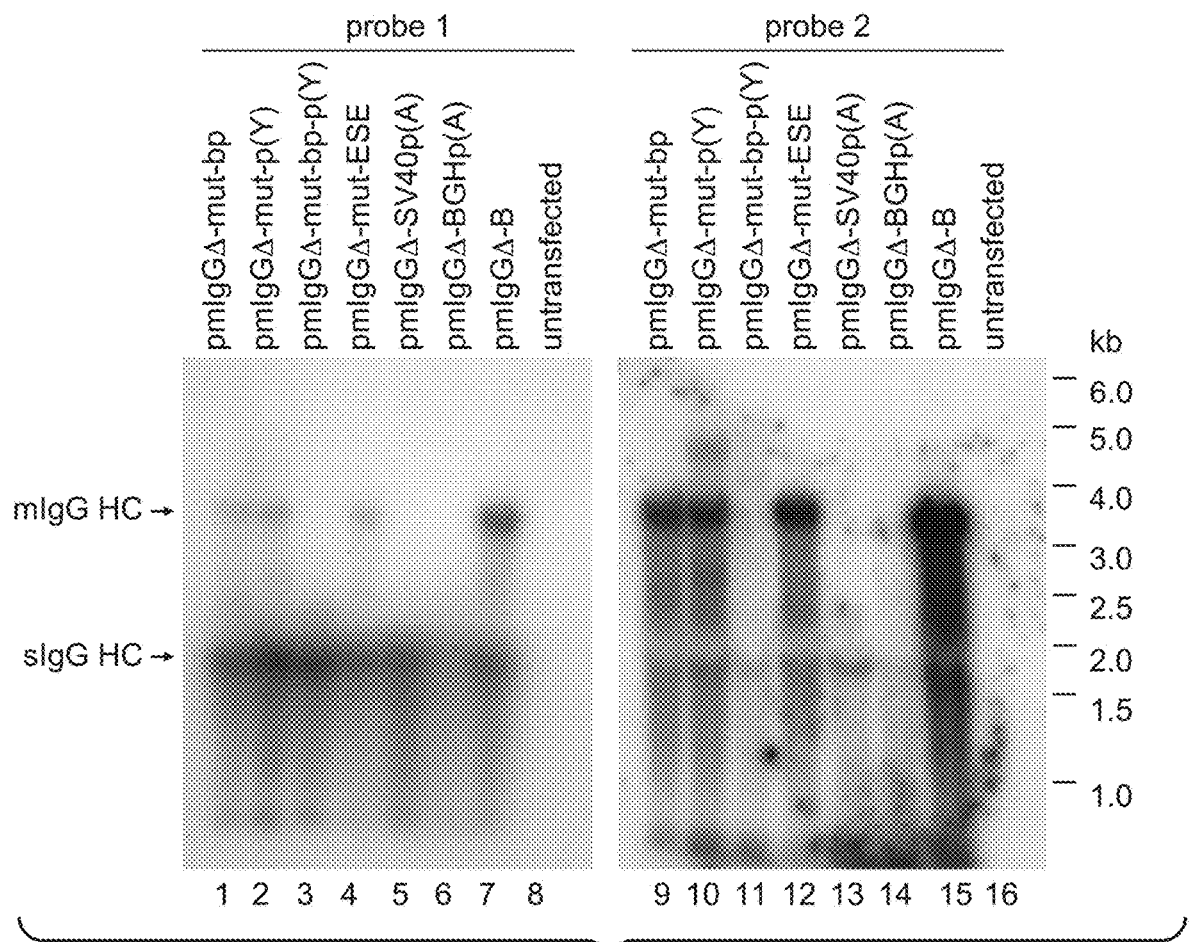
FIGS. 2A-2B: Analysis of mRNA by Northern blot.

2B, probe 1 is complementary to the heavy chain mRNA between exon CH1 and CH3 and thus hybridizes to both isoforms. In contrast, probe 2 only binds to the 3'UTR of the longer mIgG heavy chain mRNA. After hybridization and stringent washing of the membrane the blot was analyzed by autoradiography (see FIG. 2A).

The hybridization with probe 1 shows a 1.8 kb signal for the transfected cell pools, which corresponds to the short mRNA isoform that encodes the heavy chain of sIgG. In the lanes 1, 2, 4 and 7 an additional signal of 3.3 kb is detected. This band represents the long mRNA isoform for mIgG as revealed by hybridization with probe 2 (lanes 9, 10, 12 and 15). The analyzed pools differ in the relative signal strength of the 1.8 kb band to the 3.3 kb band detected by probe 1. The pool of CHO-K1 cells transfected with plasmid pmIgGΔ-B shows a ratio of about 50:50 for the two isoforms. It can be seen that the plasmid modifications at the 3'-splice site region of the heavy chain intron 6 influences the pre-RNA processing. For the pools transfected with pmIgGΔ-mut-bp, pmIgGΔ-mut-p(Y) or pmIgGΔ-mut-ESE a change/shift of the ratio of the two isoforms towards the sIgG isoform can be observed. In the pools transfected with pmIgGΔ-mut-bp-p(Y), pmIgGΔ-SV40-p(A) or pmIgGΔ-BGH-p(A) the mIgG isoform was not detected, neither with probe 1 nor with the much more sensitive probe 2. This indicates that the modifications in those plasmids completely block the splicing of exon CH3 with exon M1-M2.

It can be seen that the mutation of branch point and poly (Y) tract decrease excision of intron 6 by splicing to a sIgG:mIgG ratio of about 90:10 (construct mut-bp-p(Y)). This construct is the preferred construct for performing the methods as reported herein.

This methodology is generally applicable to any polypeptide and is not restricted to immunoglobulins. The only requirement is that the nucleic acid encoding a polypeptide of interest is without an in frame stop codon and is operably linked to and in frame with the alternatively spliceable nucleic acid. Preferably this alternatively spliceable nucleic acid is derived from an immunoglobulin comprising an in frame translational stop codon and a polyadenylation site. The succeeding nucleic acid encoding a transmembrane domain or a fragment thereof is variable and can be selected from any nucleic acid encoding a transmembrane domain or a fragment thereof. These elements, i.e. the nucleic acid encoding the polypeptide of interest, the alternatively spliceable nucleic acid, and the nucleic acid encoding the transmembrane domain, can be selected and combined from different genes as well as different organisms. The three nucleic acids have to be combined in such a way that the translational stop codon in the alternatively spliceable nucleic acid is in frame with the reading frame of the nucleic acid encoding the polypeptide of interest, i.e. it can be recognized by the ribosome and translation is terminated.

Generally speaking, with the alternative splicing optionally a fraction of the C-terminus of the soluble form of the polypeptide of interest is/may be removed from the pre-mRNA as part of an intron. This fraction encompasses optionally the 3' terminal codons, the 3' untranslated region, the stop codon, and the polyadenylation signal of the secreted form. Therefore, the nucleic acid beginning with a 5' splice donor site and terminated by a 3' splice acceptor site that is removed optionally overlaps/may overlap with the C-terminus of the not alternatively processed variant.

Hence, by using a nucleic acid as reported herein with an at least partially retained genomic organization of an immunoglobulin heavy chain gene, two variants of a polypeptide of interest can be obtained, a short, soluble variant and a long, plasma-membrane-bound variant.

The above can be summarized as follows:

One aspect as reported herein is a 3'-fragment of intron 6 of an immunoglobulin heavy chain structural gene that has the nucleic acid sequence TGACCACGCCAATCGTGTCCAG (SEQ ID NO: 14).

One aspect as reported herein is a nucleic acid that has the nucleotide sequence TGACCACGCCAATCGTGTCCAG (SEQ ID NO: 14).

One aspect as reported herein is a nucleic acid at the junction of intron 6 and exon M1 of an immunoglobulin heavy chain structural gene that has the nucleic acid sequence TGACCACGCCAATCGTGTCCAGAGCTG (SEQ ID NO: 15).

One aspect as reported herein is a splice acceptor site nucleic acid that has the nucleotide sequence TGACCACGCCAATCGTGTCCAGAGCTG (SEQ ID NO: 15).

One aspect as reported herein is a nucleic acid comprising in 5' to 3' direction
  i) a first nucleic acid fragment encoding a polypeptide of interest without an in frame translational stop codon,
  ii) a second nucleic acid fragment operably linked to said first nucleic acid fragment which is beginning with the 5' splice donor site of an immunoglobulin heavy chain CH3 or CH4 domain and which is terminated by the 3' splice acceptor site of the succeeding immunoglobulin heavy chain transmembrane domain exon M1 and which comprises in frame translational stop codon and a polyadenylation signal,
  iii) a third nucleic acid fragment operably linked to said second nucleic acid encoding at least a fragment of a transmembrane domain,
  wherein the second nucleic acid fragment has at its 3' terminus the nucleotide sequence TGACCACGCCAATCGTGTCCAG (SEQ ID NO: 14).

One aspect as reported herein is a nucleic acid comprising in 5' to 3' direction
  i) a first nucleic acid fragment encoding a polypeptide of interest without an in frame translational stop codon,
  ii) a second nucleic acid fragment operably linked to said first nucleic acid fragment which is beginning with the 5' splice donor site of an immunoglobulin heavy chain CH3 or CH4 domain and which is terminated by the 3' splice acceptor site of the succeeding immunoglobulin heavy chain transmembrane domain exon M1 and which comprises in frame translational stop codon and a polyadenylation signal,
  iii) a third nucleic acid fragment operably linked to said second nucleic acid encoding at least a fragment of a transmembrane domain,
  wherein the second nucleic acid fragment and the third nucleic acid fragment has at its junction the nucleotide sequence TGACCACGCCAATCGTGTCCAGAGCTG (SEQ ID NO: 15).

Second and Third Nucleic Acid Fragment

The present invention can be practiced with any alternatively spliceable nucleic acid (=second nucleic acid fragment), for example, without limitation, with an alternatively spliceable nucleic acid derived from the group of nucleic acids encoding the C3b/C4b receptor (complement receptor type 1) (Hourcade, D., et al., J. Exp. Med. 168 (1988) 1255-1270), human, chicken, and rat EGFR (Callaghan, T., et al., Oncogene 8 (1993) 2939-2948; Reiter, J. L., and Maihle, N. J., Nuc. Acids Res. 24 (1996) 4050-4056; Petch, L., et al., Mol. Cell Biol. 10 (1990) 2973-2982), immunoglobulin (Ig) α, ε, γ, μ heavy chain (Zhang, K., et al., J. Exp.

Med. 176 (1992) 233-243; Rogers, J. E., et al., Cell 20 (1980) 303-312; Milcarek, C., and Hall, B., Mol. Cell Biol. 5 (1985) 2514-2520; Kobrin, B. J., et al., Mol. Cell Biol. 6 (1986) 1687-1697; Cushley, W., et al., Nature 298 (1982) 77; Alt, F. W., et al., Cell 20 (1980) 293-301; Peterson, M. L., Gene Exp. 2 (1992) 319-327), human $PLA_2$ receptor (Ancian, P., et al., J. Biol. Chem. 270 (1995) 8963-8970), chicken Cek5 (Connor, R. J., and Pasquale, E. B., Oncogene 11 (1995) 2429-2438), human FGFR (Johnson, D. E., et al., Mol. Cell Biol. 11 (1991) 4627-4634, which comprises the modification as reported herein.

In one preferred embodiment the second nucleic acid fragment is based on an intron of an immunoglobulin located between the exon encoding the $C_H3/C_H4$ domain and the exon encoding at least a fragment of the transmembrane domain. In one embodiment the second nucleic acid fragment is based on/derived from the group of nucleic acids encoding human (hu) immunoglobulin (Ig) α (alpha) heavy chain, hu Ig δ (delta) heavy chain, hu Ig ε (epsilon) heavy chain, hu Ig γ1, γ2, γ3, and γ4 (gamma) heavy chain, hu Ig μ (miu) heavy chain, murine Ig heavy chain type α (alpha), murine Ig heavy chain type δ (delta), murine Ig heavy chain type ε (epsilon), murine Ig heavy chain type γ1 (gamma1), murine Ig heavy chain type γ2A (gamma2A), murine Ig heavy chain type γ2B (gamma2B), murine Ig heavy chain type γ3 (gamma3), and murine Ig heavy chain type μ (miu).

In one embodiment the second nucleic acid fragment is based on a nucleic acid selected from the group consisting of nucleic acids encoding human immunoglobulin γ1 heavy chain, human immunoglobulin γ2 heavy chain, human immunoglobulin γ3 heavy chain, human immunoglobulin γ4 heavy chain, human immunoglobulin ε heavy chain (1), and human immunoglobulin ε heavy chain (2).

The present invention can be practiced, for example, without limitation, with a third nucleic acid fragment, in case of the nucleic acid encoding at least a fragment of a transmembrane domain, selected from the group consisting of nucleic acids encoding the C3b/C4b receptor (complement receptor type 1) (Hourcade, D., et al., J. Exp. Med. 168 (1988) 1255-1270), human, chicken, and rat EGFR (Callaghan, T., et al., Oncogene 8 (1993) 2939-2948; Reiter, J. L., and Maihle, N. J., Nuc. Acids Res. 24 (1996) 4050-4056; Petch, L., et al., Mol. Cell Biol. 10 (1990) 2973-2982), Ig α, ε, γ, μ heavy chain (Zhang, K., et al., J. Exp. Med. 176 (1992) 233-243; Rogers, J. E., et al., Cell 20 (1980) 303-312; Milcarek, C., and Hall, B., Mol. Cell Biol. 5 (1985) 2514-2520; Kobrin, B. J., et al., Mol. Cell Biol. 6 (1986) 1687-1697; Cushley, W., et al., Nature 298 (1982) 77; Alt, F. W., et al., Cell 20 (1980) 293-301; Peterson, M. L., Gene Exp. 2 (1992) 319-327), human $PLA_2$ receptor (Ancian, P., et al., J. Biol. Chem. 270 (1995) 8963-8970), chicken Cek5 (Connor, R. J., and Pasquale, E. B., Oncogene 11 (1995) 2429-2438), human FGFR (Johnson, D. E., et al., Mol. Cell Biol. 11 (1991) 4627-4634. In one embodiment the third nucleic acid fragment is selected from the group consisting of nucleic acids encoding human (hu) immunoglobulin (Ig) α (alpha) heavy chain, hu Ig δ (delta) heavy chain, hu Ig ε (epsilon) heavy chain, hu Ig γ1, γ2, γ3, and γ4 (gamma) heavy chain, hu Ig μ (miu) heavy chain, murine Ig heavy chain type α (alpha), murine Ig heavy chain type δ (delta), murine Ig heavy chain type ε (epsilon), murine Ig heavy chain type γ1 (gamma1), murine Ig heavy chain type γ2A (gamma2A), murine Ig heavy chain type γ2B (gamma2B), murine Ig heavy chain type γ3 (gamma3), and murine Ig heavy chain type μ (miu). In one embodiment the third nucleic acid fragment is selected from the group consisting of nucleic acids encoding human immunoglobulin γ1 heavy chain, human immunoglobulin γ2 heavy chain, human immunoglobulin γ3 heavy chain, human immunoglobulin γ4 heavy chain, human immunoglobulin ε heavy chain (1), and human immunoglobulin ε heavy chain (2). In one embodiment the third nucleic acid fragment is selected from the group consisting of nucleic acids encoding human immunoglobulin δ heavy chain, human immunoglobulin γ1 heavy chain, human immunoglobulin γ2 heavy chain, human immunoglobulin μ heavy chain, murine heavy chain type α, murine heavy chain type γ1, murine heavy chain type γ2B, murine heavy chain type γ3, and murine heavy chain type μ.

In addition to the group of third nucleic acid fragments as outlined above, can the third nucleic acid be selected from the group consisting of nucleic acids encoding a signal peptide for a GPI-anchor. The group of nucleic acids encoding a signal peptide for a GPI-anchor comprises the group of nucleic acids encoding a signal peptide for a GPI-anchor derived from human alkaline diesterase, acetylcholine esterase, alkaline phosphatase (intestinal, liver, and placenta), CAMPATH-1 antigen, carcinoembryonic antigen, CD55, CD59, CD90, contactin-1, E48 antigen, folate receptor A and B, GPI-anchored protein p137, lymphocyte function-associated antigen-3, mDIA interacting protein, 5'-nucleotidase, urokinase plasminogen activator factor; from murine LY-6C antigen, LY-6 antigen, 5'-nucleotidase, OX45 antigen, stem cell antigen-2, vascular cell adhesion molecule-1, Qa lymphocyte antigen 2 (Qa2); from rabbit trehalase; from rat brevican protein, CD90, glypican protein, heparin sulfate proteoglycan, MRC OX-45 antigen, 5'-nucleotidase, pancreatic secretory granule membrane major glycoprotein, T-cell surface protein RT6.2; from yeast DNA repair protein PHR1, glycophospholipid-anchored surface protein 1; from porcine amyloid precursor protein, dipeptidase; from *Trypanosoma brucei* diverse variant surface proteins, polycyclic acidic repetitive protein; from *Trypanosoma congolense* variant surface protein YNat 1.1; from chicken melanotransferrin, neutral cell adhesion molecule; from *Torpedo marmorata* acetylcholine esterase; from hamster prion protein; from bovine 5'-nucleotidase; from slime mold membrane protein Gp64, pre-spore specific antigen; and from squid Sgp1, Sgp2.

The second nucleic acid fragment can either be directly linked to the nucleic acid encoding the polypeptide of interest, i.e. the first nucleic acid fragment, or with an optional small (9 to 21 bases) intervening nucleic acid fragment. In one embodiment the optional intervening nucleic acid fragment is derived from the nucleic acid preceding the second nucleic acid in the genome from which said second nucleic acid is obtained.

Likewise the third nucleic acid sequences can follow either directly or with an optional intervening sequence the 3' splice acceptor site.

In one embodiment the nucleic acid comprises a fourth nucleic acid fragment between the second nucleic acid fragment and the third nucleic acid fragment. In one embodiment the nucleic acid comprises a fifth nucleic acid fragment between the first nucleic acid fragment and the second nucleic acid fragment. In one embodiment the third nucleic acid fragment is obtained from i) the same, or ii) a different gene or organism as the second nucleic acid fragment, i.e. the third nucleic acid fragment is not necessarily organized with the second nucleic acid fragment in a genome.

SPECIFIC EMBODIMENTS

1. A 3'-fragment of intron 6 of an immunoglobulin heavy chain structural gene that has the nucleic acid sequence CTACCACCCCCTTCCTGTCCAG (SEQ ID NO: 29) or TGACCACGCCAATCGTGTCCAG (SEQ ID NO: 14) or CTACCACGCCAATCGTGTCCAG (SEQ ID NO: 31).
2. A nucleic acid that has the nucleotide sequence CTACCACCCCCTTCCTGTCCAG (SEQ ID NO: 29) or TGACCACGCCAATCGTGTCCAG (SEQ ID NO: 14) or CTACCACGCCAATCGTGTCCAG (SEQ ID NO: 31).
3. A nucleic acid at the junction of intron 6 and exon M1 of an immunoglobulin heavy chain structural gene that has the nucleic acid sequence CTACCACCCCCTTCCTGTCCAGAGCTG (SEQ ID NO: 30) or TGACCACGCCAATCGTGTCCAGAGCTG (SEQ ID NO: 15) or CTACCACGCCAATCGTGTCCAGAGCTG (SEQ ID NO: 32).
4. A nucleic acid that has the nucleotide sequence CTACCACCCCCTTCCTGTCCAGAGCTG (SEQ ID NO: 30) or TGACCACGCCAATCGTGTCCAGAGCTG (SEQ ID NO: 15) or CTACCACGCCAATCGTGTCCAGAGCTG (SEQ ID NO: 32).
5. A nucleic acid comprising in 5' to 3' direction
   i) a first nucleic acid fragment encoding a polypeptide of interest without an in frame translational stop codon,
   ii) a second nucleic acid fragment operably linked to said first nucleic acid fragment which is beginning with the 5' splice donor site of an immunoglobulin heavy chain CH3 or CH4 domain and which is terminated by the 3' splice acceptor site of the succeeding immunoglobulin heavy chain transmembrane domain exon M1 and which comprises in frame translational stop codon and a polyadenylation signal, optionally further comprising a nucleic acid encoding a selection marker,
   iii) a third nucleic acid fragment operably linked to said second nucleic acid encoding at least a fragment of a transmembrane domain,
   wherein the second nucleic acid fragment has at its 3' terminus the nucleotide sequence CTACCACCCCCTTCCTGTCCAG (SEQ ID NO: 29) or TGACCACGCCAATCGTGTCCAG (SEQ ID NO: 14) or CTACCACGCCAATCGTGTCCAG (SEQ ID NO: 31).
6. A nucleic acid comprising in 5' to 3' direction
   i) a first nucleic acid fragment encoding a polypeptide of interest without an in frame translational stop codon,
   ii) a second nucleic acid fragment operably linked to said first nucleic acid fragment which is beginning with the 5' splice donor site of an immunoglobulin heavy chain $C_H3$ or $C_H4$ domain and which is terminated by the 3' splice acceptor site of the succeeding immunoglobulin heavy chain transmembrane domain exon M1 and which comprises in frame translational stop codon and a polyadenylation signal, optionally further comprising a nucleic acid encoding a selection marker,
   iii) a third nucleic acid fragment operably linked to said second nucleic acid encoding at least a fragment of a transmembrane domain,
   wherein the nucleotide sequence CTACCACCCCCTTCCTGTCCAGAGCTG (SEQ ID NO: 30) or TGACCACGCCAATCGTGTCCAGAGCTG (SEQ ID NO: 15) or CTACCACGCCAATCGTGTCCAGAGCTG (SEQ ID NO: 32) overlaps the second nucleic acid fragment and the third nucleic acid fragment.
7. The nucleic acid according to any one of embodiments 1 to 6, wherein the polypeptide of interest is selected from the group of polypeptides consisting of an immunoglobulin heavy chain, an immunoglobulin light chain, fragments thereof, and fusion polypeptides comprising an immunoglobulin chain or a fragment thereof.
8. The nucleic acid according to any one of embodiments 1 to 7, wherein the polypeptide of interest is an immunoglobulin heavy chain.
9. The nucleic acid according to any one of embodiments 1 to 8, wherein the nucleic acid is comprised in an expression cassette.
10. The nucleic acid according to any one of embodiments 5 to 9, wherein the fragment of a transmembrane domain is a transmembrane region.
11. The nucleic acid according to any one of embodiments 5 to 10, wherein the transmembrane domain encoded is an immunoglobulin transmembrane domain.
12. The nucleic acid according to any one of embodiments 5 to 11, wherein the second nucleic acid fragment comprises only one 5' splice donor site and only one 3' splice acceptor site.
13. The nucleic acid according to any one of embodiments 5 to 12, wherein the second nucleic acid fragment is a naturally occurring immunoglobulin heavy chain intron, which is following the exon encoding an immunoglobulin heavy chain $C_H3$ or $C_H4$ domain, wherein in said intron at least 50 consecutive nucleotides are deleted.
14. The nucleic acid according to any one of embodiments 5 to 13, wherein the first nucleic acid fragment encodes an immunoglobulin heavy chain and comprises all exons and all but one intron of the genomically organized immunoglobulin heavy chain gene.
15. The nucleic acid according to any one of embodiments 5 to 14, wherein the third nucleic acid fragment encodes a fragment of a transmembrane domain, whereby the fragment of the transmembrane domain is encoded by a single exon.
16. The nucleic acid according to any one of embodiments 5 to 15, wherein the transmembrane domain an immunoglobulin transmembrane domain that is encoded by an M1-M2-exon-fusion (a single exon without the genomically intervening intron).
17. The nucleic acid according to any one of embodiments 5 to 16, wherein the immunoglobulin transmembrane domain is encoded by a cDNA.
18. The nucleic acid according to any one of embodiments 5 to 17, wherein the second nucleic acid fragment is based on/derived from the group of nucleic acids encoding human (hu) immunoglobulin (Ig) α (alpha) heavy chain, hu Ig δ (delta) heavy chain, hu Ig ε (epsilon) heavy chain, hu Ig γ1, γ2, γ3, and γ4 (gamma) heavy chain, hu Ig g (miu) heavy chain, murine Ig heavy chain type α (alpha), murine Ig heavy chain type δ (delta), murine Ig heavy chain type ε (epsilon), murine Ig heavy chain type γ1 (gamma1), murine Ig heavy chain type γ2A (gamma2A), murine Ig heavy chain type γ2B (gamma2B), murine Ig heavy chain type γ3 (gamma3), and murine Ig heavy chain type µ (miu).
19. The nucleic acid according to any one of embodiments 5 to 18, wherein the second nucleic acid fragment is based on/derived from a nucleic acid selected from the group consisting of nucleic acids encoding human immunoglobulin γ1 heavy chain, human immunoglobulin γ2 heavy chain, human immunoglobulin γ3 heavy chain, human immunoglobulin γ4 heavy chain, human immunoglobulin ε heavy chain (1), and human immunoglobulin ε heavy chain (2).
20. The nucleic acid according to any one of embodiments 5 to 19, wherein the second nucleic acid fragment has the nucleotide sequence of SEQ ID NO: 11.
21. The nucleic acid according to any one of embodiments 5 to 20, wherein the third nucleic acid fragment has the nucleotide sequence of SEQ ID NO: 12.
22. The nucleic acid according to any one of embodiments 5 to 21, wherein the nucleic acid encoding a selection marker is encoding puromycin-N-acetyltransferase, neomycin phosphotransferase or hygromycin phosphotransferase.

23. A nucleic acid according to any one of claims 1 to 22 for use in selecting stably transfected cells 24. The use of a nucleic acid according to any one of claims 1 to 22 for selecting stably transfected cells.

25. A method for selecting a eukaryotic cell expressing an immunoglobulin, whereby the method comprises
    a) transfecting a eukaryotic cell with one or more nucleic acids comprising a first expression cassette for an immunoglobulin light chain and a second expression cassette for an immunoglobulin heavy chain comprising a nucleic acid according to any one of embodiments 1 to 4 and 8 to 22,
    b) culturing of said transfected cell under conditions suitable for the production of pre-mRNA from said nucleic acid, processing of said pre-mRNA, and translation of said processed mRNA into an immunoglobulin heavy chain, wherein said transfected cell produces soluble immunoglobulin and plasma-membrane-bound immunoglobulin by alternative splicing of said pre-mRNA, and
    c) selecting a cell with plasma-membrane-bound immunoglobulin to be said cell expressing an immunoglobulin.

26. The method according to embodiment 25, comprising the step of
    transfecting a eukaryotic cell with two nucleic acids either simultaneously or sequentially, whereby one nucleic acid comprises an expression cassette for an immunoglobulin light chain and the other nucleic acid comprises an expression cassette for an immunoglobulin heavy chain comprising a nucleic acid according to any one of embodiments 1 to 4 and 8 to 21.

27. The method according to any one of embodiments 25 to 26, wherein the eukaryotic cell is a mammalian cell.

28. The method according to any one of embodiments 25 to 27, wherein the eukaryotic cell is selected from the group consisting of a CHO cell, an NSO cell, an Sp2/0 cell, a COS cell, a K652 cell, a BHK cell, a PER.C6® cell and a HEK cell.

29. The method according to any one of embodiments 25 to 28, wherein the eukaryotic cell is a CHO cell.

30. A nucleic acid comprising
    a) a first multiple cloning site,
    b) a nucleic acid according to any one of embodiments 1 to 22,
    c) a second multiple cloning site.

By introducing a nucleic acid with an at least partially retained overall genomic organization of an immunoglobulin heavy chain gene into a host cell, a cell is obtained, that expresses on the one hand soluble heterologous polypeptide and on the other hand plasma-membrane-bound heterologous polypeptide. For example, to obtain the two immunoglobulin variants, i.e. to enable alternative splicing, it is not necessary to maintain the entire genomic organization of the immunoglobulin heavy chain gene, i.e. all introns and exons. It is only required to maintain the alternative splice site in a functional from. A "functional splice site" is a nucleic acid sequence comprising a 5' splice donor site and a 3' splice acceptor site, thereby allowing for the excision of the interjacent nucleic acid sequence from the pre-mRNA. The recognition and excision of an intron is often regulated by additional cis-acting elements on the pre-mRNA. Due to their function and position these elements are referred to as exonic splice enhancer (ESE), exonic splice silencer (ESS), intronic splice enhancer (ISE), or intronic splice silencer (ISS), respectively (Black, D. L., Annu Rev Biochem 72 (2003) 291-336, which is incorporated by reference herein).

For the selection of transfected cells expressing a polypeptide of interest different methods can be used, such as, without limitation, spectroscopic methods, e.g. fluorescence, ELISA and variants thereof, by assaying for the biological activity, or by employing assays that are independent of such activity, such as Western blotting, SDS polyacrylamide gel electrophoresis, or radioimmunoassay, using antibodies that recognize and bind to the polypeptide of interest. Since the plasma-membrane-bound polypeptide of interest has the same amino acid sequence and secondary structure as the soluble polypeptide of interest except for its C-terminus, it can be determined with, e.g., the same antibodies as the soluble variant.

The plasma-membrane-bound variant of a polypeptide is firmly connected to the cell expressing it. Therefore the plasma-membrane-bound variant can be used as a marker to isolate cells that have been successfully transfected with a nucleic acid for the expression of a polypeptide of interest, e.g. an immunoglobulin.

The molecular ratio of the soluble variant of the polypeptide of interest to the plasma-membrane-bound variant of the polypeptide of interest is of from more than 50:50 to less than 100:0, of from more than 75:25 to less than 100:0, preferably about 90:10.

In other embodiments i) the 5' splice site of the alternatively spliced intron is located 5' to the normal stop-codon of the nucleic acid encoding the immunoglobulin, ii) the second nucleic acid fragment is an alternatively spliceable nucleic acid, and iii) the 5' splice site is used only sometimes and not constitutively, resulting in a molecular ratio of normally processed immunoglobulin, i.e. soluble immunoglobulin, to alternatively processed immunoglobulin, i.e. plasma-membrane-bound immunoglobulin, of from more than 75:25 to less than 100:0, preferably about 90:10.

The nucleic acid that can be removed by alternative splicing follows the nucleic acid encoding at least a fragment of a polypeptide and precedes the nucleic acid encoding at least a fragment of a transmembrane domain. In one embodiment the nucleic acid comprises a fourth nucleic acid between the first nucleic acid fragment and the second nucleic acid fragment and/or the second nucleic acid fragment and the third nucleic acid fragment. That is the fourth nucleic acid fragment is located e.g. after the second nucleic acid fragment (i.e. after the 3' splice acceptor site) and before the 5' end of the third nucleic acid fragment.

With an alternatively spliceable nucleic acid located between the nucleic acid encoding a polypeptide of interest, and the nucleic acid encoding a transmembrane domain, two variants of the polypeptide of interest can be expressed: a polypeptide of interest without transmembrane domain and a polypeptide of interest with transmembrane domain. The polypeptide of interest can be selected from, without limitation, for example, hormones; cytokines; growth factors; receptor ligands, agonists or antagonists; cytotoxic agents; antiviral agents; imaging agents; enzyme inhibitors; enzyme activators or enzyme activity modulators such as allosteric substances; immunoglobulins; or fusions or fragments thereof. In one embodiment the polypeptide is an immunoglobulin, an immunoglobulin heavy chain polypeptide, or an immunoglobulin fusion.

The invention can be practiced with any polypeptide of interest, any transmembrane domain and any signal peptide for a GPI-anchor as long as an alternatively spliceable nucleic acid is embedded thereby. In more detail the nucleic acid fragment beginning with the 5' splice donor site and terminated by the 3' splice acceptor site has to be chosen properly. The preceding polypeptide and the succeeding transmembrane domain or GPI-anchor can be chosen freely.

The following examples, sequences and figures are provided to aid the understanding of the present invention, the true scope of which is set forth in the appended claims. It is

EXAMPLES

Example 1

Cloning of Genomic Fragments and Construction of Eukaryotic sIgG/mIgG Expression Plasmids a) Construction of the sIgG Expression Plasmid pIgG For the expression of an immunoglobulin with binding specificity against a proteinaceous antigen a plasmid was constructed. It codes for the secreted sIgG form of the immunoglobulin and comprises the following elements:

1. A transcription unit for a human gamma (γ) 1 heavy chain, composed of
   the immediate early enhancer and promoter from the human cytomegalovirus (hCMV),
   a synthetic 5' untranslated region including a Kozak consensus sequence (Kozak, M., Nucleic Acids Res. 15 (1987) 8125-48),
   a murine immunoglobulin heavy chain signal sequence including the signal sequence intron,
   a variable heavy chain cDNA of an antibody with binding specificity against said proteinaceous antigen,
   a mouse/human heavy chain hybrid intron 2 including the mouse Ig t enhancer ($J_H3$-$J_H4$ switch region) joined with the human immunoglobulin heavy constant gamma 1 (IGHG1) gene including the exons from $C_H1$ to $C_H3$ with all intervening introns, and the adjacent 3' untranslated region containing the polyadenylation site for the heavy chain of the secreted form of IgG1.
   The nucleotide sequence of the heavy chain constant region is reported in SEQ ID NO: 16. The amino acid sequence of the γ-chain constant region encoded by plasmid pIgG is reported in SEQ ID NO: 17.
2. A transcription unit for a human kappa (κ) light chain, composed of
   the immediate early enhancer and promoter from the human cytomegalovirus (hCMV),
   a synthetic 5' untranslated region including a Kozak consensus sequence,
   a murine immunoglobulin heavy chain signal sequence including the signal sequence intron,
   a variable κ chain cDNA of an antibody with binding specificity against said proteinaceous antigen,
   the mouse intron 2 Ig κ enhancer joined with the human immunoglobulin kappa constant (IGKC) gene, and
   the human IGKC gene 3' untranslated region containing the polyadenylation site.
3. A neomycin phosphotransferase transcription unit as a selectable marker for mammalian cells.
4. An origin of replication from the plasmid pUC18 for the replication of the plasmid in *E. coli*.
5. A beta-lactamase gene conferring ampicillin resistance in *E. coli*.

b) Construction of the sIgG/mIgG Expression Plasmid pmIgG

A 5.2 kb genomic fragment of the human immunoglobulin heavy constant gamma 1 (IGHG1) locus comprising the main part of the intron downstream of exon CH3 (intron 6), the exon M1, the intron downstream of exon M1 (intron 7), the exon M2, and the adjacent 3' untranslated region (3'UTR), including the polyadenylation signal for the membrane bound form of the gamma 1 chain, was amplified from human genomic DNA (Roche Diagnostics GmbH, Mannheim, Germany) by PCR using the Expand Long Template PCR System (Roche Diagnostics GmbH, Germany) and the oligonucleotide primer specified in the following Table.

| use for | name | sequence (in 5' to 3' direction) | SEQ ID NO: |
|---|---|---|---|
| amplification of 5.2 kb genomic IGHG1 fragment | TM-fw1 | GGCCGAGTCTGAGGCCTG AGTGGCATGAGGGAGGCA GAGT | 18 |
| | TM-rv1 | AACTGGATCCATGTAGAA AAGAGGAGAAGCCCCGGG GGTCCATGTAGT | 19 |
| amplification of 1.1 kb genomic IGHG3 fragment | TM-fw1 | GGCCGAGTCTGAGGCCTG AGTGGCATGAGGGAGGCA GAGT | 18 |
| | M1-rv | GATCCACTTCACCTTGAA GAAGGTGACGGTGGCACT GTAGCACACGC | 20 |
| amplification of 1.6 kb genomic IGHG4 fragment | M2-fw | CACCTTCTTCAAGGTGAA GTGGATCTTCTCCTCGGT GGTGGACCTGAAG | 21 |
| | TM-rv1 | AACTGGATCCATGTAGAA AAGAGGAGAAGCCCCGGG GGTCCATGTAGT | 19 |
| amplification of the joined IGHG3-IGHG4 fragment | TM-fw2 | CTCCAGCAGCAGCTGCCC TGGGCTGGGCCACGA | 22 |
| | TM-rv2 | CAGGGATCCCCGAGGTG CAGCTGGACCAGCCTCCT CCTGACCGTGTTTT | 23 |
| mutation of the Sph I site in the 3'UTR | mutSphI-1 | CTACCCCAGACCTCCGCT GCTTGGTGCcTGCAGGGC ACTGGGGGCCAGGTGTCC CCTCAGCAGGACGT* | 24 |
| | mutSphI-2 | CCTGCTGAGGGGACACCT GGCCCCCAGTGCCCTGCA gGCACCAAGCAGCGGAGG TCTGGGGT* | 25 |

*The altered nucleotides for the mutagenesis of the Sph I site are indicated by lower case letters.

The amplified fragment corresponds to the nucleotides 87203513-87208691 of the "*Homo sapiens* chromosome 14 genomic contig" (NCBI accession: NT_026437, reverse complement). Sequencing of the subcloned PCR product revealed an identity of 98 percent compared to the corresponding chromosome 14 sequence with all differences found in introns or the 3' untranslated region (3'UTR). The Sph I restriction site 219 bp downstream of the exon M2 stop codon was destroyed by PCR based site directed mutagenesis using the oligonucleotide primers specified in the Table above. The fragment was then joined with the 5' flanking part of intron 6 by cloning via a Sph I restriction site into the immunoglobulin gamma 1 chain expression plasmid pIgG, thus leading to a complete genomically organized gamma 1 chain transcription unit. By sub-cloning the eukaryotic expression plasmid pmIgG was constructed that codes for the secreted form (sIgG) and the membrane bound form (mIgG) of an antibody with binding specificity against a proteinaceous antigen. The plasmid contains the following elements:

1. The afore mentioned transcription unit for a human gamma 1 heavy chain, composed of
   the immediate early enhancer and promoter from the human cytomegalovirus (hCMV),
   a synthetic 5' untranslated region including a Kozak consensus sequence,
   a murine immunoglobulin heavy chain signal sequence including the signal sequence intron,
   a variable heavy chain cDNA of an antibody with binding specificity against a proteinaceous antigen,
   a mouse/human heavy chain hybrid intron 2 including the mouse Ig miu (μ) enhancer from the JH3-JH4 switch region (Banerji, J., et al., Cell 33 (1983) 729-740; Gillies, S. D., et al., Cell, 33 (1983) 717-728) joined It is to be understood that modifications can be made in the procedures set forth without departing from the spirit of the invention.

with the human immunoglobulin heavy constant gamma 1 (IGHG1) gene including the exons from CH1 to M2 with all intervening introns, the polyadenylation site for the secreted form of IgG1 in intron 6, and the 3'UTR containing the polyadenylation site for the membrane bound form of IgG1.

The nucleotide sequence of the genomically organized heavy chain constant region is reported in SEQ ID NO: 26. The amino acid sequences of the short (sIgG) isoform or the long (mIgG) isoform of the γ-chain constant region encoded by plasmid pmIgG are reported in SEQ ID NO: 27 or SEQ ID NO: 28, respectively.

2. A transcription unit for a human kappa (κ) light chain, composed of
   the immediate early enhancer and promoter from the human cytomegalovirus (hCMV),
   a synthetic 5' untranslated region including a Kozak consensus sequence,
   a murine immunoglobulin heavy chain signal sequence including the signal sequence intron,
   a variable κ chain cDNA of an antibody with binding specificity against a proteinaceous antigen,
   the mouse intron 2 Ig κ enhancer (Emorine, L., et al., Nature 304 (1983) 447-449; Picard, D., and Schaffner, W., Nature (1984) 307, 80-82) joined with the human immunoglobulin κ constant (IGKC) gene, and
   the human IGKC gene 3'UTR containing the polyadenylation site.
3. A neomycin phosphotransferase transcription unit as a selectable marker for mammalian cells.
4. An origin of replication from the plasmid pUC18 for the replication of the plasmid in *E. coli*.
5. A beta(β)-lactamase gene conferring ampicillin resistance in *E. coli*.

c) Construction of the sIgG/mIgG Expression Plasmid pmIgGΔ-B

Figure 12:
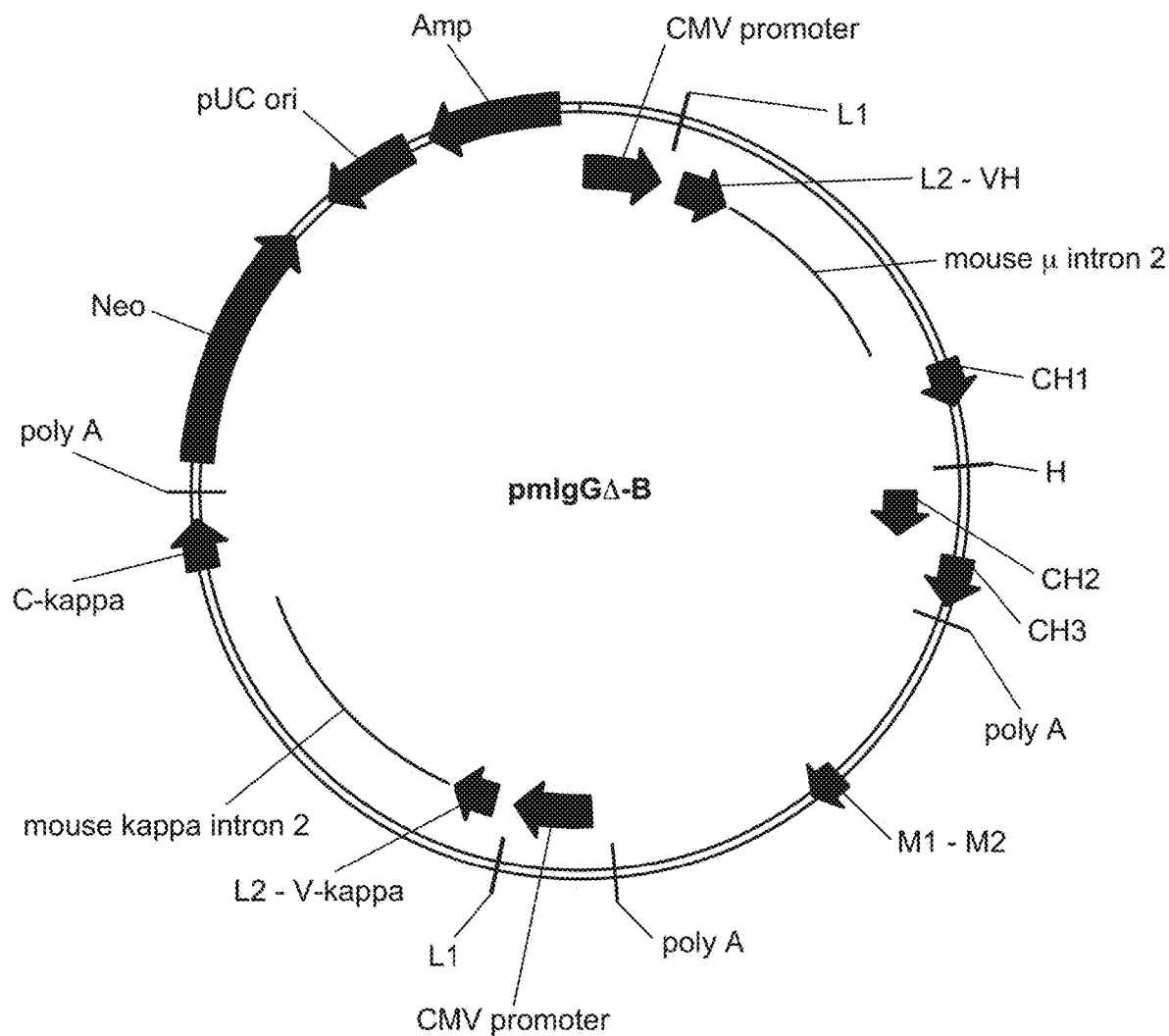
FIG. 12: Plasmid map of pmIgGΔ-B.

In a similar way as described in Example 1b), a 1.1 kb genomic fragment of the human immunoglobulin heavy constant gamma 3 (IGHG3) locus comprising the main part of the intron downstream of exon $C_H3$ (intron 6), and the exon M1 was PCR amplified (for oligonucleotides see Table above). The fragment corresponds to the nucleotides 87235195-87236300 of the "*Homo sapiens* chromosome 14 genomic contig" (NCBI accession: NT_026437, reverse complement), with a sequence identity of 98 percent. All differences are found within the intron except for one single nucleotide exchange within exon M1 that is silent, thus does not change the encoded amino acid sequence. Similarly, a 1.6 kb genomic fragment of the human immunoglobulin heavy constant gamma 4 (IGHG4) locus comprising exon M2 and the adjacent 3' untranslated region including the polyadenylation signal for the membrane bound form of the gamma 4 chain was PCR amplified (for oligonucleotides see Table above). The fragment corresponds to the nucleotides 87087786-87089377 of the "*Homo sapiens* chromosome 14 genomic contig" (NCBI accession: NT_026437, reverse complement), with a sequence identity of 98 percent and all differences found in the 3'UTR. The Sph I site 212 bp downstream of the exon M2 stop codon was destroyed by PCR based site directed mutagenesis. Both fragments were joined between M1 and M2, amplified by PCR (for oligonucleotides see Table above) and then cloned into the gamma 1 chain expression plasmid by a Sph I site in intron 6, thereby leading to a hybrid gamma 1-gamma 3-gamma 4 chain expression cassette with a genomic organization lacking the intron between M1 and M2 (intron 7). By subcloning the eukaryotic expression plasmid pmIgGΔ-B was constructed that codes for the secreted sIgG and the membrane bound mIgG form of an antibody with binding specificity against a proteinaceous antigen. The plasmid contains the following elements (see also FIG. 12):

1. The aforementioned transcription unit for a hybrid gamma 1-gamma 3-gamma 4 heavy chain, composed of
   the immediate early enhancer and promoter from the human cytomegalovirus (hCMV),
   a synthetic 5' untranslated region including a Kozak consensus sequence,
   a murine immunoglobulin heavy chain signal sequence including the signal sequence intron,
   a variable heavy chain cDNA of an antibody with binding specificity against a proteinaceous antigen,
   a mouse/human heavy chain hybrid intron 2 including the mouse Ig t enhancer ($J_H3$-$J_H4$ switch region) joined with the human IGHG1 gene including the exons from CH1 to CH3 with all intervening introns, and the adjacent 5' part of intron 6 including the polyadenylation site for the secreted form of the immunoglobulin,
   the 3' part of intron 6 and exon M1 from the human IGHG3 gene, and
   the exon M2 and the 3' untranslated region containing the polyadenylation site for the membrane bound form of the immunoglobulin from the human IGHG4 gene.

Figure 13:
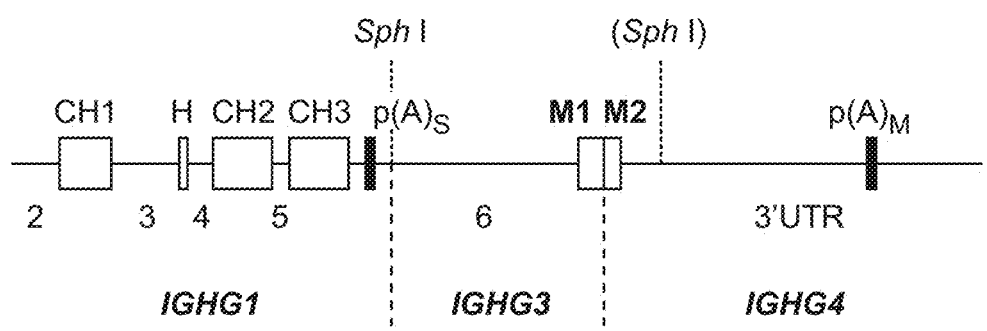
FIG. 13: Map of the genomic organization of the heavy chain constant region.

The genomic organization of the heavy chain constant region is depicted in FIG. 13, the nucleotide sequence is reported in SEQ ID NO: 06. The amino acid sequences of the short (sIgG) isoform or the long (mIgG) isoform of the γ-chain constant region encoded by plasmid pmIgGΔ-B are reported in SEQ ID NO: 07 or SEQ ID NO: 08, respectively.

2. A transcription unit for a human kappa light chain, composed of
   the immediate early enhancer and promoter from the human cytomegalovirus (hCMV),
   a synthetic 5' UTR including a Kozak consensus sequence,
   a murine immunoglobulin heavy chain signal sequence including the signal sequence intron,
   a variable κ chain cDNA of an antibody with binding specificity against a proteinaceous antigen,
   the mouse intron 2 Ig κ enhancer joined with the human immunoglobulin κ constant (IGKC) gene, and
   the human IGKC gene 3' untranslated region containing the polyadenylation site.
3. A neomycin phosphotransferase transcription unit as a selectable marker for mammalian cells.
4. An origin of replication from the plasmid pUC18 for the replication of the plasmid in *E. coli*.
5. A beta-lactamase gene conferring ampicillin resistance in *E. coli*.

d) Construction of the sIgG/mIgG Expression Plasmids for sIgG/mIgG with 3'-Splice Site Mutations pmIgGΔ-Mut-Bp, pmIgGΔ-Mut-p(Y), pmIgGΔ-Mut-Bp-p(Y)

Three expression plasmids were designed that differ from plasmid pmIgGΔ-B by point mutations within the 3'-splice site region of heavy chain intron 6. For the generation of plasmid 'pmIgGΔ-mut-bp' two base pairs near the branch point were exchanged. For plasmid 'pmIgGΔ-mut-p(Y)' four base pairs within the polypyrimidine tract were exchanged. And for plasmid 'pmIgGΔ-mut-bp-p(Y)' both, the branch point and the polypyrimidine tract mutations were combined. All mutations were inserted into pmIgGΔ-B by standard site-directed mutagenesis and cloning procedures. The DNA sequence of that region in plasmid pmIgGΔ-B and the inserted mutations in the plasmids pmIgGΔ-mut-bp, pmIgGΔ-mut-p(Y) and pmIgGΔ-mut-bp-p(Y) are listed in the following Table (mutated base pairs are highlighted in bold; the upper row shows the position of the 3'-fragment of intron 6, the 3'-splice site (depicted by vertical line) and the 5'-fragment of exon M1-M2; the bottom row shows the consensus sequence of that region including the branch point, the polypyrimidine tract and the 3'-splice site as reported by Zhang, M., Hum. Mol. Genet 7 (1998) 919)

```
                          .........intron 6..........|exon M1-M2
pmIgGΔ-B              5'...CAGCACTGACCACCCCCTTCCTGTCCAG|AGCTG...3'
(SEQ ID NO: 01)
pmIgGΔ-mut-bp         5'...CAGCACCTACCACCCCCTTCCTGTCCAG|AGCTG...3'
(SEQ ID NO: 02)
pmIgGΔ-mut-p(Y)       5'...CAGCACTGACCACGCCAATCGTGTCCAG|AGCTG...3'
(SEQ ID NO: 03)
pmIgGΔ-mut-bp-p(Y)    5'...CAGCACCTACCACGCCAATCGTGTCCAG|AGCTG...3'
(SEQ ID NO: 04)
3'-splice site                  nnYTVAy       yyyyyyyyyyynYAG | gt
consensus sequence              |             |_____|   |
(SEQ ID NO: 05)            branch point      poly(Y) tract   3'-splice site
``` e) Construction of the sIgG/mIgG Expression Plasmids for sIgG/mIgG with 3'-Splice Site Mutations pmIgGΔ-Mut-ESE The DNA sequence of 50 base pairs from plasmid pmIgGΔ-B was analyzed to identify putative exonic splice enhancer (ESE) sites. The region spans the last eight base pairs of intron 6 and the 42 adjacent base pairs of exon M1-M2 in 5'-3'-direction. Putative ESE sites for the human SR proteins SF2/ASF, SC35, SRp40 and SRp55 were sought using the computer program 'ESEfinder' (L. Cartegni et al., Nucleic Acids Res 31, 3568 (2003). The program identified 11 putative ESE sites with a score between 2.04536 and 5.53775 as shown in the following Table (the upper part shows the 50 base pair DNA sequence around the 5' end of exon M1-M2 in plasmid pmIgGΔ-B; the lower part shows the identified putative ESE sites in that region for four human SR proteins, the position and DNA sequence and a valuation by score).

| pmIgGΔ-B sequence analyzed by ESEfinder |  |  |  |
|---|---|---|---|
| 10        20        30        40        50 | | | |
| CTGTCCAG\|AGCTGCAACTGGAGGAGAGCTGTGCGGAGGCGCAGGACGGGG | | | |
| Intron 6\| Exon M1-M2                (SEQ ID NO: 09) | | | |

| Putative ESE sites for human SR proteins | | | |
|---|---|---|---|
| SR protein | Position | Site | Score |
| SF2/ASF | 6 | CAGAGCT | 2.80777 |
| SF2/ASF | 18 | TGGAGGA | 2.34103 |
| SF2/ASF | 30 | GTGCGGA | 2.04536 |
| SF2/ASF | 33 | CGGAGGC | 3.08488 |
| SF2/ASF | 39 | CGCAGGA | 5.53775 |
| SF2/ASF | 42 | AGGACGG | 2.66367 |
| SC35 | 3 | GTCCAGAG | 3.39314 |
| SRp40 | 5 | CCAGAGC | 3.40075 |
| SRp40 | 14 | CAACTGG | 3.45527 |
| SRp55 | 12 | TGCAAC | 2.92201 |
| SRp55 | 31 | TGCGGA | 4.95677 |

Nine base pair exchanges were identified in silico that remove putative ESE sites. It was thereby taken into account to choose silent mutations that do not alter the amino acid sequence encoded by exon M1-M2. The modified sequence was analyzed with the ESEfinder program. Compared to the unmodified sequences only 2 putative ESE sites were identified with a score lower than 3. Based on these in silico results the 9 base pairs were exchanged in plasmid pmIgGΔ-B using standard methods for site directed mutagenesis and DNA cloning. The modified plasmid was called pmIgGΔ-mut-ESE. The following Table shows the modified sequence and the ESEfinder program results (the upper part shows the 50 base pair DNA sequence around the 5' end of exon M1-M2 in plasmid pmIgGΔ-mut-ESE; the nine mutated base pairs compared to pmIgGΔ-B are highlighted in bold; the lower part shows the identified putative ESE sites in that region for four human SR proteins, the position and DNA sequence and a valuation by score).

| pmIgGΔ-mut-ESE sequence analyzed by ESEfinder | | | |
|---|---|---|---|
| 10        20        30        40        50 | | | |
| CTGTCCAG\|AATTGCAATTGGAAGAGAGCTGTGCTGAAGCTCAAGATGGGG | | | |
| Intron 6\| Exon M1-M2                (SEQ ID NO: 10) | | | |

| Putative ESE sites for human SR proteins | | | |
|---|---|---|---|
| SR protein | Position | Site | Score |
| SF2/ASF | 39 | CTCAAGA | 2.94284 |
| SC35 | 3 | GTCCAGAA | 2.94325 | f) Construction of the sIgG/mIgG Expression Plasmid with Additional Poly(A) Sites in Intron 6pmIgGΔ-SV40-p(A)

For the biosynthesis of sIgG the pre-mRNA of the heavy chain is polyadenylated at the polyadenylation site within intron 6. This step competes against the removal of intron 6 by splicing for generating the mIgG isoform. To foster the early polyadenylation an additional polyadenylation site was added into intron 6.

For cloning of plasmid pmIgGΔ-SV40-p(A) a fragment of 153 bp containing the early polyadenylation site of simian virus 40 (SV40) was inserted into intron 6 of plasmid pmIgGΔ-B, 71 bp downstream of the stop codon of exon CH3. Comparably, plasmid pmIgGΔ-BGH-p(A) was cloned by inserting a 237 bp fragment containing the polyadenylation site of the bovine growth hormone (BGH) in plasmid pmIgGΔ-B at the same position. The plasmids were constructed with standard molecular biological methods.

FIG. 1 gives an overview of the intron 6 region of the heavy chain in pmIgGΔ-B and the position of the modified features of the plasmids described above.

Construction of Expression Vectors with Intracellular Selection Markers Linked to Membrane Bound IgG g) Expression Plasmid for Antibody Light Chain The plasmid pIgG-LC was constructed to express an antibody light chain. It comprises the following elements:
1. A transcription unit for the light chain of an antibody specifically binding to a proteinaceous antigen composed of:
   1.1 the immediate early enhancer and promoter from the human cytomegalovirus (hCMV)
   1.2 the 5' untranslated region of the human immunoglobulin kappa variable 3-11 (IGKV3-11) gene
   1.3 the coding sequence of an immunoglobulin kappa light chain comprising:
      1.3.1 the cDNA of the leader peptide of IGKV3-11
      1.3.2 a variable light chain cDNA of an antibody specifically binding to a proteinaceous antigen,
      1.3.3 the cDNA of the human immunoglobulin kappa constant (IGKC) gene
   1.4 the 3' untranslated region containing the polyadenylation site of IGKC.
2. An origin of replication from plasmid pUC18 for the replication of the plasmid in *E. coli*.
3. A beta-lactamase gene conferring ampicillin resistance in *E. coli*.

h) Expression Plasmid for sIgG and mIgG-Puro Fusion Protein

The plasmid pmIgG-Puro-mut-p(Y) was designed to express the sIgG form of the antibody specifically binding to a proteinaceous antigen and a transmembrane fusion variant thereof. This variant comprises the same light chain as the sIgG form and a fusion protein comprising the mIgG heavy chain and the Puromycin-N-acetyltransferase. These two antibody forms should arise by alternative processing of the pre-mRNA of the heavy chain fusion protein as described for mIgG. Additionally, the polypyrimidine tract of intron 6 of the heavy chain was mutated by exchange of four base pair as described for expression plasmid pmIgGΔ-mut-p(Y) see above.

The plasmid pmIgG-Puro-mut-p(Y) consists of the following elements:
1. The transcription unit for the aforementioned sIgG heavy chain or the fusion protein of the mIgG heavy chain and the Puromycin-N-acetyltransferase, composed of:
   1.1 the immediate early enhancer and promoter from the human cytomegalovirus (hCMV),
   1.2 a synthetic 5' untranslated region including a Kozak consensus sequence,
   1.3 a murine immunoglobulin heavy chain signal sequence including the signal sequence intron,
   1.4 a variable heavy chain cDNA of an antibody specifically binding to a proteinaceous antigen,
   1.5 a mouse/human heavy chain hybrid intron 2 including the mouse Ig enhancer (JH3-JH4 switch region) joined with the human IGHG1 gene including the exons from CH1 to CH3 with all intervening introns, and the adjacent 5' part of intron 6 including the polyadenylation site for the secreted form of the immunoglobulin,
   1.6 the 3' part of intron 6 from the human IGHG3 gene, including four base pair exchanges within the polypyrimidine tract as listed in the Table below for plasmid pmIgGΔ-mut-p(Y),
   1.7 exon M1 from the human IGHG3 gene, linked to
   1.8 exon M2 from the human IGHG4 gene, linked to
   1.9 Puromycin-N-acetyltransferase cDNA,
   1.10 the polyadenylation site of simian virus 40.
2. A transcription unit for a human kappa light chain, composed of
   2.1 the immediate early enhancer and promoter from the human cytomegalovirus (hCMV),
   2.2 a synthetic 5' untranslated region including a Kozak consensus sequence,
   2.3 a murine immunoglobulin heavy chain signal sequence including the signal sequence intron,
   2.4 a variable κ chain cDNA of an antibody specifically binding to a proteinaceous antigen,
   2.5 the mouse intron 2 Ig κ enhancer joined with the human immunoglobulin κ constant (IGKC) gene, and
   2.6 the human IGKC gene 3' untranslated region containing the polyadenylation site.
3. An origin of replication from the plasmid pUC18 for the replication of the plasmid in *E. coli*.
4. A beta-lactamase gene conferring ampicillin resistance in *E. coli*.

The construction of the plasmid pmIgG-Puro-mut-p(Y) is depicted in FIG. 6.

i) Expression Plasmid for sIgG and Puromycin-N-Acetyltransferase

The plasmid pIgG-Puro was designed as control plasmid to express the sIgG form of the antibody specifically binding to a proteinaceous antigen, and the puromycin-N-acetyltransferase encoded by an independent expression cassette. It comprises the following elements:
1. The transcription unit for the sIgG heavy chain, composed of:
   1.1 the immediate early enhancer and promoter from the human cytomegalovirus (hCMV),
   1.2 a synthetic 5' untranslated region including a Kozak consensus sequence,
   1.3 a murine immunoglobulin heavy chain signal sequence including the signal sequence intron,
   1.4 a variable heavy chain cDNA of an antibody specifically binding to a proteinaceous antigen,
   1.5 a mouse/human heavy chain hybrid intron 2 including the mouse Ig enhancer (JH3-JH4 switch region) joined with the human IGHG1 gene including the exons from $C_H1$ to $C_H3$ with all intervening introns, and the adjacent 3' untranslated region containing the polyadenylation site for the heavy chain of the secreted form of IgG1.
2. A transcription unit for a human kappa light chain, composed of
   2.1 the immediate early enhancer and promoter from the human cytomegalovirus (hCMV),
   2.2 a synthetic 5' untranslated region including a Kozak consensus sequence,
   2.3 a murine immunoglobulin heavy chain signal sequence including the signal sequence intron,
   2.4 a variable κ chain cDNA of an antibody specifically binding to a proteinaceous antigen,
   2.5 the mouse intron 2 Ig κ enhancer joined with the human immunoglobulin κ constant (IGKC) gene, and
   2.6 the human IGKC gene 3' untranslated region containing the polyadenylation site.
3. A puromycin-N-acetyltransferase transcription unit as a selectable marker for mammalian cells, containing an SV40 promoter, the puromycin-N-acetyltransferase cDNA and the SV40 polyadenylation site.
4. An origin of replication from the plasmid pUC18 for the replication of the plasmid in *E. coli*.
5. A beta-lactamase gene conferring ampicillin resistance in *E. coli*.

The construction of the plasmid pIgG-Puro is depicted in FIG. 7.

j) Expression Plasmid for sIgG and Neomycin Phosphotransferase

The plasmid pIgG-Neo was designed to generate an improved expression cell line on a conventional way as described in example 6. The plasmid codes for the heavy and the light chain of the sIgG isoform of the antibody specifically binding to a proteinaceous antigen, and the neomycin phosphotransferase encoded by an independent expression cassette. It comprises the following elements:

1. The transcription unit for the sIgG heavy chain, composed of:
   1.1 the immediate early enhancer and promoter from the human cytomegalovirus (hCMV),
   1.2 a synthetic 5' untranslated region including a Kozak consensus sequence,
   1.3 a murine immunoglobulin heavy chain signal sequence including the signal sequence intron,
   1.4 a variable heavy chain cDNA of an antibody specifically binding to a proteinaceous antigen,
   1.5 a mouse/human heavy chain hybrid intron 2 including the mouse Ig enhancer (JH3-JH4 switch region) joined with the human IGHG1 gene including the exons from CH1 to CH3 with all intervening introns, and the adjacent 3' untranslated region containing the polyadenylation site for the heavy chain of the secreted form of IgG1.
2. A transcription unit for a human kappa light chain, composed of
   2.1 the immediate early enhancer and promoter from the human cytomegalovirus (hCMV),
   2.2 a synthetic 5' untranslated region including a Kozak consensus sequence,
   2.3 a murine immunoglobulin heavy chain signal sequence including the signal sequence intron,
   2.4 a variable κ chain cDNA of an antibody specifically binding to a proteinaceous antigen,
   2.5 the mouse intron 2 Ig κ enhancer joined with the human immunoglobulin κ constant (IGKC) gene, and
   2.6 the human IGKC gene 3' untranslated region containing the polyadenylation site.
3. A neomycin phosphotransferase transcription unit as a selectable marker for mammalian cells, containing an SV40 promoter, the neomycin phosphotransferase cDNA and the SV40 polyadenylation site.
4. An origin of replication from the plasmid pUC18 for the replication of the plasmid in *E. coli*.
5. A beta-lactamase gene conferring ampicillin resistance in *E. coli*.

The construction of the plasmid pIgG-Neo is depicted in FIG. 8.

k) Expression Plasmid for mIgG and Neomycin Phosphotransferase

The plasmid codes for the heavy chain of the sIgG isoform of the antibody specifically binding to a proteinaceous antigen, and the neomycin phosphotransferase encoded by an independent expression cassette. It comprises the following elements (see FIG. 3):

1. A transcription unit for the fusion protein of the mIgG form of the heavy chain linked to neomycin phosphotransferase, composed of:
   1.1 the immediate early enhancer and promoter from the human cytomegalovirus (hCMV)
   1.2 the 5' untranslated region of the human immunoglobulin heavy variable 3-33 gene (IGHV3-33).
   1.3 the coding sequence of a fusion protein comprising:
      1.3.1 the cDNA of the leader peptide (L) of IGHV3-33
      1.3.2 a variable heavy chain cDNA (VH) of an antibody specifically binding to a proteinaceous antigen
      1.3.3 the cDNA of the human immunoglobulin heavy constant gamma 1 gene (IGHG1) from exon $C_H1$ to $C_H3$
      1.3.4 the cDNA of exon M1 of the human immunoglobulin heavy constant gamma 3 gene (IGHG3)
      1.3.5 the cDNA of exon M2 of the human immunoglobulin heavy constant gamma 4 gene (IGHG4)
      1.3.6 the cDNA coding for the neomycin phosphotransferase (Neo)
   1.4 the polyadenylation site of simian virus 40 (SV40 poly(A)).
2. An origin of replication from plasmid pUC18 (pUC ori) for the replication of the plasmid in *E. coli*.
3. A beta-lactamase gene (Amp) conferring ampicillin resistance in *E. coli*.

l) Expression Plasmid for mIgG and Hygromycin Phosphotransferase

The plasmid codes for the heavy chain of the sIgG isoform of the antibody specifically binding to a proteinaceous antigen, and the hygromycin phosphotransferase encoded by an independent expression cassette. It comprises the following elements (see FIG. 4):

1. A transcription unit for the fusion protein of the mIgG form of the heavy chain linked to neomycin phosphotransferase, composed of:
   1.1 the immediate early enhancer and promoter from the human cytomegalovirus (hCMV)
   1.2 the 5' untranslated region of the human immunoglobulin heavy variable 3-33 gene (IGHV3-33).
   1.3 the coding sequence of a fusion protein comprising:
      1.3.1 the cDNA of the leader peptide (L) of IGHV3-33
      1.3.2 a variable heavy chain cDNA (VH) of an antibody specifically binding to a proteinaceous antigen
      1.3.3 the cDNA of the human immunoglobulin heavy constant gamma 1 gene (IGHG1) from exon CH1 to CH3
      1.3.4 the cDNA of exon M1 of the human immunoglobulin heavy constant gamma 3 gene (IGHG3)
      1.3.5 the cDNA of exon M2 of the human immunoglobulin heavy constant gamma 4 gene (IGHG4)
      1.3.6 the cDNA coding for the hygromycin phosphotransferase (Hyg)
   1.4 the polyadenylation site of simian virus 40 (SV40 poly(A)).
2. An origin of replication from plasmid pUC18 (pUC ori) for the replication of the plasmid in *E. coli*.
3. A beta-lactamase gene (Amp) conferring ampicillin resistance in *E. coli*.

m) Expression Plasmid for mIgG and Puromycin-N-Acetyltransferase

The plasmid codes for the heavy chain of the sIgG isoform of the antibody specifically binding to a proteinaceous antigen, and the neomycin phosphotransferase encoded by an independent expression cassette. It comprises the following elements (see FIG. 5):

1. A transcription unit for the fusion protein of the mIgG form of the heavy chain linked to neomycin phosphotransferase, composed of:
   1.1 the immediate early enhancer and promoter from the human cytomegalovirus (hCMV)
   1.2 the 5' untranslated region of the human immunoglobulin heavy variable 3-33 gene (IGHV3-33).

1.3 the coding sequence of a fusion protein comprising:
  1.3.1 the cDNA of the leader peptide (L) of IGHV3-33
  1.3.2 a variable heavy chain cDNA (VH) of an antibody specifically binding to a proteinaceous antigen
  1.3.3 the cDNA of the human immunoglobulin heavy constant gamma 1 gene (IGHG1) from exon $C_H1$ to $C_H3$
  1.3.4 the cDNA of exon M1 of the human immunoglobulin heavy constant gamma 3 gene (IGHG3)
  1.3.5 the cDNA of exon M2 of the human immunoglobulin heavy constant gamma 4 gene (IGHG4)
  1.3.6 the cDNA coding for the puromvcin-N-acetyl-transferase (Puro)
1.4 the polyadenylation site of simian virus 40 (SV40 poly(A)).
2. An origin of replication from plasmid pUC18 (pUC ori) for the replication of the plasmid in *E. coli*.
3. A beta-lactamase gene (Amp) conferring ampicillin resistance in *E. coli*.

Example 2

Transfection and Pool Selection

CHO-K1 cells (ATCC No. CCL-61; Puck, T. T., et al., J. Exp. Med. 108 (1958), 945-956), that have been pre-adapted to serum-free growth in suspension culture, were cultivated in ProCHO4-CDM medium (Cambrex), supplemented with 8 mM L-alanyl-L-glutamine (Invitrogen) and 1×HT supplement (Invitrogen), at 37° C., 5% $CO_2$ and 95% humidity in suspension flasks. Every 3-4 days the cells are split with $2×10^5$ cells/ml into fresh medium. For transfection, the cells are electroporated with 20 μg plasmid DNA per $7.5×10^6$ cells in a total volume of 200 μl PBS at room temperature. The electroporations are performed with a Gene Pulser XCell electroporation device (BioRad) in a 2 mm gap cuvette, using a square wave protocol with a single 160 V pulse for 15 ms. The cells were transfected with the linearized plasmids pmIgGΔ-mut-bp, pmIgGΔ-mut-p(Y), pmIgGΔ-mut-bp-p(Y), pmIgGΔ-mut-ESE, pmIgGΔ-SV40p(A), pmIgGΔ-BGH-p(A) or pmIgGΔ-B, respectively. Afterwards the cells of each transfection were cultivated as pool in the medium specified above for about three weeks with 700 μg/ml G418 (Roche Applied Science) added to the culture one day after the transfection for selection of stably transfected cells.

Example 3

Northern Blot Analysis

Figure 2B:
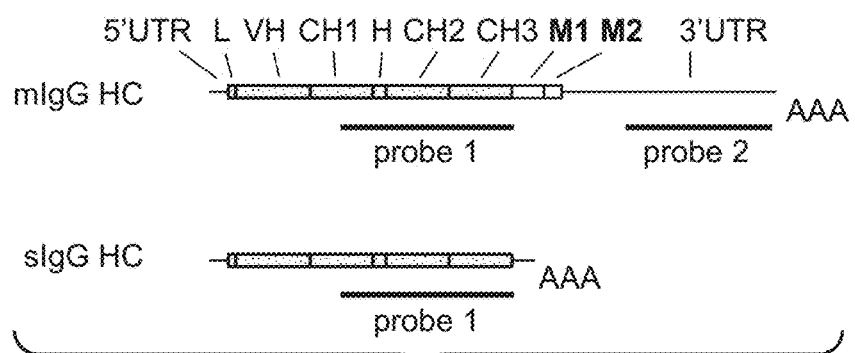

To define the ratio between the two heavy chain isoforms that emerge by alternative RNA processing of the primary transcript, RNA of stably transfected clones was analyzed by Northern blot. Therefore total RNA was isolated from the seven stably transfected cell pools as described in Example 2 using the RNeasy kit (QIAGEN). Additionally, the RNA of non-transfected CHO-K1 cells was prepared under the same conditions. In each case 10 μg of total RNA were then fractionated by denaturing agarose gel electrophoresis and transferred to a nylon membrane using the NorthernMax System (Ambion). For hybridization of the blot membrane two different DNA probes were marked with [alpha-$^{32}$P] by the random priming method using the DECAprime II kit (Ambion). As depicted in FIG. 2B, probe 1 is complementary to the heavy chain mRNA between exon CH1 and CH3 and thus hybridizes to both isoforms. In contrast, probe 2 only binds to the 3'UTR of the longer mIgG heavy chain mRNA. After hybridization and stringent washing of the membrane the blot was analyzed by autoradiography (see FIG. 2A).

The hybridization with probe 1 shows a 1.8 kb signal for the transfected cell pools, which corresponds to the short mRNA isoform that encodes the heavy chain of sIgG. In the lanes 1, 2, 4 and 7 an additional signal of 3.3 kb is detected. This band represents the long mRNA isoform for mIgG as revealed by hybridization with probe 2 (lanes 9, 10, 12 and 15). The analyzed pools differ in the relative signal strength of the 1.8 kb band to the 3.3 kb band detected by probe 1. The pool of CHO-K1 cells transfected with plasmid pmIgGΔ-B shows a ratio of about 50:50 for the two isoforms. The plasmid modifications at the 3'-splice site region of the heavy chain intron 6 influence the pre-RNA processing. For the pools transfected with pmIgGΔ-mut-bp, pmIgGΔ-mut-p(Y) or pmIgGΔ-mut-ESE a strong shift towards the sIgG isoform is observed. In the pools transfected with pmIgGΔ-mut-bp-p(Y), pmIgGΔ-SV40-p(A) or pmIgGΔ-BGH-p(A) the mIgG isoform was not detected, neither with probe 1 nor with the much more sensitive probe 2. This indicates that the modifications in those plasmids completely block the splicing of exon $C_H3$ with exon M1-M2.

Example 4

Functional Analysis of Different Markers Linked to mIgG

In this assay it was tested whether the fusion proteins of the antibody heavy chain with the neomycin, hygromycin or puromycin resistance gene are suitable as selectable marker for stable transfection. Therefore CHO K1 cells were co-transfected with the plasmid pIgG-LC to express the antibody light chain, together with pmIgG-HC-Neo, pmIgG-HC-Hyg or pmIgG-HC-Puro, respectively, to express the mIgG heavy chain fused with a selectable marker at its intracellular C-terminus. The cells were transfected using the calcium phosphate precipitation method with equimolar amounts of the co-transfected plasmids. Two days after the transfection the cells were transferred to the corresponding selection medium, containing
  600 μg/ml neomycin for co-transfection with pIgG-LC and pmIgG-HC-Neo, or
  300 μg/ml hygromycin for co-transfection with pIgG-LC and pmIgG-HC-Hyg, or
  8 μg/ml puromycin for co-transfection with pIgG-LC and pmIgG-HC-Puro.

The cells were cultivated in selection medium for about two weeks. In parallel, non-transfected CHO K1 cells were cultured in each selection medium as a control. All three transfections led to cells that stably express the respective fusion protein and survived under the selection pressure. In contrast, the non-transfected cells died completely under neomycin or puromycin selection pressure, and died partially under hygromycin selection pressure.

Example 5

Selection Pressure for Stable Transfection with Plasmid pmIgG-Puro-Mut-p(Y)

Figure 9A:
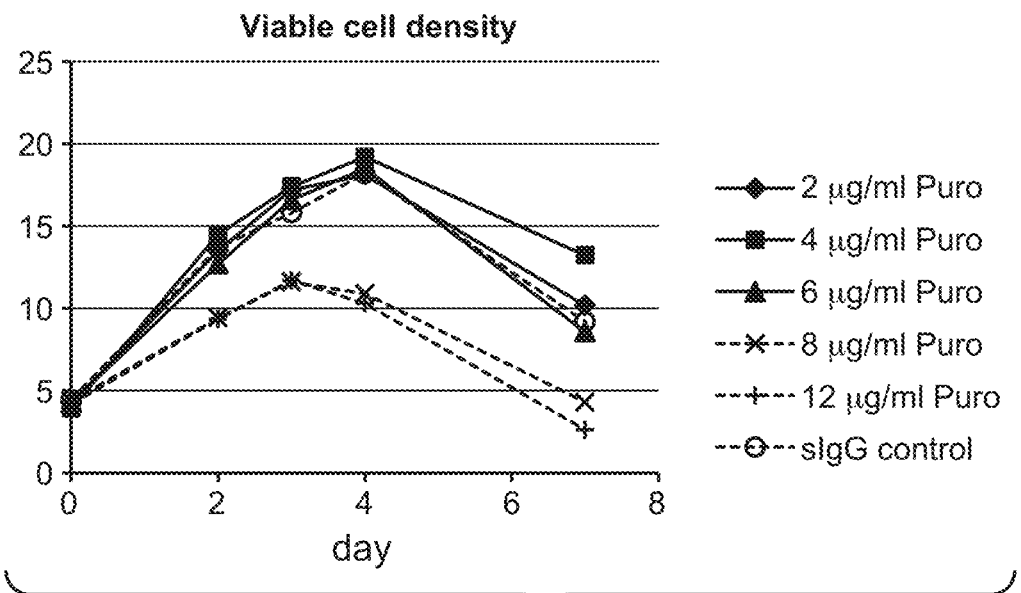
FIGS. 9A-9B: Batch assay analysis of stably transfected cell pools. The pools were seeded with 4*10⁵ cells per ml in a total volume of 30 ml and cultivated in HyQ SFM4CHO utility medium without puromycin in shaker flasks at 37° C. and 5% $CO_2$. Samples were taken at start and after 2, 3, 4 and 7 days.
Figure 9B:
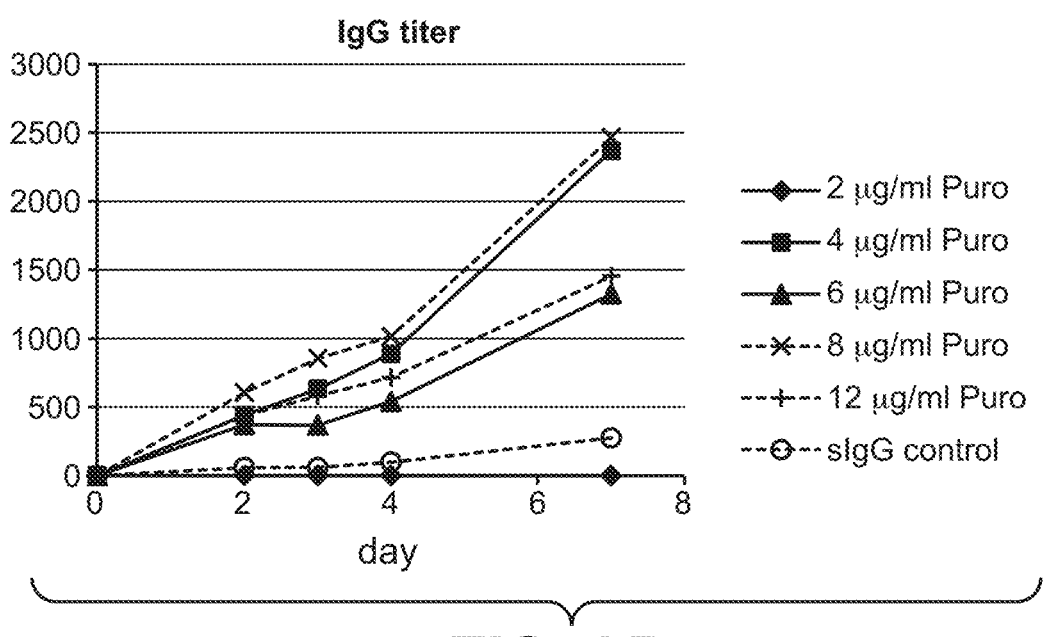

The expression plasmid pmIgG-Puro-mut-p(Y) was designed to express the sIgG form of an antibody, as well as the mIgG-Puro fusion protein. To find an appropriate selection pressure for stable transfection, CHO DG44 cells were transfected with pmIgG-Puro-mut-p(Y) by electroporation and cultivated in HyQ SFM4CHO utility medium (Hyclone) supplemented with 2% gamma-irradiated fetal bovine serum (Gibco), 4 mM Ultra glutamine (Cambrex) and HT supplement (Gibco). One day after transfection, the pmIgG-Puro-mut-p(Y) transfected cells were split into 5 different cell pools and puromycin was added with 2, 4, 6, 8 or 12 µg/ml, respectively. As a control, CHO DG44 cells were transfected with plasmid pIgG-Puro (sIgG isoform only) and cultivated with a selection pressure of 2 µg/ml puromycin. The selection pressure was kept over three week in all pools. Afterwards, the pools were further expanded in culture medium without puromycin for 12 days. To compare the pools in a batch assay, each pool was seeded with $4*10^5$ cells per ml in a total volume of 30 ml and cultivated in shaker flasks. The growth behavior was monitored by cell counting after 2, 3, 4 and 7 days (see FIG. 9A). It was observed that the cell pools generated with 2 to 6 µg/ml puromycin and the control pool grew up to a cell count greater than $1.7*10^6$ cells/ml within 4 days, whereas the pools from 8 and 12 µg/ml puromycin selection pressure showed a slower grow to a maximum of about $1.2*10^6$ cells/ml. For productivity analysis samples of each pool were taken at start and after 2, 3, 4 and 7 days. The sIgG concentration in the supernatant was determined by ELISA (see FIG. 9B). Within 7 days the control pool and the 2 g/ml puromycin pool reached a titer of less than 300 ng/ml. All other pools that were generated under higher selection pressure showed a considerably higher sIgG expression. The highest productivity was observed for the 8 µg/ml puromycin pool with a sIgG titer of 2.46 µg/ml followed by the 4 µg/ml puromycin pool with 2.36 g/ml sIgG in the supernatant. Since the 8 µg/ml puromycin pool reached a viable cell density that was about twofold lower, this means that the specific productivity of each cell was about twice as high compared to the 4 µg/ml puromycin pool.

In parallel to the batch assay, CHO DG44 cells were transfected with plasmid pmIgG-Puro-mut-p(Y) or plasmid pIgG-Puro (control) as described above and plated into 96-well microtiter plates one day after transfection. As for the cell pools, the plating medium contained 2, 4, 6, 8 or 12 µg/ml puromycin, respectively, for the pmIgG-Puro-mut-p(Y) transfected cells or 2 µg/ml puromycin for pIgG-Puro transfected cells. The cells were plated into two 96-well plates for each approach, with 1000 cells per well for 2 or 4 µg/ml puromycin selection and 2000 cells per well for 6, 8 or 12 µg/ml puromycin selection. After about two weeks the number of derived clones were counted (see the Table below). Cells transfected with pmIgG-Puro-mut-p(Y) and cultivated with medium containing 2 or 4 µg/ml puromycin generated a number of clones in the same range as for the control transfection with pIgG-Puro. Only a few clones (between 1 and 3) survived under a selection pressure of 6 µg/ml puromycin or above.

TABLE

Evaluation of puromycin selection pressure for CHO DG44 cells transfected with plasmid pmIgG-Puro-mut-p(Y).

| plasmid | IgG isoforms | puromycin [µg/ml] | # cells plated per well | # of clones in 2 96well plates |
|---|---|---|---|---|
| pmIgG-Puro-mut-p(Y) | sIgG/mIgG | 2 | 1000 | 152 |
| pmIgG-Puro-mut-p(Y) | sIgG/mIgG | 4 | 1000 | 141 |
| pmIgG-Puro-mut-p(Y) | sIgG/mIgG | 6 | 2000 | 1 |
| pmIgG-Puro-mut-p(Y) | sIgG/mIgG | 8 | 2000 | 3 |
| pmIgG-Puro-mut-p(Y) | sIgG/mIgG | 12 | 2000 | 2 |
| pIgG-Puro | sIgG | 2 | 1000 | 118 |

Taken together, 4 to 6 µg/ml puromycin was identified to be the optimal range of selection pressure for the development of CHO DG44 cell lines transfected with the pmIgG-Puro-mut-p(Y) expression plasmid. Within this range, a sufficient number of stable clones can be generated and a pool of cells shows an appropriate growth behavior and productivity.

Example 6

Improvement of an Antibody Expressing Cell Line Applying the mIgG-Puromycin Selection System
a) mIgG-Puromycin Selection System In this approach, an existing antibody expressing cell line should be improved by using the mIgG-puromycin selection system. Therefore, a suspension cell line, 1D5, was used that had been developed by stable transfection of CHO DG44 cells with a plasmid comprising three independent expression cassettes: 1. for the light chain of the antibody specifically binding to a proteinaceous antigen, 2. for the heavy chain of the antibody specifically binding to a proteinaceous antigen and, 3. for the dihydrofolate reductase as a selection marker. According to this, the stable cell line 1D5 had been generated using methotrexate (MTX) as a selective agent. The clone was cultivated in a medium containing 4 mM glutamine, 2 g/l soy peptone, 10 nM MTX, 0.1% HyQ LS1000 (cholesterol supplement) and 50 ng/ml IGF-1 Long R3 (insulin-like growth factor) in shaker flasks.

To enhance the antibody productivity, clone 2D3 was transfected with plasmid pmIgG-Puro-mut-p(Y) by electroporation. The plasmid codes for the sIgG isoform of the same antibody that is already expressed by clone 1D5. In addition, it codes for the mIgG puromycin-N-acetyltransferase fusion protein, thus, it allows the usage of puromycin as selection agent. One day after transfection, the cells were seeded into 48 96-well plates containing 4 to 6 µg/ml puromycin in the medium, with 500 to 4000 cells per well as described in the table below. Overall, 403 clones emerged under the selection pressure, most of them in the approach with the highest puromycin concentration (6 µg/ml) and the highest cell count seeded (4000 cells per well). No screening was performed to determine the antibody expression of the clones. Instead, 160 clones were selected randomly for further culture expansion: 20 clones with 4 µg/ml puromycin, 20 with 5 µg/ml, and 120 with 6 µg/ml (see the following Table).

TABLE

Distribution of stably transfected clones generated by puromycin selection in 96-well plates.

| | puromycin concentration [µg/ml] | | | | | | |
|---|---|---|---|---|---|---|---|
| | 4 | | 5 | | 6 | | total |
| # seeded cells/well | 500 | 1000 | 1000 | 2000 | 2000 | 4000 | |
| # 96-well plates | 8 | 8 | 8 | 8 | 8 | 8 | 48 |

TABLE-continued

Distribution of stably transfected clones generated
by puromycin selection in 96-well plates.

| | puromycin concentration [ug/ml] | | | | | | |
|---|---|---|---|---|---|---|---|
| | 4 | | 5 | | 6 | | total |
| # clones derived | 2 | 22 | 0 | 65 | 28 | 286 | 403 |
| # clones selected randomly for expansion | 2 | 18 20 | 0 | 20 20 | 24 | 96 120 | 160 |

Figure 10A:
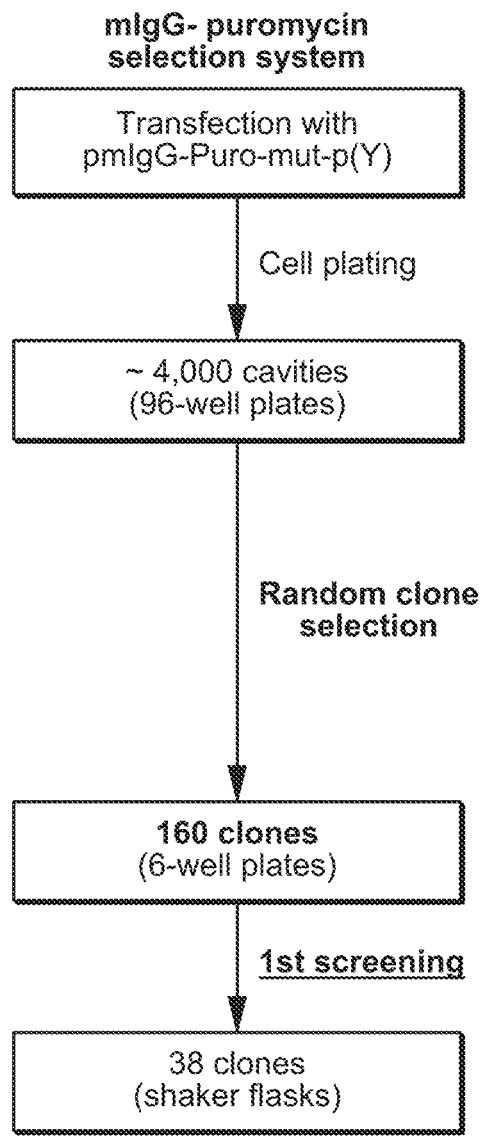
FIGS. 10A-10B: Overview mIgG-puromycin selection system and standard approach.

Growth and productivity of 152 expanded clones was assessed in a batch assay. The cells were therefore seeded with $4*10^5$ cells per ml in 4 ml medium and cultivated for 7 days in shaken 6-well plates. Samples were taken to measure the viable cell density and the sIgG titer in the supernatant. 39 of the 152 clones that showed sufficient growth and productivity were further expanded into shaker flasks and assessed in a fed batch assay (see Example 7). The workflow of the cell line developing process is depicted in FIG. 10A.

b) Standard Approach

Figure 10B:
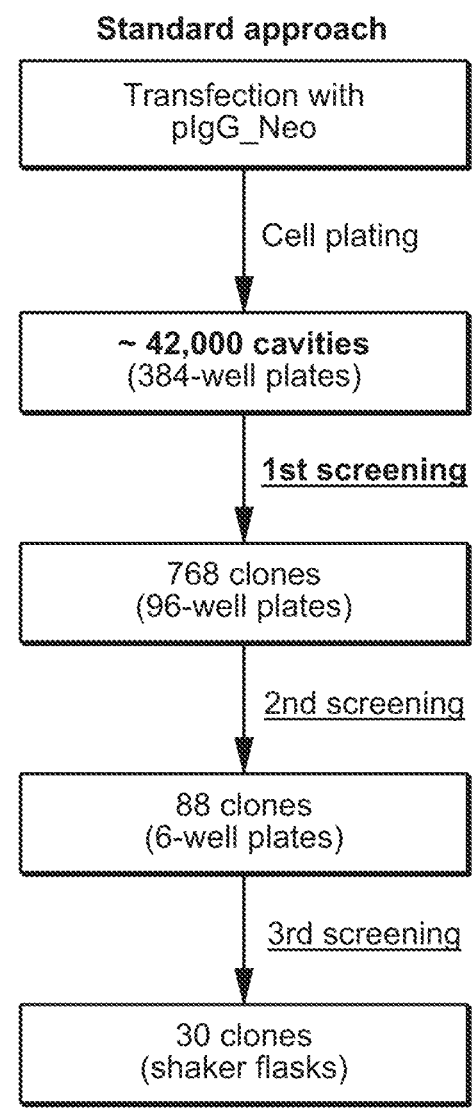

To compare the mIgG-puromycin selection system with a standard approach, clone 1D5 was transfected with plasmid pIgG-Neo to generate improved expression cell lines. The plasmid codes for the heavy and the light chain of the antibody specifically binding to a proteinaceous antigen (sIgG isoform), and the neomycin phosphotransferase as selection marker, encoded by an independent expression cassette. After transfection, the cells were plated into 120 384-well plates (~42,000 cavities seeded) and cultivated under a selection pressure of 10 nM MTX and 400 µg/ml G418. The emerging clones were assessed two weeks after transfection in a high throughput screening ELISA to measure the IgG concentration in the cell culture supernatant. Based on the results, 768 clones were transferred into 96-well plates. The clones were again screened by a high throughput ELISA and 88 clones with a high IgG titer were selected for further expansion. A third clone screening was performed with 88 clones that were seeded with a defined cell count into 6-well plates. After 7 days in culture, the IgG concentration was measured by protein A HPLC. 30 clones that showed sufficient growth and productivity were selected for cultivation up to the shaker flask format and assessed in a fed batch assay (see Example 7). The workflow of the cell line developing process is depicted in FIG. 10B.

Example 7

Figure 11A:
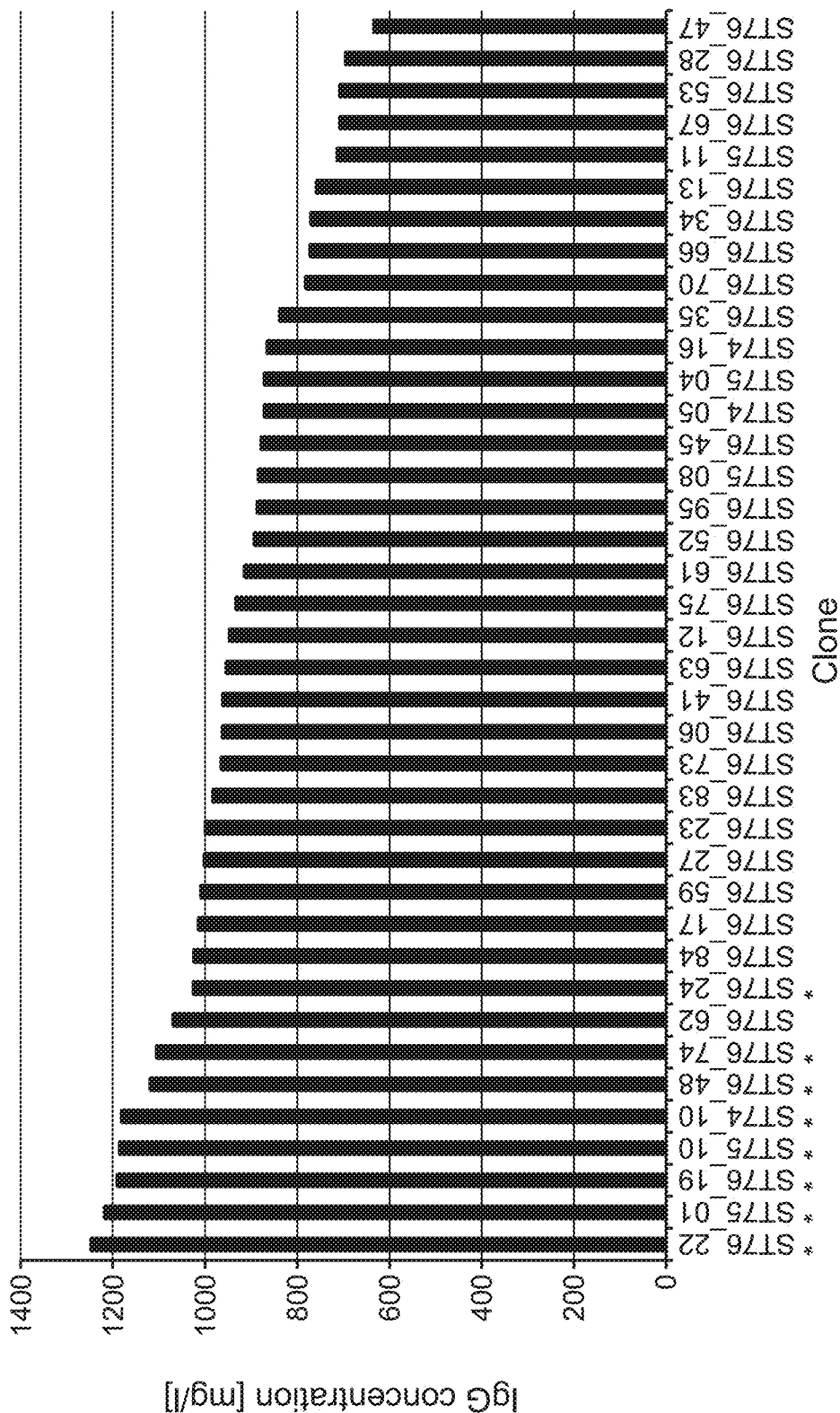
FIGS. 11A-11B: Fed batch assay. The clones were seeded and cultivated as described in Example 7. The cultivation was terminated on day 17 and the IgG concentration in the cell culture supernatants was determined by protein A HPLC analysis.
Figure 11B:
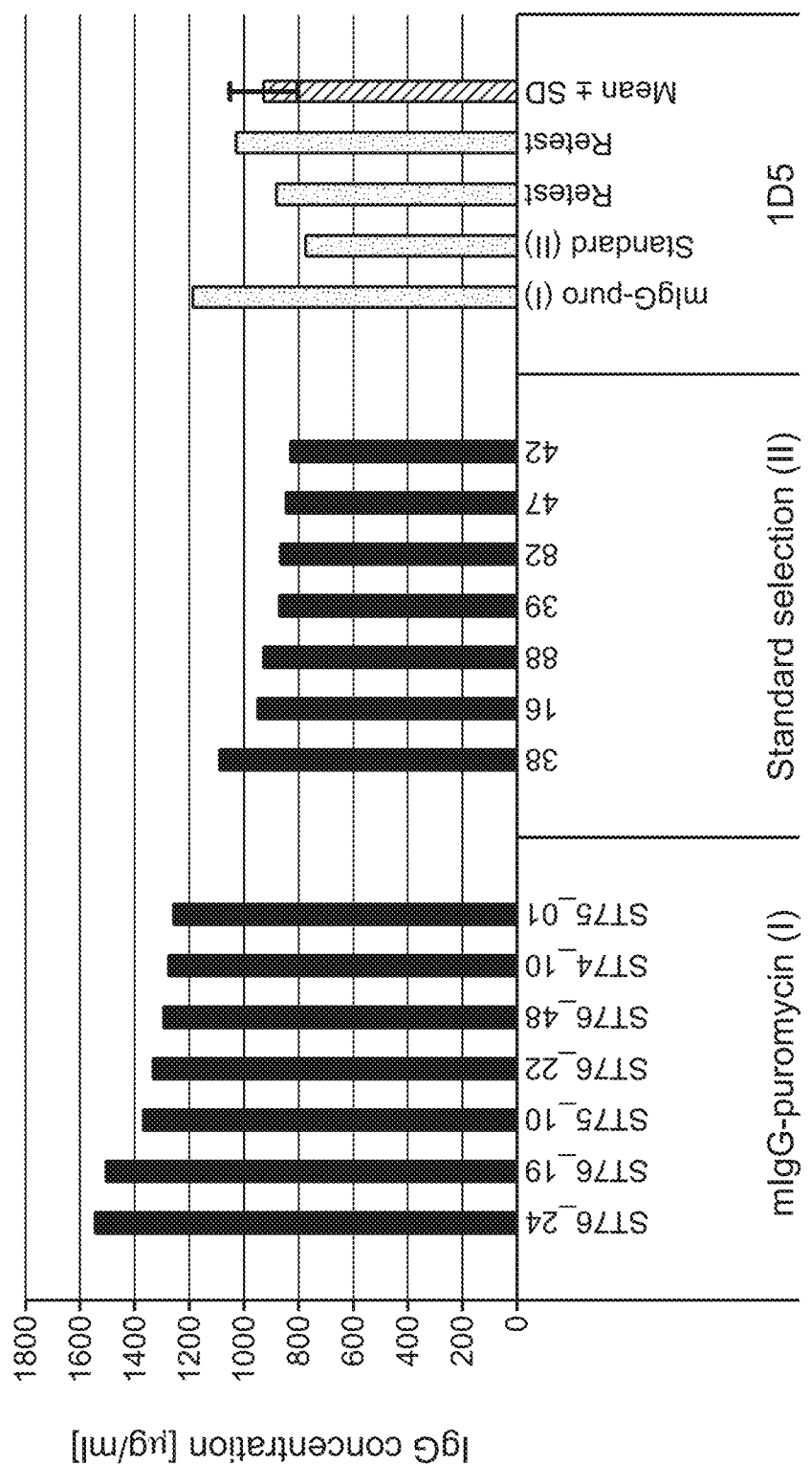

Fed Batch Analysis of Clones Generated with the mIgG-Puromycin Selection Marker 39 clones derived from the mIgG-puromycin selection process were expanded into shaker flasks (as described in Example 6) and assessed in a fed batch assay: Each cell line was seeded with $4*10^5$ cells per ml in 66 ml culture medium and cultivated under shaking conditions. Beginning three days after start, 2 ml feed was added daily to each clone. Additionally, the clones were fed with glucose to keep the concentration in the culture medium higher than 2 g/l, and glutamine to keep it higher than 0.1 g/l. Samples were taken on several days to measure the viable cell density and the sIgG titer in the supernatant. The IgG concentration was determined by protein A HPLC analysis. FIG. 11A shows the final IgG titer of all clones after 17 days in fed batch culture. Seven clones that showed high productivity were selected for further assessment. In a second fed batch assay the selected clones were analyzed in comparison with the parental clone 1D5. Again, the final titer after 17 days was determined by protein A HPLC. Likewise, the top seven clones that were generated by the standard approach (see example 6) were assessed in a fed batch assay together with 1D5 under comparable conditions. The productivity of clone 1D5 was retested in two additional fed batch runs (see FIG. 11B). All seven clones that were generated by using mIgG-puromycin as selection marker showed a clear improvement of the antibody expression compared to the parental clone 1D5. Moreover, the antibody titer of all clones was significantly higher than the titer determined for the standard approach clones. Overall, this shows a high efficiency of the mIgG-puromycin selection system, since the tested clones derived from 160 randomly selected clones and were selected with markedly lower effort than the standard approach clones (see FIG. 10).

Example 8

Determination of IgG Concentrations by ELISA

The immunoglobulin concentration in cell culture supernatants was determined by a sandwich ELISA which used a biotinylated anti-human IgG F(ab')2 fragment as the capture reagent and for detection a peroxidase-conjugated anti-human IgG F(ab')2 antibody fragment.

Streptavidin coated 96 well plates (Pierce Reacti-Bind™ Streptavidin Coated Polystyrene Strip Plates, Code No. 15121) were coated with 0.5 µg/ml biotinylated goat polyclonal anti-human IgG F(ab')2 antibody fragment (F(ab')2<h-Fcγ>Bi; Dianova, Germany, Code No. 109-066-098) capture antibody (0.1 ml/well) in diluent buffer (diluent buffer: PBS buffer containing 0.5% weight by volume (w/v) bovine serum albumin) by incubation for one hour at room temperature (RT) under shaking. Thereafter, the plates were washed three times with more than 0.3 ml wash buffer (wash buffer: PBS containing 1% (w/v) Tween 20). IgG containing cell culture supernatants (samples) were diluted serially (twofold) up to a concentration of 0.5-20 ng/ml in diluent buffer, added to the wells and incubated for one hour at RT with shaking. Purified standard antibody (0.5-20 ng/ml) in diluent buffer was used for the generation of an IgG protein standard curve. After washing the plates three times with 0.3 ml/well wash buffer, bound complexes to anti-human Fcγ were detected with a peroxidase-conjugated F(ab')2 fragment of goat polyclonal anti-human F(ab')2-specific IgG (F(ab')2<h-Fcγ>POD; Dianova, Germany, Code No. 109-036-098). After washing the plates three times with 0.3 ml/well wash buffer the plates were developed with ABTS® (2,2'-azino-bis(3-ethylbenzthiazoline-6-sulfonic acid) peroxidase substrate solution (Roche Diagnostics GmbH, Germany, Code No. 1684302). After 10-30 minutes the absorbance was measured at 405 nm and 490 nm against a reagent blank (incubation buffer+ABTS solution) on a Tecan Spectrafluorplus plate reader (Tecan Deutschland GmbH, Germany). For background correction the absorbance at 490 nm was subtracted from the absorbance at 405 nm according to the following formula:

$$\Delta A = (A_{sample}^{405nm} - A_{sample}^{490nm}) - (A_{blank}^{490nm} - A_{blank}^{405nm})$$

The IgG content of the samples were calculated from the standard curve.

Example 9

Determination of IgG Concentrations by Protein A Affinity Chromatography

The IgG concentrations in cell culture supernatants were determined by analytical affinity chromatography using an Äkta™ explorer chromatography unit (GE Healthcare, former Amersham Biosciences, Sweden). A defined volume of a cell culture supernatant was applied to a protein A sepharose column to facilitate binding of IgG to the affinity matrix. The column was washed with 100 mM citric acid pH 5.0, and then bound antibodies were eluted with 100 mM citric acid pH 3.0. The elution was monitored by continuous recording of the UV absorption of the eluate at 280 nm. The antibody concentration of a sample was calculated from the integrated UV absorption after calibration of the system with standard samples containing defined antibody concentrations.

---

The invention claimed is:

1. A nucleic acid comprising in 5' to 3' direction
   i) a first nucleic acid fragment encoding a polypeptide of interest without an in frame translational stop codon,
   ii) a second nucleic acid fragment operably linked to said first nucleic acid fragment which is beginning with the 5' splice donor site of an immunoglobulin heavy chain CH3 or CH4 domain and which is terminated by the 3' splice acceptor site of the succeeding immunoglobulin heavy chain transmembrane domain exon M1 and which comprises in frame translational stop codon and a polyadenylation signal,
   iii) a third nucleic acid fragment operably linked to said second nucleic acid encoding at least a fragment of a transmembrane domain,
   wherein the second nucleic acid fragment has at its 3' terminus the nucleotide sequence CTACCACCCCTTCCTGTCCAG (SEQ ID NO: 29) or TGACCACGCCAATCGTGTCCAG (SEQ ID NO: 14) or CTACCACGCCAATCGTGTCCAG (SEQ ID NO: 31).

2. A nucleic acid comprising in 5' to 3' direction
   i) a first nucleic acid fragment encoding a polypeptide of interest without an in frame translational stop codon,
   ii) a second nucleic acid fragment operably linked to said first nucleic acid fragment which is beginning with the 5' splice donor site of an immunoglobulin heavy chain CH3 or CH4 domain and which is terminated by the 3' splice acceptor site of the succeeding immunoglobulin heavy chain transmembrane domain exon M1 and which comprises in frame translational stop codon and a polyadenylation signal,
   iii) a third nucleic acid fragment operably linked to said second nucleic acid encoding at least a fragment of a transmembrane domain,
   wherein the nucleotide sequence CTACCACCCCTTCCTGTCCAGAGCTG (SEQ ID NO: 30) or TGACCACGCCAATCGTGTCCAGAGCTG (SEQ ID NO: 15) or CTACCACGCCAATCGTGTCCAGAGCTG (SEQ ID NO: 32) overlaps the second nucleic acid fragment and the third nucleic acid fragment.

3. The nucleic acid according to claim 1 or 2, wherein the second nucleic acid fragment which is beginning with the 5' splice donor site of an immunoglobulin heavy chain CH3 or CH4 domain and which is terminated by the 3' splice acceptor site of the succeeding immunoglobulin heavy chain transmembrane domain exon M1 and which comprises in frame translational stop codon and a polyadenylation signal further comprises 5' to the polyadenylation signal a nucleic acid encoding a selectable marker.

4. The nucleic acid according to claim 1 or 2, wherein the polypeptide of interest is an immunoglobulin heavy chain.

5. The nucleic acid according to claim 1, wherein the nucleic acid is comprised in an expression cassette.

6. The nucleic acid according to claim 1, wherein the second nucleic acid fragment comprises only one 5' splice donor site and only one 3' splice acceptor site.

7. The nucleic acid according to claim 1, wherein the second nucleic acid fragment is a naturally occurring immunoglobulin heavy chain intron, which is following the exon encoding an immunoglobulin heavy chain CH3 or CH4 domain, wherein in said intron at least 50 consecutive nucleotides are deleted.

8. The nucleic acid according to claim 1, wherein the first nucleic acid fragment encodes an immunoglobulin heavy chain and comprises all exons and all but one intron of the genomically organized immunoglobulin heavy chain gene.

9. The nucleic acid according to claim 1, wherein the third nucleic acid fragment encodes a fragment of a transmembrane domain, whereby the fragment of the transmembrane domain is encoded by a single exon.

10. The nucleic acid according to claim 1, wherein the transmembrane domain is an immunoglobulin transmembrane domain that is encoded by an M1-M2-exon-fusion (a single exon without the genomically intervening intron).

11. The nucleic acid according to claim 1, wherein the second nucleic acid fragment comprises the nucleotide sequence of SEQ ID NO: 11.

12. The nucleic acid according to claim 1, wherein the third nucleic acid fragment comprises the nucleotide sequence of SEQ ID NO: 12.

13. A method for selecting a eukaryotic cell expressing an immunoglobulin, whereby the method comprises
  a) transfecting a eukaryotic cell with one or more nucleic acids comprising a first expression cassette for an immunoglobulin light chain and a second expression cassette for an immunoglobulin heavy chain comprising a nucleic acid according to claim 4,
  b) culturing of said transfected cell under conditions suitable for the production of pre-mRNA from said nucleic acid, processing of said pre-mRNA, and translation of said processed mRNA into an immunoglobulin heavy chain, wherein said transfected cell produces soluble immunoglobulin and plasma-membrane-bound immunoglobulin by alternative splicing of said pre-mRNA, and
  c) selecting a cell with plasma-membrane-bound immunoglobulin to be said cell expressing an immunoglobulin.

* * * * *

SEQUENCE LISTING

```
<160> NUMBER OF SEQ ID NOS: 32

<210> SEQ ID NO 1
<211> LENGTH: 33
<212> TYPE: DNA
<213> ORGANISM: Artificial Sequence
<220> FEATURE:
<223> OTHER INFORMATION: pmIgGD-B intron 6-exon M1M2 junction

<400> SEQUENCE: 1
cagcactgac cacccccttc ctgtccagag ctg                             33

<210> SEQ ID NO 2
<211> LENGTH: 33
<212> TYPE: DNA
<213> ORGANISM: Artificial Sequence
<220> FEATURE:
<223> OTHER INFORMATION: pmIgGD-mut-bp intron 6-exon M1M2 junction

<400> SEQUENCE: 2
cagcacctac cacccccttc ctgtccagag ctg                             33

<210> SEQ ID NO 3
<211> LENGTH: 33
<212> TYPE: DNA
<213> ORGANISM: Artificial Sequence
<220> FEATURE:
<223> OTHER INFORMATION: pmIgGD-mut-p(Y) intron 6-exon M1M2 junction

<400> SEQUENCE: 3
cagcactgac cacgccaatc gtgtccagag ctg                             33

<210> SEQ ID NO 4
<211> LENGTH: 33
<212> TYPE: DNA
<213> ORGANISM: Artificial Sequence
<220> FEATURE:
<223> OTHER INFORMATION: pmIgGD-mut-bp-p(Y) intron 6-exon M1M2 junction

<400> SEQUENCE: 4
cagcacctac cacgccaatc gtgtccagag ctg                             33

<210> SEQ ID NO 5
<211> LENGTH: 24
<212> TYPE: DNA
<213> ORGANISM: Artificial Sequence
<220> FEATURE:
<223> OTHER INFORMATION: 3'-splice site consensus sequence
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t

<400> SEQUENCE: 5
```
nnytvayyyy yyyyyyyyny aggt                                            24

<210> SEQ ID NO 6
<211> LENGTH: 4608
<212> TYPE: DNA
<213> ORGANISM: Homo sapiens

<400> SEQUENCE: 6

| | | | | | |
|---|---|---|---|---|---|
| cctccaccaa | gggcccatcg | gtcttccccc | tggcaccctc | ctccaagagc | acctctgggg | 60 |
| gcacagcggc | cctgggctgc | ctggtcaagg | actacttccc | cgaaccggtg | acggtgtcgt | 120 |
| ggaactcagg | cgccctgacc | agcggcgtgc | acaccttccc | ggctgtccta | cagtcctcag | 180 |
| gactctactc | cctcagcagc | gtggtgaccg | tgccctccag | cagcttgggc | acccagacct | 240 |
| acatctgcaa | cgtgaatcac | aagcccagca | acaccaaggt | ggacaagaaa | gttggtgaga | 300 |
| ggccagcaca | gggagggagg | gtgtctgctg | gaagccaggc | tcagcgctcc | tgcctggacg | 360 |
| catcccggct | atgcagcccc | agtccagggc | agcaaggcag | ccccgtctg  | cctcttcacc | 420 |
| cggaggcctc | tgcccgcccc | actcatgctc | agggagaggg | tcttctggct | ttttccccgg | 480 |
| ctctgggcag | gcacaggcta | ggtgccccta | acccaggccc | tgcacacaaa | ggggcaggtg | 540 |
| ctgggctcag | acctgccaag | agccatatcc | gggaggaccc | tgcccctgac | ctaagcccac | 600 |
| cccaaaggcc | aaactctcca | ctccctcagc | tcggacacct | tctctcctcc | cagattccag | 660 |
| taactcccaa | tcttctctct | gcagagccca | aatcttgtga | caaaactcac | acatgcccac | 720 |
| cgtgcccagg | taagccagcc | caggcctcgc | cctccagctc | aaggcgggac | aggtgcccta | 780 |
| gagtagcctg | catccaggga | caggccccag | ccgggtgctg | acacgtccac | ctccatctct | 840 |
| tcctcagcac | ctgaactcct | ggggggaccg | tcagtcttcc | tcttcccccc | aaaacccaag | 900 |
| gacaccctca | tgatctcccg | gacccctgag | gtcacatgcg | tggtggtgga | cgtgagccac | 960 |
| gaagaccctg | aggtcaagtt | caactggtac | gtggacggcg | tggaggtgca | taatgccaag | 1020 |
| acaaagccgc | gggaggagca | gtacaacagc | acgtaccgtg | tggtcagcgt | cctcaccgtc | 1080 |
| ctgcaccagg | actggctgaa | tggcaaggag | tacaagtgca | aggtctccaa | caaagccctc | 1140 |
| ccagccccca | tcgagaaaac | catctccaaa | gccaaaggtg | ggacccgtgg | ggtgcgaggg | 1200 |
| ccacatggac | agaggccggc | tcggcccacc | ctctgccctg | agagtgaccg | ctgtaccaac | 1260 |
| ctctgtccct | acagggcagc | cccgagaacc | acaggtgtac | accctgcccc | catcccggga | 1320 |
| tgagctgacc | aagaaccagg | tcagcctgac | ctgcctggtc | aaaggcttct | atcccagcga | 1380 |
| catcgccgtg | gagtggggaga | gcaatgggca | gccggagaac | aactacaaga | ccacgcctcc | 1440 |
| cgtgctggac | tccgacggct | ccttcttcct | ctacagcaag | ctcaccgtgg | acaagagcag | 1500 |
| gtggcagcag | gggaacgtct | tctcatgctc | cgtgatgcat | gaggctctgc | acaaccacta | 1560 |
| cacgcagaag | agcctctccc | tgtctccggg | taaatgagtg | cgacggccgg | caagccccg  | 1620 |
| ctccccgggc | tctcgcggtc | gcacgaggat | gcttggcacg | tacccctgt  | acatacttcc | 1680 |
| cgggcgccca | gcatggaaat | aaagcaccca | gcgctgccct | gggcccctgc | gagactgtga | 1740 |
| tggttctttc | cacgggtcag | gccgagtctg | aggcctgagt | ggcatgaggg | aggcagagcg | 1800 |
| ggtcccactg | tccccacact | ggcccaggct | gtgcaggtgt | gcctgggccg | cctagggtgg | 1860 |
| ggctcagcca | ggggctgccc | tcggcagggt | ggggatttg  | ccagcgtggc | cctccctcca | 1920 |
| gcagcacctg | ccctgggctg | ggccacggga | agccctagga | gccctggggg | acagacacac | 1980 |
| agccccctgcc | tctgtaggag | actgtcctgt | tctgtgagcg | ccctgtcctc | cgacctccat | 2040 |

```
gcccactcgg gggcatgcct agtccatgcg cgtagggaca ggccctccct cacccatcta   2100
cccccacggc actaacccct ggcagccctg cccagcctcg cacccacatg gggacacaac   2160
cgactcctgg ggacatgcac tctcgggccc tgtggaggga ctggtccaga tgcccacaca   2220
cacactcagc ccagacccgt tcaacaaacc ccgcactgag gttggccggc cacacggcca   2280
ccacacacac acgtgcacgc ctcacacacg gagcttcacc cgggcgaacc gcacagcacc   2340
cagaccagag caaggtcctc gcacgcgtga acactcctcg gacacaggcc cccacgagcc   2400
ccacgcggca cctcaaggcc cacgagccgc tcggcagctt ctccacttgc tgaccagctc   2460
agacaaaccc agccctcctc tcacaaagtg cccctgcagc cgccacacac acacaggccc   2520
ccacacacag gggaacacac gccacgtcac gtccctggca ctggcccact tcccaataca   2580
gcccttccct gcagctgagg tcacatgagg tgtgggcttc accatcctcc tgccctctgg   2640
gcctcaggga gggacacggg agacggggag tgggtcctgc tgagggccag gcctctatct   2700
agggccgggt gtctggctga gtcccggggc caaagctggt gcccagggcg ggcagctgtg   2760
gggagctgac ctcaggacac tgttggccca tcccggccgg ccctacatc ctgggccccg   2820 ccacagaggg aatcaccccc agaggcccaa gcccaggggg acacagcact gaccacccccc   2880 ttcctgtcca gagctgcaac tggaggagag ctgtgcggag gcgcaggacg gggagctgga   2940
cgggctgtgg acgaccatca ccatcttcat cacactcttc ctgctaagcg tgtgctacag   3000
tgccaccgtc accttcttca aggtgaagtg gatcttctcc tcggtggtgg acctgaagca   3060
gaccatcgtc cccgactaca ggaacatgat aaggcagggg gcctagggcc accctctgcg   3120
gggtgtccag ggccgcccag accccacaca cgagccgtgg gccatgctca gccaccaccc   3180
aggccacacc tgcccctga cctcaccgcc ctcaaccca tggctctctg gcttcgcagt   3240
cgccctctga gcctgaaac gccccccttc cagaccctgt gcatagcagg tctaccccag   3300
acctccgctg cttggtgcca gggcactggg ggccaggtgt cccctcagca ggacgtccct   3360
gccctctgga ccaccaggtg ctcacacaaa aggaggtaac cggcatccca ggcccccact   3420
caggcaggac ctcgccctgg agccaacccc gtccacgcca gcctcctgaa cacaggcatg   3480
gtttccagat ggtgagtggg agcatcagtc gccaaggtag ggaagccaca gcaccatcag   3540
gccctgttgg ggaggcttcc gagagctgcg aaggctcact cagacggcct tcctcccagc   3600
ccgcagccag ccagcctcca ttccgggcac tcccgtgaac tcctgacatg aggaatgagg   3660
ttgttctgat ttcaagcaaa gaacgctgct ctctggctcc tgagaacagt ctcggtgcca   3720
gcaccacccc ttggctgcct gcccacactg ctggattctc gggtggaact cgacccgcag   3780
ggacagccag ccccagagtc cgcactgggg agagaagggg ccaggccag gacactgcca   3840 cctcccaccc actccagtcc accgagatca ctcagagaag agcctgggcc atgtggccgc   3900
tgcaggagcc ccacagtgca agggtgagga tagcccaagg aagggctggg catctgccca   3960
gacaggcctc ccacagaagg ctggtgacca ggtcccaggc gggcaagact cagccttggt   4020
ggggcctgag gacagaggag gcccaggagc atcgggaga gaggtggagg gacaccggga   4080
gagccaggag cgtggacaca gccagaactc accacagagg ctggcgtcca gtcccgggtc   4140
acgtgcagca ggaacaagca gccactctgg gggcaccagg tggagaggca agacgacaaa   4200
gagggtgccc gtgttcttgc gaaagcgggg ctgctggcca cgagtgctgg acagaggccc   4260
ccacgctctg ctgcccccat cacgccgttc cgtgactgtc acgcagaatc cacagacagg   4320
aagggaggct cgagcgggac tgcggccagc gcctgcctcg gccgtcaggg aggactcctg   4380
ggctcactcg aaggaggtgt caccatttca gctttggctt ttcttcttct tttaaatttt   4440
```

```
ctaaagctca ttaattgtct tgatgtttc tttttgatg acaataaaat atccttttta    4500
agtcttgtac ttcgtgatgg gagccacctt cctgtgtcca cgcgcctcct gcccccggtg    4560
gaaaacacgg tcaggaggag gctggtccag ctgcacctcg ggggatcc                 4608
```

<210> SEQ ID NO 7
<211> LENGTH: 330
<212> TYPE: PRT
<213> ORGANISM: Artificial
<220> FEATURE:
<223> OTHER INFORMATION: Amino acid sequence of the short (sIgG) isoform
      of the gamma-chain constant region encoded by plasmid pmIgGdelta-A

<400> SEQUENCE: 7

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
```

<210> SEQ ID NO 8
<211> LENGTH: 399
<212> TYPE: PRT
<213> ORGANISM: Artificial
<220> FEATURE:
<223> OTHER INFORMATION: Amino acid sequence of the long (mIgG) isoform
of the gamma-chain constant region encoded by plasmid pmIgGdelta-A

<400> SEQUENCE: 8

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Glu Leu Gln Leu Glu Glu Ser Cys
                325                 330                 335

Ala Glu Ala Gln Asp Gly Glu Leu Asp Gly Leu Trp Thr Thr Ile Thr
            340                 345                 350
```

```
Ile Phe Ile Thr Leu Phe Leu Leu Ser Val Cys Tyr Ser Ala Thr Val
        355                 360                 365

Thr Phe Phe Lys Val Lys Trp Ile Phe Ser Ser Val Val Asp Leu Lys
    370                 375                 380

Gln Thr Ile Val Pro Asp Tyr Arg Asn Met Ile Arg Gln Gly Ala
385                 390                 395

<210> SEQ ID NO 9
<211> LENGTH: 50
<212> TYPE: DNA
<213> ORGANISM: Artificial Sequence
<220> FEATURE:
<223> OTHER INFORMATION: pmIgGD-B intron 6-excon M1M2 for ESEfinder

<400> SEQUENCE: 9
ctgtccagag ctgcaactgg aggagagctg tgcggaggcg caggacgggg           50

<210> SEQ ID NO 10
<211> LENGTH: 50
<212> TYPE: DNA
<213> ORGANISM: Artificial Sequence
<220> FEATURE:
<223> OTHER INFORMATION: pmIgGD-mut-ESE

<400> SEQUENCE: 10
ctgtccagaa ttgcaattgg aagagagctg tgctgaagct caagatgggg           50

<210> SEQ ID NO 11
<211> LENGTH: 1287
<212> TYPE: DNA
<213> ORGANISM: Homo sapiens

<400> SEQUENCE: 11
gtaaatgagt gccacggccg gcaagccccc gctccccagg ctctcggggt cgcgcgagga    60
tgcttggcac gtaccccgtg tacatacttc ccaggcaccc agcatggaaa taaagcaccc   120
agcgcttccc tgggcccctg cgagactgtg atggttcttt ccacgggtca ggccgagtct   180
gaggcctgag tggcatgagg gaggcagagt gggtcccact gtccccacac tggcccaggc   240
tgtgcaggtg tgcctgggcc gcctagggtg gggctcagcc aggggctgcc ctcggcaggg   300
tgggggattt gccagcgtgg ccctccctcc agcagcagct gccctgggct gggccacgag   360
aagccctagg agccctggg gacagacaca cagcccctgc ctctgtagga gactgtcctg   420
ttctgtgagc gccctgtcct ccgacccgca tgcccactcg ggggcatgcc tagtccatgt   480
gcgtagggac aggccctccc tcacccatct accccacgg cactaacccc tggcagccct   540
gcccagcctc gcaccgcat ggggacacaa ccgactccgg ggacatgcac tctcgggccc   600
tgtggagaga ctggtccaga tgcccacaca cacactcagc ccagacccgt caacaaacc    660 ccgcactgag gttggccggc cacacggcca ccacacacac acgtgcacgc ctcacacacg   720
gagcctcacc cggcgaacc gcacagcacc cagaccagag caaggtcctc gcacacgtga    780
acactcctcg gacacaggcc cccacgagcc ccacgcggca cctcaaggcc cacgagccgc   840
tcggcagctt ctccacatgc tgacctgctc agacaaaccc agccctcctc tcacaaggtg   900
cccctgcagc cgccacacac acacagggga tcacacacca cgtcacgtcc ctggccctgg   960
cccacttccc agtgccgccc ttccctgcag ctggggtcac atgaggtgtg ggcttcacca  1020
tcctcctgcc ctctgggcct caggaggga cacgggagac ggggagcggg tcctgctgag   1080
ggccaggtcg ctatctaggg ccgggtgtct ggctgagccc cggggccaaa gctggtgccc   1140
```

```
agggcgggca gctgtgggga gctgacctca ggacattgtt ggcccatccc ggccgggccc   1200
tacatcctgg gtcctgccac agagggaatc accccccagag gcccaagccc aggggggacac  1260 agcactgacc acgccaatcg tgtccag                                        1287

<210> SEQ ID NO 12
<211> LENGTH: 78
<212> TYPE: DNA
<213> ORGANISM: Homo sapiens

<400> SEQUENCE: 12
gggctgtgga cgaccatcac catcttcatc acactcttcc tgttaagcgt gtgctacagt    60
gccaccgtca ccttcttc                                                  78

<210> SEQ ID NO 13
<211> LENGTH: 29
<212> TYPE: DNA
<213> ORGANISM: Homo sapiens

<400> SEQUENCE: 13
agctgcaact ggaggagagc tgtgcggag                                      29

<210> SEQ ID NO 14
<211> LENGTH: 22
<212> TYPE: DNA
<213> ORGANISM: Artificial Sequence
<220> FEATURE:
<223> OTHER INFORMATION: 3'-fragment of intron 6 of an immunoglobulin
      heavy chain structural gene

<400> SEQUENCE: 14
tgaccacgcc aatcgtgtcc ag                                             22

<210> SEQ ID NO 15
<211> LENGTH: 27
<212> TYPE: DNA
<213> ORGANISM: Artificial Sequence
<220> FEATURE:
<223> OTHER INFORMATION: nucleic acid at the junction of intron 6 and
      exon M1 of an immunoglobulin heavy chain structural gene

<400> SEQUENCE: 15
tgaccacgcc aatcgtgtcc agagctg                                        27

<210> SEQ ID NO 16
<211> LENGTH: 2074
<212> TYPE: DNA
<213> ORGANISM: Homo sapiens

<400> SEQUENCE: 16
cctccaccaa gggcccatcg gtcttccccc tggcaccctc ctccaagagc acctctgggg    60
gcacagcggc cctgggctgc ctggtcaagg actacttccc cgaaccggtg acggtgtcgt   120
ggaactcagg cgccctgacc agcggcgtgc acaccttccc ggctgtccta cagtcctcag   180
gactctactc cctcagcagc gtggtgaccg tgccctccag cagcttgggc acccagacct   240
acatctgcaa cgtgaatcac aagcccagca acaccaaggt ggacaagaaa gttggtgaga   300
ggccagcaca gggagggagg gtgtctgctg gaagccaggc tcagcgctcc tgcctggacg   360
catcccggct atgcagcccc agtccagggc agcaaggcag gccccgtctg cctcttcacc   420
cggaggcctc tgcccgcccc actcatgctc agggagaggg tcttctggct ttttccccgg   480
ctctgggcag gcacaggcta ggtgccccta acccaggccc tgcacacaaa ggggcaggtg   540
```

```
ctgggctcag acctgccaag agccatatcc gggaggaccc tgcccctgac ctaagcccac    600
cccaaaggcc aaactctcca ctccctcagc tcggacacct ctctcctcc  cagattccag    660
taactcccaa tcttctctct gcagagccca atcttgtga  caaaactcac acatgcccac    720
cgtgccagg  taagccagcc caggcctcgc cctccagctc aaggcgggac aggtgcccta    780
gagtagcctg catccaggga caggcccag  ccgggtgctg acacgtccac ctccatctct    840
tcctcagcac ctgaactcct ggggggaccg tcagtcttcc tcttcccccc aaaacccaag    900
gacaccctca tgatctcccg acccctgag  gtcacatgcg tggtggtgga cgtgagccac    960
gaagaccctg aggtcaagtt caactggtac gtggacggcg tggaggtgca taatgccaag   1020
acaaagccgc gggaggagca gtacaacagc acgtaccgtg tggtcagcgt cctcaccgtc   1080
ctgcaccagg actggctgaa tggcaaggag tacaagtgca aggtctccaa caaagccctc   1140
ccagccccca tcgagaaaac catctccaaa gccaaaggtg gacccgtgg  ggtgcgaggg   1200
ccacatggac agaggccggc tcggcccacc ctctgccctg agagtgaccg ctgtaccaac   1260
ctctgtccct acagggcagc cccgagaacc acaggtgtac accctgcccc catcccggga   1320
tgagctgacc aagaaccagg tcagcctgac ctgcctggtc aaaggcttct atcccagcga   1380
catcgccgtg gagtgggaga gcaatgggca gccggagaac aactacaaga ccacgcctcc   1440
cgtgctggac tccgacggct ccttcttcct ctacagcaag ctcaccgtgg acaagagcag   1500
gtggcagcag gggaacgtct tctcatgctc cgtgatgcat gaggctctgc acaaccacta   1560
cacgcagaag agcctctccc tgtctccggg taaatgagtg cgacggccgg caagcccccg   1620
ctccccgggc tctcgcggtc gcacgaggat gcttggcacg tacccctgt  acatacttcc   1680
cgggcgccca gcatggaaat aaagcaccca gcgctgccct gggcccctgc gagactgtga   1740
tggttctttc cacgggtcag gccgagtctg aggcctgagt ggcatgaggg aggcagagcg   1800
ggtcccactg tccccacact ggcccaggct gtgcaggtgt gcctgggccg cctagggtgg   1860
ggctcagcca ggggctgccc tcggcagggt ggggatttg  ccagcgtggc cctccctcca   1920
gcagcacctg ccctgggctg gccacgggga gccctagga  gccctgggg  acagacacac   1980
agccctgcc  tctgtaggag actgtcctgt tctgtgagcg ccctgtcctc cgacctccat   2040
gcccactcgg gggcatgcga cagattgagg atcc                                2074
```

<210> SEQ ID NO 17
<211> LENGTH: 330
<212> TYPE: PRT
<213> ORGANISM: Artificial
<220> FEATURE:
<223> OTHER INFORMATION: Amino acid sequence of the gamma-chain constant region encoded by plasmid pIgG-A

<400> SEQUENCE: 17

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80
```

-continued

```
Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 18
<211> LENGTH: 40
<212> TYPE: DNA
<213> ORGANISM: Artificial
<220> FEATURE:
<223> OTHER INFORMATION: TM-fw1

<400> SEQUENCE: 18
ggccgagtct gaggcctgag tggcatgagg gaggcagagt          40

<210> SEQ ID NO 19
<211> LENGTH: 48
<212> TYPE: DNA
<213> ORGANISM: Artificial
<220> FEATURE:
<223> OTHER INFORMATION: TM-rv1

<400> SEQUENCE: 19
aactggatcc atgtagaaaa gaggagaagc cccgggggtc catgtagt          48

<210> SEQ ID NO 20
<211> LENGTH: 47
<212> TYPE: DNA
<213> ORGANISM: Artificial
<220> FEATURE:
<223> OTHER INFORMATION: M1-rv

<400> SEQUENCE: 20
gatccacttc accttgaaga aggtgacggt ggcactgtag cacacgc　　　　　　　47

<210> SEQ ID NO 21
<211> LENGTH: 49
<212> TYPE: DNA
<213> ORGANISM: Artificial
<220> FEATURE:
<223> OTHER INFORMATION: M2-fw

<400> SEQUENCE: 21
caccttcttc aaggtgaagt ggatcttctc ctcggtggtg gacctgaag　　　　　　49

<210> SEQ ID NO 22
<211> LENGTH: 33
<212> TYPE: DNA
<213> ORGANISM: Artificial
<220> FEATURE:
<223> OTHER INFORMATION: TM-fw2

<400> SEQUENCE: 22
ctccagcagc agctgccctg ggctgggcca cga　　　　　　　　　　　　　　33

<210> SEQ ID NO 23
<211> LENGTH: 50
<212> TYPE: DNA
<213> ORGANISM: Artificial
<220> FEATURE:
<223> OTHER INFORMATION: TM-rv2

<400> SEQUENCE: 23
cagggatccc ccgaggtgca gctggaccag cctcctcctg accgtgtttt　　　　　50

<210> SEQ ID NO 24
<211> LENGTH: 68
<212> TYPE: DNA
<213> ORGANISM: Artificial
<220> FEATURE:
<223> OTHER INFORMATION: mutSphI-1

<400> SEQUENCE: 24
ctacccagga cctccgctgc ttggtgcctg cagggcactg ggggccaggt gtcccctcag　　60 caggacgt　　　　　　　　　　　　　　　　　　　　　　　　　　　68

<210> SEQ ID NO 25
<211> LENGTH: 62
<212> TYPE: DNA
<213> ORGANISM: Artificial
<220> FEATURE:
<223> OTHER INFORMATION: mutSphI-2

<400> SEQUENCE: 25
cctgctgagg ggacacctgg cccccagtgc cctgcaggca ccaagcagcg gaggtctggg　　60 gt　　　　　　　　　　　　　　　　　　　　　　　　　　　　　　62

<210> SEQ ID NO 26
<211> LENGTH: 6949
<212> TYPE: DNA
<213> ORGANISM: Homo sapiens

<400> SEQUENCE: 26
cctccaccaa gggcccatcg gtcttccccc tggcaccctc ctccaagagc acctctgggg　　60

```
gcacagcggc cctgggctgc ctggtcaagg actacttccc cgaaccggtg acggtgtcgt    120
ggaactcagg cgccctgacc agcggcgtgc acaccttccc ggctgtccta cagtcctcag    180
gactctactc cctcagcagc gtggtgaccg tgccctccag cagcttgggc acccagacct    240
acatctgcaa cgtgaatcac aagcccagca acaccaaggt ggacaagaaa gttggtgaga    300
ggccagcaca gggagggagg gtgtctgctg gaagccaggc tcagcgctcc tgcctggacg    360
catcccggct atgcagcccc agtccagggc agcaaggcag gccccgtctg cctcttcacc    420
cggaggcctc tgcccgcccc actcatgctc agggagaggg tcttctggct ttttccccgg    480
ctctgggcag gcacaggcta ggtgcccta  acccaggccc tgcacacaaa ggggcaggtg    540
ctgggctcag acctgccaag agccatatcc gggaggaccc tgcccctgac ctaagcccac    600
cccaaaggcc aaactctcca ctccctcagc tcggacacct tctctcctcc cagattccag    660
taactcccaa tcttctctct gcagagccca atcttgtga  caaaactcac acatgcccac    720
cgtgcccagg taagccagcc caggcctcgc cctccagctc aaggcgggac aggtgcccta    780
gagtagcctg catccaggga caggcccag  ccgggtgctg acacgtccac ctccatctct    840
tcctcagcac ctgaactcct gggggaccg  tcagtcttcc tcttccccc  aaaacccaag    900
gacaccctca tgatctcccg gacccctgag gtcacatgcg tggtggtgga cgtgagccac    960
gaagaccctg aggtcaagtt caactggtac gtggacggcg tggaggtgca taatgccaag   1020
acaaagccgc gggaggagca gtacaacagc acgtaccgtg tggtcagcgt cctcaccgtc   1080
ctgcaccagg actggctgaa tggcaaggag tacaagtgca aggtctccaa caaagccctc   1140
ccagccccca tcgagaaaac catctccaaa gccaaaggtg ggacccgtgg ggtgcgaggg   1200
ccacatggac agaggccggc tcggcccacc ctctgccctg agagtgaccg ctgtaccaac   1260
ctctgtccct acagggcagc cccgagaacc acaggtgtac accctgcccc catcccggga   1320
tgagctgacc aagaaccagg tcagcctgac ctgcctggtc aaaggcttct atcccagcga   1380
catcgccgtg gagtgggaga gcaatgggca gccggagaac aactacaaga ccacgcctcc   1440
cgtgctggac tccgacggct ccttcttcct ctacagcaag ctcaccgtgg acaagagcag   1500
gtggcagcag gggaacgtct tctcatgctc cgtgatgcat gaggctctgc acaaccacta   1560
cacgcagaag agcctctccc tgtctccggg taaatgagtg cgacggccgg caagcccccg   1620
ctccccgggc tctcgcggtc gcacgaggat gcttggcacg taccccctgt acatacttcc   1680
cgggcgccca gcatggaaat aaagcaccca gcgctgccct gggcccctgc gagactgtga   1740
tggttctttc cacgggtcag gccgagtctg aggcctgagt ggcatgaggg aggcagagcg   1800
ggtcccactg tccccacact ggcccaggct gtgcaggtgt gcctgggccg cctagggtgg   1860
ggctcagcca ggggctgccc tcggcagggt gggggatttg ccagcgtggc cctccctcca   1920
gcagcacctg ccctgggctg gccacgggaa gccctagga  gccctgggg  acagacacac   1980
agcccctgcc tctgtaggag actgtcctgt tctgtgagcg ccctgtcctc cgacctccat   2040
gcccactcgg gggcatgcct agtccatgcg cgtagggaca ggcctccct  cacccatcta   2100
cccccacggc actaacccct ggcagccctg cccagcctcg cacccgcatg ggacacaac    2160
cgactccggg gacatgcact ctcggggcct gtggagggac tggtgcagat gcccacacac   2220
acactcagcc cagacccgtt caacaaaccc cgcactgagg ttggccggcc acacggccac   2280
cacacacaca cgtgcacgcc tcacacacgg agcctcaccc gggcgaaccg cacagcaccc   2340
agaccagagc aaggtcctcg cacacgtgaa cactcctcgg acacaggccc ccacgagccc   2400
cacgcggcac ctcaaggccc acgagccgct cggcagcttc tccacatgct gacctgctca   2460
```

```
gacaaaccca gccctcctct cacaaggtgc ccctgcagcc gccacacaca cacaggcccc    2520
cacacgcagg ggaacacacg ccacgtcgcg tccctggcac tggcccactt cccaatacag    2580
cccttccctg cagctggggt cacatgaggt gtgggcttca ccatcctcct gccctctggg    2640
cctcagggag ggacacggga gacggggagc gggtcctgct gagggccagg tcgctatcta    2700
gggccgggtg tctggctgag tcccggggcc aaagctggtg cccagggcgg gcagctgtgg    2760
ggagctgacc tcaggacatt gttggcccat cccggccggg ccctacatcc tgggccccgc    2820
cacagaggga atcacccccca gaggcccaag cccaggggga cacagcactg accacccccct   2880 tcctgtccag agctgcaact ggaggagagc tgtgcgaggg cgcaggacgg ggagctggac    2940
gggctgtgga cgaccatcac catcttcatc acactcttcc tgttaagcgt gtgctacagt    3000
gccaccgtca ccttcttcaa ggtcggccgc acgttgtccc cagctgtcct tgacattgtc    3060
ccccatgctg tcacaaactg tctctgacac tgtcccacag gctgtcccca cctgtccctg    3120
acgctgtccc ccatgctctc acaaactgtc cctgacattg tccccaatgc tgcccccacc    3180
tgtccaacag tgtcccccag gctctcccca catgtcccg  acactgtccc ccatgctgtc    3240
cccatctgtc cccaacactg tcccccaccc tgtcccccctt tgtccccaac actgtccccc   3300
acagtttcca cctgtccctg acactgtccc ccatgctttc cccacctgtc cctgacacca    3360
tcccccactc tgtccctat  agttcctggc cctgtccccc acgctgtccc ctacagtacc    3420
tggcactgtc ccccatgctg tccctcctg  tatgaaaccc tgtcccacat gctgtcccca    3480
cctgtccgtg acaatatccc ccacactgtc cccacctgtc cccgacactc tcctccacgt    3540
tgttcttacc taaacccgac actttcctcc atgctgtccc cacccatctc cgacactgta    3600
ccccacgttg tccccacctg tcctcaacac tgtcccccat gctgtcccca cctgtcccca    3660
acactctcct ccatgctgtc cccacctgtc cctgatattg tccccatgc  agtctccacc    3720 tgtccccaat gctgtccccc aggctgtacc taccagtaca acactgtccc ccatgctgtc    3780
cccacctgtc cctgacactg tccccacgc  tgtcccctcc tgtccccgac actgtccccc    3840
acactgtccc cacctgtccc caacactatc ctccatgctg tccctcctg  tccccacctg    3900 tccctacac  tgtccccat  gctgtcccca ccagtcccca aaacttcct  ccacactgtc    3960 cccacctgtc cccaacactg tccccacgc tatccccct  gtcccgaca  atgtccccac     4020 tgttcctcc  tgttccctcc tatcctgac  actgtccgcc atgctgtccc cacctgtccc    4080
tgacactgtc tcccactctg tccctataa  tcctgacac  tgtccccac  gccgtccct     4140 cccgtatgca ccactgtccc ccaagctgtc cccacctgtc ctcaacacag tccccatgc     4200 tgtccccacc tgtccccaac actctcctcc atgtccccac ctgtccctga tattgtcccc    4260
catgcagtcc ccacctgtcc ccgatgctgt ccccgggct  gtacctacca gtccaacact    4320
gtcccccaca ctctccccac ctgtccctga tactgtcccc catgctgtcc ccacctgtcc    4380
cggacactgt tctccacgat ctcccctcct gtccctgaca ctgtccccca cactgtcccc    4440
acctgtcccc aacactatcc tccatcctgt cccaacctgt ctcctacact gtccccccatg   4500 ctgtccccac cagtccccaa cactgtcctc catgctgtcc ccatgtccc  caacactgtc    4560 ccccatgcta cctccctgc  ccctgacaat gtccccactg tttcctgtcc cctcctatcc    4620
ctgacactgt ccccatgct  gtccccacct gtccccaca  tggtctccac cggtccctga    4680
cactgtctcc cactctgtcc cctataatcc ctgacactgt ccccacacc  gtccctcct     4740 gtatgcacca cggtccccca tgctgtcccc acctgtccct gatgctgtcc tccacacagt    4800
```

-continued

```
ccccacctct ccctgacact gtccccatct ctccccaaca ctctcctcca tgctgtcctc    4860
aactgtcccc aacactcttc cacactctgt ctccacctgt ccctgacact gtcccccaca    4920
ctgtcctcac ctgtgtctga cactgtcccc cacgctgtcc ccacctgtcc ctgacgctgt    4980
cttctgtgct gtccacatgc tgttggtgcc ctggctctgc tctctatcac caagcctcag    5040
agcaggcagt ggtgaggcca tggcacctgg gtggcatgag gggccggatg ggcctcaggg    5100
gcagggctgt ggcctgcgtg gactgacagg tgggtgggcc ttgggggcag agaggtggcc    5160
tcagtgccct gaggggtggg tggggctcgg gggcagggct gtggcctcgc tcacccctgt    5220
gctgtgcctt gcctacaggt gaagtggatc ttctcctcgg tggtggacct gaagcagacc    5280
atcatccccg actacaggaa catgatcgga caggggcct agggccaccc tctgcgggt    5340
gtccagggcc gcccagaccc cacacaccag ccatggccca tgctcagcca cccccaggc    5400
cacacctgcc cccgacctca ccgccctcaa ccccatggct ctctggcctc gcagttgccc    5460
tctgaccctg acacctgga cacgcccccc ttccagaccc tgtgcatagc aggtctaccc    5520
cagacctccg ctgcttggtg cctgcagggc actgggggcc aggtgtcccc tcagcaggac    5580
gtccttgccc tccggaccac aaggtgctca cacaaaagga ggcagtgacc ggtatcccag    5640
gccccacc aggcaggagc tggccctgga gccaaccccg tccacgccag cctcctgaac    5700
acaggcgtgg tttccagatg gtgagtggga gcatcagccg ccaaggtagg aagccacag    5760
caccatcagg ccctgtgggg gaggcttccg agagctgcga aggctcactc agacggcctt    5820
cctcccagcc cgcagccagc cagcctccat tccgggcact cccgtgaact cctgacatga    5880
ggaatgacgt tgttctgatt tcaagcaaag aacgctgctc tctggctcct gggaacagtc    5940
tcggtgccag caccacccct tggctgcctg cccacactgc tggattctcg ggtggaactc    6000
gacccgcagg acagccagc cccagagtcc gcactgggga gagaagggc caggcccagg    6060
acactgccac ctcccaccca ctccagtcca ccgagatcac tcggagaaga gtctgggcca    6120
tgtggccgct gcaggagccc cacagtgcaa gggtgaggat agcccaagga agggctgggc    6180
atctgcccag acaggcctcc cacagaaggc tggtgaccag gtcccaggcg gcaagactc    6240
agccttggtg gggcctgagg acagaggagg cccaggagca tcggggagag aggtggaggg    6300
acaccgggag agccagggc gtggacacag ccagaactca tcacagaggc tggcgtccag    6360
tcccgggtca tgtgcagcag gaacaagcag ccactctggg ggcaccaggt ggagaggcaa    6420
gacgacaaag agggtgcccg tgttcttgcg aaagcggggc tgctggccac gagtgctgga    6480
cagaggcccc cacgctctgc tgcccccatc acgccgttcc gtgactgtca cgcagaatct    6540
gcagacagga agggagactc gagcgggagt gcggccagag cctgcctcgg ccgtcaggga    6600
ggactcccgg gctcactcga aggaggtgcc accatttcag ctttggtagc ttttcttctt    6660
cttttaaatt ttctaaagct cattaattgt ctttgatgtt tcttttgtga tgacaataaa    6720
atatcctttt taagtcttgt acttcgtgat gggagccgcc ttcctgtgtc cacgcgcctc    6780
ctgccccgg tgggaagcac ggtcaggagg aggctggtcc agctgcacct cggggctcc    6840
ctgcactcgc ccccgcctc ctgcagccac acgcattgcc cgagcgaccc tccctggccc    6900
ctgtcactac atggacccc ggggcttctc ctctttctca catggatcc                6949
```

<210> SEQ ID NO 27
<211> LENGTH: 330
<212> TYPE: PRT
<213> ORGANISM: Homo sapiens

<400> SEQUENCE: 27

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 28
<211> LENGTH: 399
<212> TYPE: PRT
<213> ORGANISM: Homo sapiens

<400> SEQUENCE: 28

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
```

```
            35                  40                  45
Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
                115                 120                 125

Lys Pro Lys Asp Thr Leu Met Ile Ser Arg Thr Pro Glu Val Thr Cys
                130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Glu Leu Gln Leu Glu Glu Ser Cys
                325                 330                 335

Ala Glu Ala Gln Asp Gly Glu Leu Asp Gly Leu Trp Thr Thr Ile Thr
                340                 345                 350

Ile Phe Ile Thr Leu Phe Leu Leu Ser Val Cys Tyr Ser Ala Thr Val
                355                 360                 365

Thr Phe Phe Lys Val Lys Trp Ile Phe Ser Ser Val Val Asp Leu Lys
                370                 375                 380

Gln Thr Ile Ile Pro Asp Tyr Arg Asn Met Ile Gly Gln Gly Ala
385                 390                 395

<210> SEQ ID NO 29
<211> LENGTH: 22
<212> TYPE: DNA
<213> ORGANISM: Artificial Sequence
<220> FEATURE:
<223> OTHER INFORMATION: mutated 3'-fragment of intron 6

<400> SEQUENCE: 29
ctaccacccc cttcctgtcc ag                                          22
```

```
<210> SEQ ID NO 30
<211> LENGTH: 27
<212> TYPE: DNA
<213> ORGANISM: Artificial Sequence
<220> FEATURE:
<223> OTHER INFORMATION: mutated 3'-fragment of intron 6 with exon
      fragment

<400> SEQUENCE: 30
ctaccacccc cttcctgtcc agagctg                                           27

<210> SEQ ID NO 31
<211> LENGTH: 22
<212> TYPE: DNA
<213> ORGANISM: Artificial Sequence
<220> FEATURE:
<223> OTHER INFORMATION: mutated 3'-fragment of intron 6 II

<400> SEQUENCE: 31
ctaccacgcc aatcgtgtcc ag                                                22

<210> SEQ ID NO 32
<211> LENGTH: 27
<212> TYPE: DNA
<213> ORGANISM: Artificial Sequence
<220> FEATURE:
<223> OTHER INFORMATION: mutated 3'-fragment of intron 6 II with exon
      fragment

<400> SEQUENCE: 32
ctaccacgcc aatcgtgtcc agagctg                                           27
```